Figure 3:
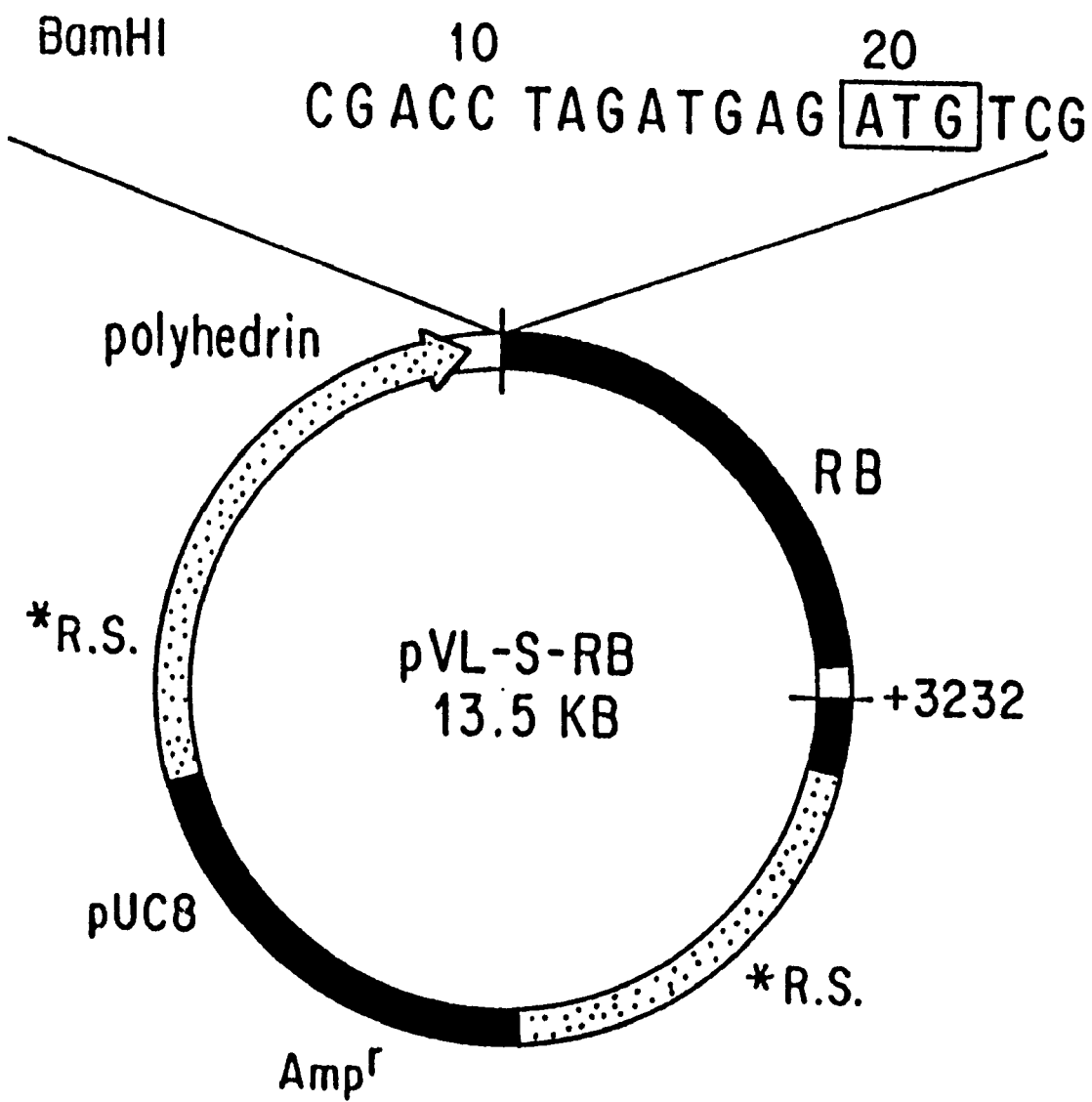

US005912236A

United States Patent [19]

Xu et al.

[11] Patent Number: 5,912,236
[45] Date of Patent: Jun. 15, 1999

[54] BROAD-SPECTRUM TUMOR SUPPRESSOR GENES GENE PRODUCTS AND METHODS FOR TUMOR SUPPRESSOR GENE THERAPY

[75] Inventors: Hong-Ji Xu; Shi-Xue Hu; William F. Benedict, all of The Woodlands, Tex.

[73] Assignee: Baylor College of Medicine, Houston, Tex.

[21] Appl. No.: 08/470,091

[22] Filed: Jun. 6, 1995

Related U.S. Application Data

[62] Division of application No. 08/038,760, Mar. 25, 1993, Pat. No. 5,496,731.

[51] Int. Cl.[6] .......................... A01N 43/04; A61N 63/00; C12N 5/10; C12N 15/09
[52] U.S. Cl. .......................... 514/44; 424/93.1; 424/93.2; 424/93.21; 424/93.6; 424/93.7; 435/320.1; 435/440; 435/455; 435/456; 435/458
[58] Field of Search .............................. 435/172.3, 320.1, 435/325, 440, 455, 456, 458; 514/44; 530/350; 536/23.1, 23.5; 424/93.1, 93.2, 93.21, 93.6, 93.7

[56] References Cited

U.S. PATENT DOCUMENTS

| | | | |
|---|---|---|---|
| 4,740,463 | 4/1988 | Weinberg et al. | 435/172.3 |
| 4,942,123 | 7/1990 | Lee et al. | 435/7.23 |
| 5,174,993 | 12/1992 | Paoletti | 424/199.1 |

FOREIGN PATENT DOCUMENTS

| | | |
|---|---|---|
| A-80426/91 | 7/1991 | Australia . |
| 0 259 031 | 8/1987 | European Pat. Off. . |
| WO 88/09387 | 5/1988 | WIPO . |
| WO 89/03429 | 8/1988 | WIPO . |
| WO 89/06703 | 1/1989 | WIPO . |
| WO 90/05180 | 10/1989 | WIPO . |
| WO 90/12807 | 4/1990 | WIPO . |
| WO 91/15580 | 4/1991 | WIPO . |
| WO 92/05272 | 9/1991 | WIPO . |

OTHER PUBLICATIONS

Af Trampe et al., 1983, Results Obtained in Treating Retinoblastoma patients with Different Techniques at the Karolinska Hospital, *Springer–Verlag* pp. 529–533.

Ahlering et al., 1987, A New in Vivo Model to Study Invasion and Metastasis of Human Bladder Carcinoma, *Cancer Research* 47:6660–6665.

Akiyama et al., 1990, Marked alteration in phosphorylation of the RB protein during differentiation of human promyelocytic HL 60 cells, *Oncogene* 5:179–183.

Anderson, 1992, Human Gene Therapy, *Science* 256:808–813.

Ausubel et al., 1992, Short Protocols in Molecular Biology, *Current Protocols in Molecular Biology*, John Wiley and Jones, New York.

Baker et al., 1990, Suppression of Human Colorectal Carcinoma Cell Growth by Wild–Type p53, *Science* 249:912–915.

Ballester et al, 1990, The NF1 Locus Encodes a Protein Functionally Related to Mammalian GAP and Yeast IRA Proteins, *Cell* 63:851–859.

Banerjee et al., 1992, Changes in Growth and Tumorigenicity following Reconstitution of Retinoblastoma Gene Function in Various Human Cancer Cell Types by Microcell Transfer of Chromosome 13, *Cancer Research* 52:6297–6304.

Bayer et al., 1980, The Use of the Avidin–Biotin Complex as a Tool in Molecular Biology, *Methods Biochem. Anal.* 26:1–45.

Benedict et al.,1990, Role of the Retinoblastoma Gene in the Initiation and Progression of Human Cancer, *J. Clin. Invest.* 85:988–993.

Benoist et al., 1981, In vivo sequence requirements of the SV40 early promoter region, *Nature* 290:304–310.

Bookstein et al., 1991, Molecular Genetics of the Retinoblastoma Suppressor Gene, *Crit. Rev. Oncog.* 2(3):211–227.

Bookstein et al, 1990, Suppression of Tumorigenicity of Human Prostate Carcinoma Cells by Replacing a Mutated RB Gene, *Science* 247:712–715.

Brinster et al., 1982, Regulation of metallothionein–thymidine kinase fusion plasmids injected into mouse eggs, *Nature* 296:39–42.2.

Brown et al., 1984, Mechanism of activation of an N–ras gene in the human fibrosarcoma cell line HT1080, *EMBO J.* 3(6):1321–1326.

Buchkovich et al., 1989, The Retinoblastoma Protein is Phosphorylated during Specific Phases of the Cell Cycle, *Cell* 58:1097–1105.

Ceccoli et al., 1989, Encapsulation of the UV–DNA Repair Enzyme T4 Endocuclease V in Liposomes and Delivery to Human Cells, *Journal of Investigative Dermatology* 93:190–194.

Chen et al., 1989, Phosphorylation of the Retinoblastoma Gene Product is Modulated during the Cell Cycle and Cellular Differentiation, *Cell* 58:1193–1198.

Culver et al., 1992, In Vivo Gene Transfer with Retroviral Vector–Producer Cells for Treatment of Experimental Brain Tumors, *Science* 256:1550–1552.

Culver et al., 1991, Lymphocyte Gene Therapy, *Human Gene Therapy* 2:107–109.

(List continued on next page.)

*Primary Examiner*—Brian R. Stanton
*Attorney, Agent, or Firm*—Pennie & Edmonds LLP

[57] ABSTRACT

The present invention relates to a broad-spectrum tumor suppressor gene and the protein expressed by that gene in appropriate host cells. The protein is a second in-frame AUG codon-initiated retinoblasoma protein of about 94 kD relative molecular mass. The present invention also relates to methods of treating a mammal having a disease or disorder characterized by abnormal cellular proliferation, such as a tumor or cancer and methods of treating abnormally proliferating cells, such as tumor or cancer cells. Treatment is accomplished by inserting a host cell compatible p94$^{RB}$ expression vector or an effective amount of p94$^{RB}$ protein into a cell or cells in need of treatment.

27 Claims, 21 Drawing Sheets

OTHER PUBLICATIONS

Curiel et al., 1991, Adenovirus enhancement of transferrin–polylysine–mediated gene delivery, *Proc. Natl. Acad. Sci. USA* 88:8850–8854.

Davies, 1992, Moving stright to the target, *Nature genetics* 358:519.

DeCaprio et al., 1989, The Product of the Retinoblastoma Susceptibility Gene Has Properties of a Cell Cycle Regulatory Element, *Cell* 58:1085–1095.

Diller et al., 1990, p53 Functions as a Cell Cycle Control Protein in Osteosarcomas, *Molecular and Cellular Biology* 10(11):5772–5781.

Durst et al., 1987, Papillomavirus sequences integrate near cellular oncogenes in some cervical carcinomas, *Proc. Natl. Acad. Sci. USA* 84(4):1070–1074.

Fearon et al., 1990, A Genetic Model for Colorectal Tumorigenesis, *Cell* 61:759–767.

Francois et al., Mar./Apr., The Costenbader Memorial Lecture Genesis and Genetics of Retinoblastoma, *Journal of Pediatric Ophthalmology and Strabismus* 16(2):85–100.

Friend et al., 1987, Deletions of a DNA sequence in retinoblastomas and mesenchymal tumors: Organization of the sequence and its encoded protein, *Proc. Natl. Acad. Sci. USA* 84:9059–9063.

Furukawa et al., 1990, Expression and state of phosphorylation of the retinoblastoma susceptibility gene product in cycling and noncycling human hematopoietic cells, *P.N.A.S. USA* 87:2770–2774.

Gallie et al, 1991, The Genetics of Retinoblastoma: Relevance to the Patient, *Pediatric Clinics of North America* 38(2):299–315.

Gallie et al., 1992, How do Retinoblastoma Tumours Form?, *Eye* 6:226–231.

Goodrich et al., 1992, Abrogation by c–myc of G1 phase arrest induced by RB protein but not by p53, *Nature* 360:177–179.

Goodrich et al., 1992, Expression of the Retinoblastoma Gene Product in Bladder carcinoma Cells Associates with a Low Frequency of Tumor Formation, *Cancer Research* 52:1968–1973.

Gunning et al., 1987, A human β–actin expression vector system directs high–level accumulation of antisense transcripts, *Proc. Natl. Acad. Sci. USA* 84:4831–4835.

Hamel et al., 1992, Transcriptional Repression of the E2–Containing Promoters EllaE, c–myc, and RB1 by the Product of the RB1 Gene, *Molecular and Cellular Biology* 12(8):3431–3438.

Huang et al.,1988, Suppression of the Neoplastic Phenotype by Replacement of the RB Gene in Human Cancer Cells, *Science reports* 242:1563–1566.

Jaffe et al., 1992, Adenovirus–mediated in vivo gene transfer and expression in normal rat liver, *Nature genetics* 1:372–378.

Karasuyama et al., 1989, Autocrine Growth and Tumorigenicity of Interleukin 2–Dependent Helper T Cells Transfected with IL–2 Gene, *J. Exp. Med.* 169:13.

Klessig et al., 1984, Introduction, Stable Integration, and Controlled Expression of a Chimeric Adenoirus Gene Whose Product Is Toxic to the Recipient Human Cell, *Mol. Cell Biol.* 4:1354–1362.

Knight et al., 1988, Antiviral Therapy with Small Particle Aerosols, *European Journal of Clinical Microbiology and Infectious Diseases* 7(6):721–731.

Kratzke et al., 1992,Functional Analysis at the Cys–706 Residue of the Retinoblastoma Protein, *The Journal of Biological Chemistry* 267(36):25998–26003.

Kutty et al., 1992, Heme oxygenase: expression in human retina and modulation by stress agents in a human retinoblastoma cell model system, *Oxford University Press* 11(2):153–160.

Lee et al., 1990, Molecular biology of the Human Retinoblastoma Gene, *Immunol Ser.* 51:169–200.

Lee et al., 1987, The retinoblastoma susceptibility gene encodes a nuclear phosphoprotein associated with DNA binding activity, *Nature* 329:642–645.

Lemarchand et al., 1992, Adenovirus–mediated transfer of a recombinant human alpha$_1$–antitrypsin cDNA to human endothelial cells, *P.N.A.S. USA* 89:6482–6486.

Lin et al., 1992, Nasopharyngeal Carcinoma and Retinoblastoma Gene Expression, *Laboratory Investigation* 67(1):56–70.

Ludlow et al., 1989, SV40 Large T Antigen Binds Preferentially to an Underphosphorylated Member of the Retinoblastoma Susceptibility Gene Product Family, *Cell* 56:57–65.

Lynch et al., 1991, Production of High–Titer Helper Virus––Free Retroviral Vectors by Cocultivation of Packaging Cells with Different Host Ranges, *J. Virol.* 65:3887–3890.

Maniatis et al., 1989, *Molecular Cloning: A Laboratory Manual,* Cold Spring Harbor Laboratory, Cold Spring Harbor, New York.

Mannino et al., 1988,Liposome Mediated Gene Transfer, *Biotechniques* 6(7):682–690.

Marshall, 1991, Tumor Suppressor Genes, *Cell* 64:313–326.

McGee et al., 1989, Structure and partial genomic sequence of the human retinoblastoma susceptibility gene, *Gene* 80:119–128.

Mihara et al., 1989, Cell Cycle–Dependent regulation of Phosphorylation of the Human Retinoblastoma Gene Product, *Science* 246:1300–1303.

Miller, 1992, Human gene therapy comes of age, *Nature* 357:455–460.

Miller et al., 1986, Redesign of Retrovirus Packaging Cell Lines to Avoid Recombination Leading to Helper Virus Production, *Molec. Cell Biol.* 6(8):2895–2902.

Miller et al., 1985, Generation of Helper–Free Amphotropic Retroviruses That Transduce a Dominant–Acting, Methotrexate–Resistant Dihydrofolate Reductase Gene, *Molec. Cell Biol.* 5(3):431–437.

Miyanohara et al., 1988, Efficient expression of retroviral vector–transduced human low density lipoprotein (LDL) receptor in LDL receptor–deficient rabbit fibroblasts in vitro, *Proc. Natl. Acad. Sci. USA* 85:6538–6542.

Murakami et al., 1991, Inactivation of the retinoblastoma gene in a human lung carcinoma cell line detected by single–strand conformation polymorphism analysis of the polymerase chain reaction product of cDNA, *Oncogene* 6:37–42.

Nabel et al., 1990, Site–Specific Gene Expression in Vivo by Direct Gene Transfer into the Arterial Wall, *Science* 249:1285–1288.

Newton et al., 1988, Vesicle–to–Cell Protein Transfer: Insertion of Band 3, the Erythrocyte Anion Transporter, into Lymphoid Cells, *Biochemistry* 27:4655–4659.

Riele et al., 1992, Highly efficient gene targeting in embryonic stem cells through homologous recombination with isogenic DNA constructs, *P.N.A.S. USA* 89:5128–5132.

Rosenfeld et al., 1992, In Vivo Transfer of the Human Cystic Fibrosis Transmembrane Conductance Regulator Gene to the Airway Epithelium, *Cell* 68:143–155.

Schier, 1992, Conversations: Gene Therapy, *The Cancer Bulletin* 44(3)167.

Shew et al., 1990, C–terminal truncation of the retinoblastoma gene product leads to functional inactivation, *P.N.A.S. USA* 87:6–10.

Shew et al., 1989, Antibodies Detecting Abnormalities of the Retinoblastoma Susceptibility Gene Product (pp110–RB) in Osteosarcomas and Synovial Sarcomas, *Ocogene Research* 1:205–214.

Stein et al., 1990, Failure to Phosphorylate the Retinoblastoma Gene Product in Senescent Human Fibroblasts, *Science* 249:666–669.

Stone, 1992, Molecular 'Surgery' for Brain Tumors, *Science* 256:1513.

Sugawara et al., 1991, Distribution of c–yes–1 gene product in various cells and tissues, *Br. J. Cancer* 63(4):508–513.

Takahashi et al., 1991, The retinoblastoma gene functions as a growth and tumor suppressor in human bladder carcinoma cells, *Proc. Natl. Acad. Sci. USA* 88:5257–5261.

Tanswell et al., 1990, Response of fetal rat lung fibroblasts to elevated oxygen concentrations after liposome–mediated augmentation of antioxidant enzymes, *Biochimica et Biophysica Acta* 1044:269–274.

Templeton et al., 1991, Nonfunctional mutants of the retinoblastoma protein are characterized by defects in phosphorylation, viral oncoprotein association, and nuclear tethering, *Proc. Natl. Acad. Sci. USA* 88:3033–3037.

Thompson, 1992, Stem–Cell Gene Therapy Moves Toward Approval, *Science* 255:1072.

Uzvolgyi et al., 1991, Reintroduction of a Normal Retinoblastoma Gene into Retinoblastoma and Osteosarcoma Cells Inhibits the Replication associated Function of SV40 Large T Antigen, *Cell Growth & Differentiation* 2:297–303.

Wagner et al., 1981, Nucleotide sequence of the thymidine kinase gene of herpes simplex virus type 1, *Proc. Natl. Acad. Sci. USA* 78(3):1441–1445.

Weinberg, 1991, Tumor Suppressor Genes, *Science articles* 254:1138–1146.

Weinberg, 1989, Oncogenes, Antioncogenes, and the Molecular Bases of Multistep Carcinogenesis, *Cancer Research* 49:3713–3721.

Weiss et al., 1985, *RNA Tumor Viruses*, Cold Spring Harbor, New York.

Whyte et al., 1988, Association between an oncogene and an anti–oncogene: the adenovirus E1A proteins bind to the retinoblastoma gene product, *Nature* 334:124–129.

Wolfe et al., 1992, Herpesvirus vector gene transfer and express of β–glucuronidase in the central nervous system of MPS VII mice, *Nature Genetics* 1:379–384.

Wu et al., 1991, Receptor–mediated Gene Delivery in Vivo: Partial Correction of Genetic Analbuminemia in Nagase Rats, *J. Biol. Chem.* 266:14338–14342.

Xu et al.,1991, Intraocular Tumor formation of RB Reconstituted reinoblastoma Cells, *Cancer Research* 51:4481–4485.

Xu et al., 1991, Lack of nuclear RB protein staining in G0/middle G1 cells: correlation to changes in total RB protein level, *Oncogene* 6:1139–1146.

Xu et al., 1989, The retinoblastoma susceptibility gene product: a characteristic pattern in normal cells and abnormal expression in malignant cells, *Oncogene* 4:807–812.

Yamada et al., 1985, Overproduction of the protein product of a nonselected foreign gene carried by an adenovirus vector, *Proc. Natl. Acad. Sci. USA* 82(11):3567–71.

Yamamoto et al., 1980, Identification of a Functional Promoter in the Long Terminal Repeat of Rous Sarcoma Virus, *Cell* 22:787–797.

Yokota et al., 1988, Altered expression of the retinoblastoma (RB) gene in small–cell carcinoma of the lung, *Oncogene* 3:471–475.

Zhou et al., 1993, Characterization of RB+ clones of RB reconstituted retinoblastoma and osteosarcoma cells, *Proc. Am. Assoc. Cancer Res.* 34:538 abstract No. 3214.

Orkly, S. et al (1995) Report and Recommendation of the Panel to Asses the L Investment: Research in Gene Therapy.

Mulligan, R. (1993). Science 260, 926–932.

Marshall, E. (1995). Science 269, 1050–55.

Culver, K. (1994). Trends in Genetics 10, 174–78.

Weinberg, R. (1995). Cell 81, 323–330.

Goodrich, D. et al (1993). Biochimica and Biophysica Acta 1155, 43–61.

```
      10         20         30         40         50         60
5' GATCCCGACC TAGATGAGAT GTCGTTCACT TTTACTGAGC TACAGAAAAA CATAGAAATC
3'    GGCTGG ATCTACTCTA CAGCAAGTGA AAATGACTCG ATGTCTTTTT GTATCTTTAG
                         70         80         90        100        110        120

AGTGTCCATA AATTCTTTAA CTTACTAAAA GAAATTGATA CCAGTACCAA AGTTGATAAT
   TCACAGGTAT TTAAGAAATT GAATGATTTT CTTTAACTAT GGTCATGGTT TCAACTATTA
                        130        140        150        160        170        180

GCTATGTCAA GACTGTTGAA GAAGTATGAT GTATTGTTTG CACTCTTCAG CAAATTGGAA
   CGATACAGTT CTGACAACTT CTTCATACTA CATAACAAAC GTGAGAAGTC GTTTAACCTT
                        190        200        210        220        230        240

AGGACATGTG AACTATATA TTTGACACAA CCCAGCAGTT CGATATCTAC TGAAATAAAT
   TCCTGTACAC TTGAATATAT AAACTGTGTT GGGTCGTCAA GCTATAGATG ACTTTATTTA
                        250        260        270        280        290        300

TCTGCATTGG TGCTAAAAGT TTCTTGGATC ACATTTTTAT TAGCTAAAGG GGAAGTATTA
   AGACGTAACC ACGATTTCA AAGAACCTAG TGTAAAAATA ATCGATTTCC CCTTCATAAT
                        310        320        330        340        350        360

CAAATGGAAG ATGATCTGGT GTTGCTCAAA GATTTCATTT CAGTTAATGC TATGTGTCCT TGACTATTTT
   GTTTACCTTC TACTAGACCA CAACGAGTTT CTAAAGTAAA GTCAATTACG ATACACAGGA ACTGATAAAA
                        370        380        390        400        410        420

ATTAAACTCT CACCTCCCAT GTTGCTCAAA GAACCATATA AAACAGCTGT TATACCCATT
   TAATTTGAGA GTGGAGGGTA CAACGAGTTT CTTGGTATAT TTTGTCGACA ATATGGGTAA
                        430        440        450        460        470        480

AATGGTTCAC CTCGAACACC CAGGCGAGGT CAGAACAGGA GTGCACGGAT AGCAAAACAA
   TTACCAAGTG GAGCTTGTGG GTCCGCTCCA GTCTTGTCCT CACGTGCCTA TCGTTTTGTT
                        490        500        510        520        530        540

CTAGAAAATG ATACAAGAAT TATTGAAGTT CTCTGTAAAG AACATGAATG TAATATAGAT
   GATCTTTTAC TATGTTCTTA ATAACTTCAA GAGACATTTC TTGTACTTAC ATTATATCTA
```

FIG. 1A

```
 550 GAGGTGAAAA  560 ATGTTTATTT  570 CAAAAATTTT  580 ATACCTTTTA  590 TGAATTCTCT  600 TGGACTTGTA
 610 CTCCACTTTT  620 TACAAATAAA  630 GTTTTTAAAA  640 TATGGAAAAT  650 ACTTAAGAGA  660 ACCTGAACAT
 670 ACATCTAATG  680 GACTTCCAGA  690 GGTTGAAAAT  700 CTTTCTAAAC  710 GATACGAAGA  720 AATTTATCTT
 730 TGTAGATTAC  740 CTGAAGGTCT  750 CCAACTTTTA  760 GAAAGATTTG  770 CTATGCTTCT  780 TTAAATAGAA
 790 AAAAATAAAG  800 ATCTAGATGC  810 AAGATTATTT  820 TTGGATCATG  830 ATAAAACTCT  840 TCAGACTGAT
 850 TTTTATTTC   860 TAGATCTACG  870 TTCTAATAAA  880 AACCTAGTAC  890 TATTTTGAGA  900 AGTCTGACTA
 910 TCTATAGACA  920 GTTTTGAAAC  930 ACAGAGAACA  940 CCACGAAAAA  950 GTAACCTTGA  960 TGAAGAGGTG
 970 AGATATCTGT  980 CAAAACTTTG  990 TGTCTCTTGT 1000 GGTGCTTTTT 1010 CATTGGAACT 1020 ACTTCTCCAC
1030 AATGTAATTC 1040 CTCCACACAC 1050 TCCAGTTAGG 1060 ACTGTTATGA 1070 ACACTATCCA 1080 ACAATTAATG
1090 TTACATTAAG 1100 GAGGTGTGTG 1110 AGGTCAATCC 1120 TGACAATACT 1130 TGTGATAGGT 1140 TGTTAATTAC
1150 ATGATTTAA  1160 ATTCAGCAAG 1170 TGATCAACCT 1180 TCAGAAAATC 1190 TGATTTCCTA 1200 TTTTAACAAC
1210 TACTAAAATT 1220 TAAGTCGTTC 1230 ACTAGTTGGA 1240 AGTCTTTTAG 1250 ACTAAAGGAT 1260 AAAATTGTTG
1270 TGCACAGTGA 1280 ATCCAAAAGA 1290 AAGTATACTG 1300 AAAAGAGTGA 1310 AGGATATAGG 1320 ATACATCTTT
1330 ACGTGTCACT 1340 TAGGTTTTCT 1350 TTCATATGAC 1360 TTTCTCACT  1370 TCCTATATCC 1380 TATGTAGAAA
1390 AAAGAGAAAT 1400 TTGCTAAAGC 1410 TGTGGGACAG 1420 GGTTGTGTCG 1430 AAATTGGATC 1440 ACAGCGATAC
1450 TTTCTCTTTA 1460 AACGATTTCG 1470 ACACCCTGTC 1480 CCAACACAGC 1490 TTTAACCTAG 1500 TGTCGCTATG
1510 AAACTTGGAG 1520 TTCGCTTGTA 1530 TTACCGAGTA 1540 ATGGAATCCA 1550 TGCTTAAATC 1560 AGAAGAAGAA
1570 TTTGAACCTC 1580 AAGCGAACAT 1590 AATGGCTCAT 1600 TACCTTAGGT 1610 ACGAATTTAG 1620 TCTTCTTCTT
```

FIG. 1B

FIG. 1C

```
       1090       1100       1110       1120       1130       1140
 CGATTATCCA TTCAAAATTT TAGCAAACTT CTGAATGACA ACATTTTCA  TATGTCTTTA
 GCTAATAGGT AAGTTTTAAA ATCGTTTGAA GACTTACTGT TGTAAAAAGT ATACAGAAAT
       1150       1160       1170       1180       1190       1200
 TTGGCGTGCG CTCTTGAGGT TGTAATGGCC ACATATAGCA GAAGTACATC TCAGAATCTT
 AACCGCACGC GAGAACTCCA ACATTACCGG TGTATATCGT CTTCATGTAG AGTCTTAGAA
       1210       1220       1230       1240       1250       1260
 GATTCTGGAA CAGATTTGTC TTTCCCATGG ATTCTGAATG TGCTTAATTT AAAAGCCTTT
 CTAAGACCTT GTCTAAACAG AAAGGGTACC TAAGACTTAC ACGAATTAAA TTTTCGGAAA
       1270       1280       1290       1300       1310       1320
 GATTTTTACA AAGTGATCGA AAGTTTTATC AAAGCAGAAG GCAACTTGAC AAGAGAAATG
 CTAAAAATGT TTCACTAGCT TTCAAAATAG TTTCGTCTTC CGTTGAACTG TTCTCTTTAC
       1330       1340       1350       1360       1370       1380
 ATAAAACATT TAGAACGATG TGAACATCGA ATCATGGAAT CCCTTGCATG GCTCTCAGAT
 TATTTTGTAA ATCTTGCTAC ACTTGTAGCT TAGTACCTTA GGGAACGTAC CGAGAGTCTA
       1390       1400       1410       1420       1430       1440
 TCACCTTTAT TTGATCTTAT TAAACAATCA AAGGACCGAG AAGGACCAAC TGATCACCTT
 AGTGGAAATA AACTAGAATA ATTTGTTAGT TTCCTGGCTC TTCCTGGTTG ACTAGTGGAA
       1450       1460       1470       1480       1490       1500
 GAATCTGCTT GTCCTCTTAA TCTTCCTCTC CAGAATAATC ACACTGCAGC AGATATGTAT
 CTTAGACGAA CAGGAGAATT AGAAGGAGAG GTCTTATTAG TGTGACGTCG TCTATACATA
       1510       1520       1530       1540       1550       1560
 CTTTCCCTG TAAGATCTCC AAAGAAAAAA GGTTCAACTA CGCGTGTAAA TTCTACTGCA
 GAAAGGGAC ATTCTAGAGG TTTCTTTTTT CCAAGTTGAT GCGCACATTT AAGATGACGT
       1570       1580       1590       1600       1610       1620
 AATGCAGAGA CACAAGCAAC CTCAGCCTTC CAGACCCAGA AGCCATTGAA ATCTACCTCT
 TTACGTCTCT GTGTTCGTTG GAGTCGGAAG GTCTGGGTCT TCGGTAACTT TAGATGGAGA
```

```
     1630       1640       1650       1660       1670       1680
CTTTCACTGT TTTATAAAAA AGTGTATCGG CTAGCCTATC TCCGGCTAAA TACACTTTGT
GAAAGTGACA AAATATTTTT TCACATAGCC GATCGGATAG AGGCCGATTT ATGTGAAACA
     1690       1700       1710       1720       1730       1740
GAACGCCTTC TGTCTGAGCA CCCAGAATTA GAACATATCA TCTGGACCCT TTTCCAGCAC
CTTGCGGAAG ACAGACTCGT GGGTCTTAAT CTTGTATAGT AGACCTGGGA AAAGGTCGTG
     1750       1760       1770       1780       1790       1800
ACCCTGCAGA ATGAGTATGA ACTCATGAGA GACAGGCATT TGGACCAAAT TATGATGTGT
TGGGACGTCT TACTCATACT TGAGTACTCT CTGTCCGTAA ACCTGGTTTA ATACTACACA
     1810       1820       1830       1840       1850       1860
TCCATGTATG GCATATGCAA AGTGAAGAAT ATAGACCTTA AATTCAAAAT CATTGTAACA
AGGTACATAC CGTATACGTT TCACTTCTTA TATCTGGAAT TTAAGTTTTA GTAACATTGT
     1870       1880       1890       1900       1910       1920
GCATACAAGG ATCTTCCTCA TGCTGTTCAG GAGACATTCA AACGTGTTTT GATCAAAGAA
CGTATGTTCC TAGAAGGAGT ACGACAAGTC CTCTGTAAGT TTGCACAAAA CTAGTTTCTT
     1930       1940       1950       1960       1970       1980
GAGGAGTATG ATTCTATTAT AGTATTCTAT AACTCGGTCT TCATGCAGAG ACTGAAAACA
CTCCTCATAC TAAGATAATA TCATAAGATA TTGAGCCAGA AGTACGTCTC TGACTTTTGT
     1990       2000       2010       2020       2030       2040
AATATTTTGC AGTATGCTTC CACCAGGCCC CCTACCTTGT CACCAATACC TCACATTCCT
TTATAAAACG TCATACGAAG GTGGTCCGGG GGATGGAACA GTGGTTATGG AGTGTAAGGA
     2050       2060       2070       2080       2090       2100
CGAAGCCCTT ACAAGTTTCC TAGTTCACCC TTACGGATTC CTGGAGGGAA CATCTATATT
GCTTCGGGAA TGTTCAAAGG ATCAAGTGGG AATGCCTAAG GACCTCCCTT GTAGATATAA
     2110       2120       2130       2140       2150       2160
TCACCCCTGA AGAGTCCATA TAAAATTTCA GAAGGTCTGC CAACACCAAC AAAAATGACT
AGTGGGGACT TCTCAGGTAT ATTTTAAAGT CTTCCAGACG GTTGTGGTTG TTTTTACTGA
```

FIG. 1D

```
        2170       2180       2190       2200       2210       2220
CCAAGATCAA GAATCTTAGT ATCAATTGGT GAATCATTCG GGACTTCTGA GAAGTTCCAG
GGTTCTAGTT CTTAGAATCA TAGTTAACCA CTTAGTAAGC CCTGAAGACT CTTCAAGGTC
        2230       2240       2250       2260       2270       2280
AAAATAAATC AGATGGTATG TAACAGCGAC CGTGTGCTCA AAAGAAGTGC TGAAGGAAGC
TTTTATTTAG TCTACCATAC ATTGTCGCTG GCACACGAGT TTTCTTCACG ACTTCCTTCG
        2290       2300       2310       2320       2330       2340
AACCCTCCTA AAAACTGAA TTTGATATTG AAGGATCAGA TGAAGCAGA
TTGGGAGGAT TTGGTGACTT TTTTGATGCG AAACTATAAC TTCCTAGTCT ACTTCGTCTA
        2350       2360       2370       2380       2390       2400
GGAAGTAAAC ATCTCCCAGG AGAGTCCAAA TTTCAGCAGA AACTGGCAGA AATGACTTCT
CCTTCATTTG TAGAGGGTCC TCTCAGGTTT AAAGTCGTCT TTGACCGTCT TTACTGAAGA
        2410       2420       2430       2440       2450       2460
ACTCGAACAC GAATGCAAAA GCAGAAAATG AATGATAGCA TGGATACCTC AAACAAGGAA
TGAGCTTGTG CTTACGTTTT CGTCTTTTAC TTACTATCGT ACCTATGGAG TTTGTTCCTT
        2470       2480       2490       2500       2510       2520
GAGAAATGAG GATCTCAGGA CCTTGGTGGA CACTGTGTAC ACCTCTGGAT TCATTGTCTC
CTCTTTACTC CTAGAGTCCT GGAACCACCT GTGACACATG TGGAGACCTA AGTAACAGAG
        2530       2540       2550       2560       2570       2580
TCACAGATGT GACTGTATAA CTTTCCCAGG TTCTGTTTAT GGCCACATTT AATATCTTCA
AGTGTCTACA CTGACATATT GAAAGGGTCC AAGACAAATA CCGGTGTAAA TTATAGAAGT
        2590       2600       2610       2620       2630       2640
GCTCTTTTTG TGGATATAAA ATGTGCAGAT GCAATTGTTT GGGTGATTCC TAAGCCACTT
CGAGAAAAAC ACCTATATTT TACACGTCTA CGTTAACAAA CCCACTAAGG ATTCGGTGAA
        2650       2660       2670       2680       2690       2700
GAAATGTTAG TCATTGTTAT TTATACAAGA TTGAAAATCT TGTGTAAATC CTGCCATTA
CTTTACAATC AGTAACAATA AATATGTTCT AACTTTTAGA ACACATTTAG GACGGTAAAT
```

FIG. 1E

```
2710        2720        2730        2740        2750        2760
AAAAGTTGTA  GCAGATTGTT  TCCTCTTCCA  AAGTAAAATT  GCTGTGCTTT  ATGGATAGTA
TTTTCAACAT  CGTCTAACAA  AGGAGAAGGT  TTCATTTTAA  CGACACGAAA  TACCTATCAT
        2770        2780        2790        2800        2810        2820
AGAATGGCCC  TAGAGTGGGA  GTCCTGATAA  CCCAGGCCTG  TCTGACTACT  TTGCCTTCTT
TCTTACCGGG  ATCTCACCCT  CAGGACTATT  GGGTCCGGAC  AGACTGATGA  AACGGAAGAA
        2830        2840        2850        2860        2870        2880
TTGTAGCATA  TAGGTGATGT  TTGCTCTTGT  TTTTATTAAT  TTATATGTAT  ATTTTTTAA
AACATCGTAT  ATCCACTACA  AACGAGAACA  AAAATAATTA  AATATACATA  TAAAAAATT
        2890        2900        2910        2920        2930        2940
TTTAACATGA  ACACCCTTAG  AAAATGTGTC  CTATCTATCT  TCCAAATGCA  ATTGATTGA
AAATTGTACT  TGTGGGAATC  TTTACACAG   GATAGATAGA  AGGTTTACGT  TAAACTAACT
        2950        2960        2970        2980        2990        3000
CTGCCCATTC  ACCAAAATTA  TCCTGAACTC  TTCTGCAAAA  ATGGATATTA  TTAGAAATTA
GACGGGTAAG  TGGTTTTAAT  AGGACTTGAG  AAGACGTTTT  TACCTATAAT  AATCTTTAAT
        3010        3020        3030        3040        3050        3060
GAAAAAATT   ACTAATTTTA  CACATTAGAT  TTTATTTTAC  TATTGGAAATC TGATATACTG
CTTTTTTAA   TGATTAAAAT  GTGTAATCTA  ATAAAAATG   ATAACCTTAG  ACTATATGAC
        3070        3080        3090        3100        3110        3120
TGTGCTTGTT  TTATAAAATT  TTGCTTTTAA  TTAAATAAAA  GCTGGAAGCA  AAGTATAACC
ACACGAACAA  AATATTTTAA  AACGAAAATT  AATTTATTTT  CGACCTTCGT  TTCATATTGG
        3130        3140        3150        3160        3170        3180
ATATGATACT  ATCATACTAC  TGAAACAGAT  TTCATACCTC  AGAATGTAAA  AGAACTTACT
TATACTATGA  TAGTATGATG  ACTTTGTCTA  AAGTATGGAG  TCTTACATTT  TCTTGAATGA
        3190        3200        3210        3220        3230
GATTATTTTC  TTCATCCAAC  TTATGTTTTT  AAATGAGGAT  TATTGATAGT    GG    3'
CTAATAAAAG  AAGTAGGTTG  AATACAAAAA  TTTACTCCTA  ATAACTATCA    CCCTAG 5'
```

FIG. 1F

```
GATCCCGA CCTAGATGAG ATG TCG TTC ACT TTT ACT GAG CTA CAG AAA            48
                    Met Ser Phe Thr Phe Thr Glu Leu Gln Lys            10

AAC ATA GAA ATC AGT GTC CAT AAA TTC TTT AAC TTA CTA AAA GAA ATT        96
Asn Ile Glu Ile Ser Val His Lys Phe Phe Asn Leu Leu Lys Glu Ile        26

GAT ACC AGT ACC AAA GTT GAT AAT GCT ATG TCA AGA CTG TTG AAG AAG       144
Asp Thr Ser Thr Lys Val Asp Asn Ala Met Ser Arg Leu Leu Lys Lys        42

TAT GAT GTA TTG TTT GCA CTC TTC AGC AAA TTG GAA AGG ACA TGT GAA       192
Tyr Asp Val Leu Phe Ala Leu Phe Ser Lys Leu Glu Arg Thr Cys Glu        58

CTT ATA TAT TTG ACA CAA CCC AGC AGT TCG ATC TCT ACT GAA ATA AAT       240
Leu Ile Tyr Leu Thr Gln Pro Ser Ser Ser Ile Ser Thr Glu Ile Asn        74

TCT GCA TTG GTG CTA AAA GTT TCT TGG ATC ACA TTT TTA TTA GCT AAA       288
Ser Ala Leu Val Leu Lys Val Ser Trp Ile Thr Phe Leu Leu Ala Lys        90

GGG GAA GTA TTA CAA ATG GAA GAT GAT CTG GTG ATT TCA TTT CAG TTA       336
Gly Glu Val Leu Gln Met Glu Asp Asp Leu Val Ile Ser Phe Gln Leu       106

ATG CTA TGT GTC CTT GAC TAT TTT ATT AAA CTC TCA CCT CCC ATG TTG       384
Met Leu Cys Val Leu Asp Tyr Phe Ile Lys Leu Ser Pro Pro Met Leu       122

CTC AAA GAA CCA TAT AAA ACA GCT GTT ATA CCC ATT AAT GGT TCA CCT       432
Leu Lys Glu Pro Tyr Lys Thr Ala Val Ile Pro Ile Asn Gly Ser Pro       138

CGA ACA CCC AGG CGA AAC AGG AGT GCA CGG ATA GCA AAA CAA               480
Arg Thr Pro Arg Arg Asn Arg Ser Ala Arg Ile Ala Lys Gln               154
```

FIG. 2A

```
CTA GAA AAT GAT ACA AGA ATT ATT GAA GTT CTC TGT AAA GAA CAT GAA    528
Leu Glu Asn Asp Thr Arg Ile Ile Glu Val Leu Cys Lys Glu His Glu    170

TGT AAT ATA GAT GAG GTG AAA AAT GTT TAT TTC AAA AAT TTT ATA CCT    576
Cys Asn Ile Asp Glu Val Lys Asn Val Tyr Phe Lys Asn Phe Ile Pro    186

TTT ATG AAT TCT CTT GGA CTT GTA ACA TCT AAT GGA CTT CCA GAG GTT    624
Phe Met Asn Ser Leu Gly Leu Val Thr Ser Asn Gly Leu Pro Glu Val    202

GAA AAT CTT TCT AAA CGA TAC GAA GAA ATT TAT CTT AAA AAT AAA GAT    672
Glu Asn Leu Ser Lys Arg Tyr Glu Glu Ile Tyr Leu Lys Asn Lys Asp    218

CTA GAT GCA AGA TTA TTT GAT CAT GAT AAA ACT CTT CAG ACT GAT    720
Leu Asp Ala Arg Leu Phe Asp His Asp Lys Thr Leu Gln Thr Asp    234

TCT ATA GAC AGT TTT GAA ACA CAG AGA ACA CCA CGA AAA AGT AAC CTT    768
Ser Ile Asp Ser Phe Glu Thr Gln Arg Thr Pro Arg Lys Ser Asn Leu    250

GAT GAA GAG GTG AAT GTA ATT CCT CCA CAC ACT CCA GTT AGG ACT GTT    816
Asp Glu Glu Val Asn Val Ile Pro Pro His Thr Pro Val Arg Thr Val    266

ATG AAC ACT ATC CAA CAA TTA ATG ATG ATT TTA AAT TCA GCA AGT GAT    864
Met Asn Thr Ile Gln Gln Leu Met Met Ile Leu Asn Ser Ala Ser Asp    282

CAA CCT TCA GAA AAT CTG ATT TCC TAT TTT AAC AAC TGC ACA GTG AAT    912
Gln Pro Ser Glu Asn Leu Ile Ser Tyr Phe Asn Asn Cys Thr Val Asn    298

CCA AAA GAA AGT ATA CTG AAA AGA GTG AAG GAT ATA GGA TAC ATC TTT    960
Pro Lys Glu Ser Ile Leu Lys Arg Val Lys Asp Ile Gly Tyr Ile Phe    314
```

FIG. 2B

```
AAA GAG AAA TTT GCT AAA GCT GTG GGA CAG GGT TGT GTC GAA ATT GGA  1008
Lys Glu Lys Phe Ala Lys Ala Val Gly Gln Gly Cys Val Glu Ile Gly   330

TCA CAG CGA TAC AAA CTT GGA GTT TAT CGA TTG TAC CGA ATG GAA      1056
Ser Gln Arg Tyr Lys Leu Gly Val Tyr Arg Leu Tyr Arg Val Met Glu   346

TCC ATG CTT AAA TCA GAA GAA CGA ATT CAA TCC ATT CAA AAT TTT AGC  1104
Ser Met Leu Lys Ser Glu Glu Arg Ile Gln Ser Ile Gln Asn Phe Ser   362

AAA CTT CTG AAT GAC AAC ATT TTT CAT ATG TCT TTA TTG GCG TGC GCT  1152
Lys Leu Leu Asn Asp Asn Ile Phe His Met Ser Leu Leu Ala Cys Ala   378

CTT GAG GTT GTA ATG GCC ACA TAT AGC AGA AGT ACA TCT CAG AAT CTT  1200
Leu Glu Val Val Met Ala Thr Tyr Ser Arg Ser Thr Ser Gln Asn Leu   394

GAT TCT GGA ACA GAT TTG TCT TTC CCA TGG ATT CTG AAT GTG CTT AAT  1248
Asp Ser Gly Thr Asp Leu Ser Phe Pro Trp Ile Leu Asn Val Leu Asn   410

TTA AAA GCC TTT GAT TTT TAC AAA GTG ATC ATA AAA GAA AGT TTT ATC AAA GCA  1296
Leu Lys Ala Phe Asp Phe Tyr Lys Val Ile Ile Lys Glu Ser Phe Ile Lys Ala   426

GAA GGC AAC TTG ACA AGA GAA ATG ATA AAA CAT TTA GAA CGA TGT GAA  1344
Glu Gly Asn Leu Thr Arg Glu Met Ile Lys His Leu Glu Arg Cys Glu   442

CAT CGA ATC ATG GAA TCC CTT GCA TGG CTC TCA GAT TCA CCT TTA TTT  1392
His Arg Ile Met Glu Ser Leu Ala Trp Leu Ser Asp Ser Pro Leu Phe   458

GAT CTT ATT AAA CAA TCA GGA GAC CGA GAA CCA ACT GAT CAC CTT     1440
Asp Leu Ile Lys Gln Ser Lys Asp Arg Glu Gly Pro Thr Asp His Leu   474
```

FIG. 2C

```
GAA TCT GCT TGT CCT CTT AAT CTT CCT CTC CAG AAT AAT CAC ACT GCA  1488
Glu Ser Ala Cys Pro Leu Asn Leu Pro Leu Gln Asn Asn His Thr Ala   490

GCA GAT ATG TAT CTT TCT CCT GTA AGA TCT CCA AAG AAA GGT TCA  1536
Ala Asp Met Tyr Leu Ser Pro Val Arg Ser Pro Lys Lys Gly Ser   506

ACT ACG CGT GTA AAT TCT ACT GCA AAT GCA GAG ACA CAA GCA ACC TCA  1584
Thr Thr Arg Val Asn Ser Thr Ala Asn Ala Glu Thr Gln Ala Thr Ser   522

GCC TTC CAG ACC CAG AAG CCA TTG AAA TCT CTT TCA ACC TCT CTG TTT  1632
Ala Phe Gln Thr Gln Lys Pro Leu Lys Ser Leu Ser Thr Ser Leu Phe   538

TAT AAA AAA GTG TAT CGG CTA GCC TAT CTC CGG CTA AAT ACA CTT TGT  1680
Tyr Lys Lys Val Tyr Arg Leu Ala Tyr Leu Arg Leu Asn Thr Leu Cys   554

GAA CGC CTT CTG TCT GAG CAC CCA GAA TTA CAT ATC ATC TGG ACC  1728
Glu Arg Leu Leu Ser Glu His Pro Glu Leu His Ile Ile Trp Thr   570

CTT TTC CAG CAC ACC CTG CAG AAT GAG TAT GAA CTC ATG AGA GAC AGG  1776
Leu Phe Gln His Thr Leu Gln Asn Glu Tyr Glu Leu Met Arg Asp Arg   586

CAT TTG GAC CAA ATT ATG ATG TGT TCC ATG TAT GGC ATA TGC AAA GTG  1824
His Leu Asp Gln Ile Met Met Cys Ser Met Tyr Gly Ile Cys Lys Val   602

AAG AAT ATA GAC CTT AAA TTC AAA ATC ATT GTA ACA GCA TAC AAG GAT  1872
Lys Asn Ile Asp Leu Lys Phe Lys Ile Ile Val Thr Ala Tyr Lys Asp   618

CTT CCT CAT GCT GTT CAG GAG ACA TTC AAA CGT GTT TTG ATC AAA GAA  1920
Leu Pro His Ala Val Gln Glu Thr Phe Lys Arg Val Leu Ile Lys Glu   634
```

FIG. 2D

```
GAG GAG TAT GAT TCT ATT ATA GTA TTC TAT AAC TCG GTC TTC ATG CAG   1968
Glu Glu Tyr Asp Ser Ile Ile Val Phe Tyr Asn Ser Val Phe Met Gln    650

AGA CTG AAA ACA AAT ATT TTG CAG TAT GCT TCC ACC AGG CCC CCT ACC   2016
Arg Leu Lys Thr Asn Ile Leu Gln Tyr Ala Ser Thr Arg Pro Pro Thr    666

TTG TCA CCA ATA CCT CAC ATT CCT CGA AGC CCT TAC AAG TTT CCT AGT   2064
Leu Ser Pro Ile Pro His Ile Pro Arg Ser Pro Tyr Lys Phe Pro Ser    682

TCA CCC TTA CGG ATT CCT GGA GGG AAC ATC TAT ATT TCA CCC CTG AAG   2112
Ser Pro Leu Arg Ile Pro Gly Gly Asn Ile Tyr Ile Ser Pro Leu Lys    698

AGT CCA TAT AAA ATT TCA GAA CTG CCA ACA ACA CCA ATG ATG ACT AGT   2160
Ser Pro Tyr Lys Ile Ser Glu Leu Pro Thr Thr Pro Met Met Thr Ser    714

CCA AGA TCA AAA ATT TTA GTA ATT AAT CAG ATG GGT GAA TTC GGG ACT   2208
Pro Arg Ser Lys Ile Leu Val Ile Asn Gln Met Gly Glu Phe Gly Thr    730

GAG AAG TTC CAG TTT GAA GCT ATA AAT CAG ATG GTA TGT AAC AGC GAC   2256
Glu Lys Phe Gln Phe Glu Ala Ile Asn Gln Met Val Cys Asn Ser Asp    746

CTC AAA AGA AGT AGT GCT GAA GCT GGG CTG GGA AGC AAC CCT CCT AAA   2304
Leu Lys Arg Ser Ser Ala Glu Ala Gly Leu Gly Ser Asn Pro Pro Lys    762

CTA CGC TTT GAT ATT GAA AGT AGT GGA GGA TCA GAT GAA GCA GAT GGA   2352
Leu Arg Phe Asp Ile Glu Ser Ser Gly Gly Ser Asp Glu Ala Asp Gly    778

CTC CCA GGA GAG TCC AAA TTT CAG CAG AAA CTG GCA GAA ATG ACT TCT   2400
Leu Pro Gly Glu Ser Lys Phe Gln Gln Lys Leu Ala Glu Met Thr Ser    794
```

FIG. 2E

```
ACT CGA ACA CGA ATG CAA AAG CAG AAA ATG AAT GAT AGC ATG GAT ACC   2448
Thr Arg Thr Arg Met Gln Lys Gln Lys Met Asn Asp Ser Met Asp Thr    810

TCA AAC AAG GAA GAG AAA TGA GGATCTCAGG ACCTGGTGG ACACTGTGTA       2499
Ser Asn Lys Glu Glu Lys ***

CACCCTCTGGA TTCATTGTCT CTCACAGATG TGACTGTATA ACTTTCCCAG GTTCTGTTTA 2559

TGGCCACATT TAATATCTTC AGCTCTTTTT GTGGATATAA AATGTGCAGA TGCAATTGTT  2619

TGGGTGATTC CTAAGCCACT TGAAATGTTA GTCATTGTTA TTTATACAAG ATTGAAAATC  2679

TTGTGTAAAT CCTGCCATTT AAAAAGTTGT AGCAGATTGT TTCCTCTTCC AAAGTAAAAT  2739

TGCTGTGCTT TATGGATAGT AAGAATGGCC CTAGAGTGGG AGTCCTGATA ACCCAGGCCT  2799

GTCTGACTAC TTTGCCTTCT TTTGTAGCAT ATAGGTGATG TTTGCTCTTG TTTTTATTAA  2859

TTTATATGTA TATTTTTTTA ATTAACATG AACACCCTTA GAAAATGTGT CCTATCTATC   2919

ATCCAAATGC AATTTGATTG ACTGCCCATT CACCAAAATT ATCCTGAACT CTTCTGCAAA  2979

AATGGATATT ATTAGAAATT AGAAAAAAAT TACTAATTTT ACACATTAGA TTTTATTTTA  3039

CTATTGGAAT CTGATATACT GTGTGCTTGT TTTATAAAAT TTTGCTTTTA ATTAAATAAA  3099

AGCTGGAAGC AAAGTATAAC CATATGATAC TATCATACTA CTGAAACAGA TTTCATACCT  3159

CAGAATGTAA AAGAACTTAC TGATTATTTT CTTCATCCAA CTTATGTTTT TAAATGAGGA  3219

TTATTGATAG TGG                                                    3232
```

FIG. 2F

BROAD-SPECTRUM TUMOR SUPPRESSOR GENES GENE PRODUCTS AND METHODS FOR TUMOR SUPPRESSOR GENE THERAPY

This is a division of application Ser. No. 08/038,760, filed Mar. 25, 1993, now U.S. Pat. No. 5,496,731.

This invention was made in part with United States government support under grant number EY06195 awarded by National Institutes of Health. The United States government has certain rights in the invention.

1. BACKGROUND OF THE INVENTION

1.1 Field of the Invention

This invention is in the field of tumor suppressor genes (anti-oncogenes) and relates in general to products and methods for practicing broad-spectrum tumor suppressor gene therapy of various human cancers. In particulars the invention relates to methods for treating tumor cells (1) administering vectors comprising a nucleic acid sequence coding for a second in-frame AUG codon-initiated retinoblastoma protein of about 94 kD or (2) administering an effective amount of a protein coded for by the nucleic acid sequence.

1.2 Cancer

Cancers and tumors are the second most prevalent cause of death in the United States, causing 450,000 deaths per year. One in three Americans will develop cancer, and one in five will die of cancer (Scientific American Medicine, part 12, I, 1, section dated 1987). While substantial progress has been made in identifying some of the likely environmental and hereditary causes of cancer, the statistics for the cancer death rate indicates a need for substantial improvement in the therapy for cancer and related diseases and disorders

1.3. Cancer Genes

A number of so-called cancer genes, i.e., genes that have been implicated in the etiology of cancer, have been identified in connection with hereditary forms of cancer and in a large number of well-studied tumor cells. Study of cancer genes has helped provide some understanding of the process of tumorigenesis. While a great deal more remains to be learned about cancer genes, the presently known cancer genes serve as useful models for understanding tumorigenesis.

Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

1.3.1. Oncogenes

The oncogenes are somatic cell genes that are mutated from their wild-type alleles (the art refers to these wild-type alleles as protooncogenes) into forms which are able to induce tumorigenesis under certain conditions. There is presently a substantial literature on known and putative oncogenes and the various alleles of these oncogenes. In order to provide background information and to further the understanding of the scope of the invention, a brief discussion of representative oncogenes is provided.

For example, the oncogenes ras and myc are considered as models for understanding oncogenic processes in general The ras oncogene is believed to encode a cytoplasmic protein, and the myc oncogene is believed to encode a nuclear protein. Neither the ras oncogene nor the myc oncogene alone is able to induce full transformation of a normal cell into a tumor cell, but full tumorigenesis usually occurs when both the ras and myc oncogenes are present and expressed together in the same cell (Weinberg, R. A., 1989, *Cancer Research* 49:3713–3721, at page 3713). Such collaborative effects have been observed between a number of other studied oncogenes.

The collaborative model of oncogene tumorigenesis must be qualified by the observation that a cell expressing the ras oncogene that is surrounded by normal cells does not undergo full transformation. However, if most of the surrounding cells are also ras-expressing, then the ras oncogene alone is sufficient to induce tumorigenesis in a ras-expressing cell. This observation validates the multiple hit theory of tumorigenesis because a change in the tissue environment of the cell hosting the oncogene may be considered a second hit.

An alternative and equally valid hypothesis is that events that collaborate with the activation of an oncogene such as ras or myc may include the inactivation of a negative regulatory factor or factors (Weinberg, R. A., 1989, *Cancer Research* 49:3713–3721, at 3717; Goodrich, D. W. and Lee, W-H., 1992, Nature 360:177–179), i.e., a tumor suppressor protein.

1.3.2. Tumor Suppressor Genes

Tumor suppressor genes are genes that, in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism A number of well-studied human tumors and tumor cell lines have been shown to have missing or nonfunctional tumor suppressor genes. Examples of tumor suppression genes include, but are not limited to, the retinoblastoma susceptibility gene or RB gene, the p53 gene, the deleted in colon carcinoma (DCC) gene and the neurofibromatosis type 1 (NF-1) tumor suppressor gene (Weinberg, R. A. *Science*, 1991, 254:1138–1146). Loss of function or inactivation of tumor suppressor genes may play a central role in the initiation and/or progression of a significant number of human cancers.

The list of putative tumor suppressor genes is large and growing. The following discussion of tumor suppressor genes is not intended to provide a complete review of all known and putative tumor suppressor genes, but is provided as background to indicate the state of the art and the problems to be overcome before the art is able to provide successful genetic therapy of diseases and disorders characterized by abnormally proliferating cells, e.g., tumor or cancer cells.

1.3.2.1. The Retinoblastoma Gene

The RB gene is one of the better studied tumor suppressor genes. The size of the RB gene complementary DNA (cDNA), about 4.7 Kb, permits ready manipulation of the gene, so that insertions of the RB gene have been made into a number of cell lines. The RB gene has been shown to be missing or defective in a majority of retinoblastomas, sarcomas of the soft tissues and bones, and in approximately 20 to 40 percent of breast, lung, prostate and bladder carcinomas (Lee, W-H., et al., PCT Publ. No. WO 90/05180, at pages 38 and 39; see also, Bookstein, R. and Lee, W-H., 1991, *Crit. Rev. Oncog.*, 2:211–217; Benedict, W. F. et al., *J. Clin. Invests.*, 1990, 85:988–993).

Based upon study of the isolated RB cDNA clone, the predicted RB gene product has 928 amino acids and an expected molecular weight of 106 kD (Lee et al., 1987, Nature, 329:642–645). The natural factor corresponding to the predicted RB gene expression product has been identified as a nuclear phosphoprotein having an apparent relative molecular mass (Mr) of 110–114 kD (Lee et al., 1987, Nature, 329:642–645) or 110–116 kD (Xu et al., 1989, Oncogene 4:807–812). Hence, the literature generally refers to the protein encoded by the RB gene as p110$^{RB}$. In this connection, it is noteworthy that measurement of apparent relative molecular mass by SDS-PAGE is frequently inaccurate owing to protein secondary structure Therefore, the full length RB protein of 928 amino acids is also referred to as the 115 kD (Yokota et ale, 1988, Oncogene, 3:471–475), or 105 kD (Whyte et al., 1988, Nature, 334:124–129) RB proteins Various mutations of the RB gene are known. These are generally inactive However, a 56 kD truncated RB protein, designated as p56$^{RB}$, that is considered to function in the same way as does p110$^{RB}$ retains activity (Goodrich et al., 1992, Nature 360:177–179).

on SDS-PAGE normal human cells show an RB protein pattern consisting of a lower sharp band with an Mr of 110 kD and a broader, more variable region above this band with an Mr ranging from 110 kD to 116 kD. The 110 kD band is the under phosphorylated RB protein, whereas the broader region represents the phosphorylated RB protein. The heterogeneity of the molecular mass results from a varying degree of phosphorylation (Xu et al., 1989, Oncogene, 4:807–812).

The RB protein shows cyclical changes in phosphorylation. Host RB protein is unphosphorylated during G1 phase, but most (perhaps all) RB molecules are phosphorylated in S and G2 phases (Xu et al., 1989, Oncogene, 4:807–812; DeCaprio et al., 1989, Cell, 58:1085–1095; Buchkovich et al., 1989, Cell, 58:1097–1105; Chen et al., 1989, Cell, 58:1193–1198; Mihara et al., 1989, Science, 246:1300–1303). Furthermore, only the under phosphorylated RB protein binds to SV40 large T antigen. Given that RB protein binding by large T antigen is probably important for the growth promoting effects of large T antigen, this suggests that the under phosphorylated RB protein is the active form of the RB protein, and the phosphorylated RB protein in S and G2 phases is inactive (Ludlow et al., 1989, Cell, 56:57–65).

The RB gene expressing the first in-frame AUG codon-initiated RB protein is also referred to herein as the intact RB gene, the RB$^{110}$ gene or the p110$^{RB}$ coding gene. It has also been observed that lower molecular weight (<100 kD, 98 kD, or 98–104 kD) bands of unknown origin which are immunoreactive to various anti-RB antibodies can be detected in immunoprecipitation and Western blots (Xu et al., 1989, Oncogene, 4:807–812; Furukawa et al., 1990, Proc. Natl. Acad. Sci., USA, 87:2770–2774; Stein et al., 1990, Science, 249,666–669).

Considering that the RB$^{110}$ cDNA open reading frame sequence (McGee, T. L., et al., 1989, Gene, 80:119–128) reveals an in-frame second AUG codon located at exon 3, nucleotides 355–357, the deduced second AUG codon-initiated RB protein would be 98 kD, or 12 kD smaller than the p110$^{RB}$ protein. It has been proposed that the lower molecular weight bands are the under phosphorylated (98 kD) and phosphorylated (98–104 kD) RB protein translated from the second AUG codon of the RB mRNA (Xu et al., 1989, Oncogene, 4:807–812), although no data directly supported this hypothesis. Thus, no conclusive observation confirms the actual expression of the RB gene from the second in-frame AUG codon. Further, Sections 4.2.1, and FIG. 5 infra provide data indicating the non-identity of the 98 kD protein bands of unknown origin and the second AUG codoninitiated protein products It has been proposed that introduction of a functional RB$^{110}$ gene into an RB-minus tumor cell will likely "normalize" the cell of course, it is not expected that tumor cells which already have normal RB$^{110}$ gene expression ("RB+") will respond to RB$^{110}$ gene therapy, because it is presumed that adding additional RB expression cannot correct a non-RB genetic defect In fact, it has been shown that in the case of RB+ tumor cell lines, such as the osteosarcoma cell line, U-2 OS, which expresses the normal p110$^{RB}$, introduction of an extra p110$^{RB}$ coding gene did not change the neoplastic phenotype of such tumor lines (Huang, et al., 1988, Science, 242:1563–1566).

In the only reported exception, introduction of a p110$^{RB}$ coding vector into normal human fibroblasts, WS1, which have no known RB or any other genetic defects, led to the cessation of cell growth (WO 91/15580, Research Development Foundation, by Fung et al., PCT application filed Apr. 10, 1991, published Oct. 17, 1991, at page 18). However, it is believed that these findings were misinterpreted since a plasmid, ppVUO-Neo, producing SV40 T antigen with a well-known growth-promoting effect on host cells was used improperly to provide a comparison with the effect of RB$^{110}$ expression on cell growth of transfected WS1 fibroblasts (Fung, et al. Id. see Example 2 page 25). This view is confirmed by the extensive literature, together with similar confirming data provided by the examples presented infra, clearly characterizing RB+ tumor cells as "incurable" by treatment with wild-type RB$^{110}$ gene. In addition, it is noteworthy that the WS1 cell line per se is a generally recognized non-tumorigenic human diploid fibroblast cell line with limited cell division potential in culture. Therefore, W091/15580 simply does not provide any method for effectively treating RB+ tumors with an RB$^{110}$ gene. Thus, there remains a need for a broad-spectrum tumor suppressor gene for treating abnormally proliferating cells having any type of genetic defect.

1.3.2.2. The Neurofibromatosis Gene

Neurofibromatosis type 1 or von Recklinghausen neurofibromatosis results from the inheritance of a predisposing mutant allele or from alleles created through new germline mutations (C. J. Marshall, 1991, Cell, 64:313–326). The neurofibromatosis type 1 gene, referred to as the NF1 gene, is a relatively large locus exhibiting a mutation rate of around $10^4$. Defects in the NF1 gene result in a spectrum of clinical syndromes ranging from cafe-au-lait spots to neurofibromas of the skin and peripheral nerves to Schwannomas and neurofibrosarcomas.

The NF1 gene encodes a protein of about 2485 amino acids that shares structural similarity with three proteins that interact with the products of the ras protooncogene (Weinberg et al., 1991, Science, 2541138–1146 at page 1141). For example, the NF1 amino acid sequence shows sequence homology to the catalytic domain of ras GAP, a GTPase-activating protein for p21 ras (C. J. Harshall, 1991, Cell, 64:313–326 at pages 320 and 321).

The role of NF1 in cell cycle regulation is apparently a complex one that is not yet fully elucidated. For example, it has been hypothesized that it is a suppressor of oncogenically activated p21 ras in yeast (C. J. Marshall, (1991, Cell, 64:313–326, bridging pages 320 and 321, and citing to Ballester et al, 1990, Cell, 63:851–859). On the other hand, other possible pathways for NF1 interaction are suggested by the available data (C. J. Marshall, 1991, Cell, 64:313–326 at page 321; Weinberg et al., 1991, Science, 254:1138–1146 at page 1141).

At present, no attempts to treat NF1 cells with a wild-type NF1 gene have been undertaken due to the size and complexity of the NF1 locus. Therefore, it would be highly desirable to have a broad-spectrum tumor suppressor gene able to treat NF1 and any other type of cancer or tumor.

1.3.3.3. The p53 Gene

Somatic cell mutations of the p53 gene are said to be the most frequently mutated gene in human cancer (Weinberg et al., 1991, Science, 254:1138–1146 at page 1143). The normal or wild-type p53 gene is a negative regulator of cell growth, which, when damaged, favors cell transformation (Weinberg et al. supra). As noted for the RB protein, the p53 expression product is found in the nucleus, where it may act in parallel with or cooperatively with p110$^{RB}$. This is suggested by a number of observations, for example, both p53 and p110$^{RB}$ proteins are targeted for binding or destruction by the oncoproteins of SV40, adenovirus and human papillomavirus.

Tumor cell lines deleted for p53 have been successfully treated with wild-type p53 vector to reduce tumorigenicity (Baker, S. J., et al., 1990, Science, 249:912–915). However, the introduction of either p53 or RB$^{110}$ into cells that have not undergone lesions at these loci does not affect cell proliferation (Marshall, C. J. 1991, Cell, 64:313–326 at page 321; Baker, S. J. et al., 1990, Science, 249:912–915; Huang, H.-J.S., et al., 1988 Science, 242:1563–1566). Such experiments suggest that sensitivity of cells to the suppression of their growth by a tumor suppressor gene is dependent on the genetic alterations that have taken place in the cells. Such a dependency would be further complicated by the observation in certain cancers that alterations in the p53 tumor suppressor or gene locus appear after mutational activation of the ras oncogene (Marshall, C. J., 1991, Cell, 64:313–326; Fearon, E. R., and Vogelstein, B., 1990, Cell, 61:759–767).

Therefore, there remains a need for a broad-spectrum tumor suppressor gene that does not depend on the specific identification of each mutated gene causing abnormal cellular proliferation.

1.3.3.4. The Deleted in Colon Carcinoma Gene (DCC)

The multiple steps in the tumorigenesis of colon cancer are readily monitored during development by colonoscopy. The combination of colonoscopy with the biopsy of the involved tissue has uncovered a number of degenerative genetic pathways leading to the result of a malignant tumor. One well studied pathway begins with large polyps of which 60% of the cells carry a mutated, activated allele of K-ras. A majority of these tumors then proceed to the inactivation-mutation of the gene referred to as the deleted in colon carcinoma (DCC) gene, followed by the inactivation of the p53 tumor suppressor gene.

The DCC gene is a more than approximately one million base pair gene coding for a 190-kD transmembrane phosphoprotein which is hypothesized to be a receptor (Weinberg et al., 1991, Science, 254:1138–1146 at page 1141), the loss of which allows the affected cell a growth advantage. It has also been noted that the DCC has partial sequence homology to the neural cell adhesion molecule (Marshall, 1991, Cell, 64:313–326) which might suggest a role for the DCC protogene in regulating cell to cell interactions.

As can be appreciated, the large size and complexity of the DCC gene, together with the complexity of the K-ras, p53 and possibly other genes involved in colon cancer tumorigenesis demonstrates a need for a broad-spectrum tumor suppressor gene and methods of treating colon carcinoma cells which do not depend upon manipulation of the DCC gene or on the identification of other specific damaged genes in colon carcinoma cells.

1.4 Genetic Therapy: Gene Transfer Methods

The treatment of human disease by gene transfer has now moved from the theoretical to the practical realm. The first human gene therapy trial was begun in September 1990 and involved transfer of the adenosine deaminase (ADA) gene into lymphocytes of a patient having an otherwise lethal defect in this enzyme, which produces immune deficiency The results of this initial trial have been very encouraging and have helped to stimulate further clinical trials (Culver, K. W., Anderson, W. F., Blaese, R. M., Hum. Gene. Ther., 1991, 2:107).

So far all but one of the approved gene transfer trials in humans rely on retroviral vectors for gene transduction. Retroviral vectors in this context are retroviruses from which all viral genes have been removed or altered so that no viral proteins are made in cells infected with the vector. Viral replication functions are provided by the use of retrovirus 'packaging' cells that produce all of the viral proteins but that do not produce infectious virus Introduction of the retroviral vector DNA into packaging cells results in production of virions that carry vector RNA and can infect target cells, but no further virus spread occurs after infection. To distinguish this process from a natural virus infection where the virus continues to replicate and spread, the term transduction rather than infection is often used.

The major advantages of retroviral vectors for gene therapy are the high efficiency of gene transfer into replicating cells, the precise integration of the transferred genes into cellular DNA, and the lack of further spread of the sequences after gene transduction (Miller, A. D. Nature, 1992, 357:455–460).

The potential for production of replication-competent (helper) virus during the production of retroviral vectors remains a concern, although for practical purposes this problem has been solved. So far, all FDA-approved retroviral vectors have been made by using PA317 amphotropic retrovirus packaging cells (Miller, A. D., and Buttimore, C., Molec Cell Biol., 1986, 6:2895–2902). Use of vectors having little or no overlap with viral sequences in the PA317 cells eliminates helper virus production even by stringent assays that allow for amplification of such events (Lynch, C. H., and Miller, A. D., J. Viral., 1991, 65:3887–3890). Other packaging cell lines are available. For example, cell lines designed for separating different retroviral coding regions onto different plasmids should reduce the possibility of helper virus production by recombination. Vectors produced by such packaging cell lines may also provide an efficient system for human gene therapy (Miller, A. D., 1992, Nature, 357:455–460).

Non-retroviral vectors have been considered for use in genetic therapy. One such alternative is the adenovirus (Rosenfeld, M. A., et al., 1992, Cell, 68:143155; Jaffe, H. A. et al., 1992, Nature Genetics 1.372–378; Lemarchand, P. et al., 1992, Proc. Natl. Acad. Sci. USA, 89:6482–6486). Major advantages of adenovirus vectors are their potential to carry large segments of DNA (36 Kb genome), a very high titre ($10^{11}$ ml$^{-1}$), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., Cell, 1992, 63:143–155). Similarly, herpes viruses may also prove valuable for human gene therapy (Wolfe, J. H. et al., 1992, Nature Genetics, 1:379–384). Of course, any other suitable viral vector may be used for genetic therapy with the present invention.

The other gene transfer method that has been approved by the FDA for use in humans is the transfer of plasmid DNA in liposomes directly to human cells in situ (Nabel, E. G., et al., 1990, *Science,* 249:1285–1288). Plasmid DNA should be easy to certify for use in human gene therapy because, unlike retroviral vectors, it can be purified to homogeneity In addition to liposome-mediated DNA transfer, several other physical DNA transfer methods such as those targeting the DNA to receptors on cells by completing the plasmid DNA to proteins have shown promise in human gene therapy (Wu, G. Y., et al., 1991, *J. Biol. Chem.,* 266:14338–14342; Curiel, D. T., et al., 1991, *Proc. Natl. Acad. Sci. USA,* 88:8850–8854).

1.5 Proposed Strategies for Cancer Gene Therapy

It has been observed that certain tumor cells return to normal function when fused with normal cells, suggesting that replacement of a missing factor, such as a wild-type tumor suppressor gene expression product may serve to restore a tumor cell to a normal state (reviewed by Weinberg, R. A., 1989, *Cancer Research* 49:3713–3721, at 3717)

These observations have led to research aimed at providing genetic treatment of tumor cells having defective tumor suppressor genes. The proposed method of treatment requires identification of the damaged tumor suppressor gene, and introduction of the corresponding undamaged gene (including a promoter and a complete encoding sequence) into the affected tumor cells by means of a vector such as a retrovirus able to express the gene product It is proposed that the incorporated functional gene will convert the target cell to a non-malignant state.

For example, The Regents of the University of California, in Patent Cooperation Treaty patent application (by Lee et al., number WO 90/05180, having an international filing date of Oct. 30, 1989 and published May 17, 1990), disclose a scheme for identifying an inactive or defective tumor suppressor gene and then replacing such a defective gene with its functional equivalent. In particular, the WO 90/05180 application proposes, based on in vitro studies, to insert a functional $RB^{110}$ gene into an RB-minus tumor cell by means of a retroviral vector in order to render such cells non-malignant.

In addition, international application WO 89/06703 (by Dryja et al., having an international filing date of Jan. 23, 1989, and published Jul. 27, 1989) proposes the treatment of retinoblastoma defective tumors by administering a retinoblastoma gene expression product.

In this connection, it has been reported that the introduction of the $RB^{110}$ gene into RB-minus retinoblastoma, osteosarcoma, bladder and prostate carcinoma cells resulted in cells showing reduced tumorigenicity in nude mice, but probably not a reduced cell growth rate. The results varied depending on the particular parental cell line (Goodrich et al., 1992, *Cancer Research* 52:1968–1973; Banerjee, A., et al., 1992, *Cancer Research,* 52:6297–6304; Takahashi, R., et al., 1991, *Proc. Natl. Acad. Sci., USA,* 88:5257–5261; Xu, H-J., et al., 1991, *Cancer Research,* 51:4481–4485; Bookstein et al, 1990, *Science,* 247:712–715; Huang, H-J. S., et al., 1988, *Science* 242, 1563–1566). However, the suppression of tumorigenicity by introduction of the $p110^{RB}$ coding gene into RB-minus tumor cells is incomplete. The $p110^{RB}$ reconstituted tumor cells still form invasive tumors in nude mice (Xu, H-J , et al., 1991, *Cancer Research,* 51:4481–4485; Takahashi, R., et al., 1991, *Proc. Natl. Acad. Sci., USA,* 88:5257–5261; Banerjee, A., et al., 1992, *Cancer Research,* 52:6297–6304). In particular, it has been shown that $p110^{RB}$ reconstituted retinoblastoma cells inoculated into an orthotopic site (in this instance, the eye) consistently produced tumors (Xu, H-J., et al., 1991, *Cancer Research* 51:4481–4485). These findings, which will be discussed in detail infra, caution that the tumor suppressor gene replacement therapy as heretofore envisioned may simply result in cells that only appear to be "cured" Certainly, the findings of Xu et al. indicate a need for an improved genetic therapy for tumors which avoids these shortcomings.

Another proposed method of treating cancer by gene therapy is to antagonize the function of an oncogene by placing an artificial gene, constructed to have an inverted nucleotide sequence compared to the oncogene, into a tumor cell (U.S. Pat. No. 4,740,463, issued Apr. 26, 1988 by Weinberg, et al.).

All of these proposed solutions also share the deficiency of requiring that the specific genetic defect of the tumor to be treated be identified prior to treatment.

Since the $p110^{RB}$ protein product is active in the under phosphorylated state (discussed in detail supra), and phosphoamino acid analysis has demonstrated only phosphoserine and phosphothreonine but not phosphotyrosine in RB protein (Shew, J-Y, et al., 1989, *Ocogene Research,* 1:205–213), it has been proposed to make a mutant RB protein with its serine or threonine residues being replaced by alanine or valine or others and that introduction of such a mutant, unphosphorylated RB protein into target cells may lead to growth arrest (International Application WO 91/15580, Research Development Foundation, by Fung et al., at page 20). Unfortunately, in all cases analyzed so far, the human RB protein carrying a point mutation and retaining the unphosphorylated state were invariably inactive proteins and associated with tumorigenesis rather than tumor suppression (Templeton et al., 1991, *Proc. Natl. Acad. Sci., USA,* 88,3033–3037.

1.6 Tumor Suppressor Gene Resistance

As the above discussion of gene mutations in tumor cells has indicated, not every cancer gene is a suitable candidate for wild-type gene replacement therapy due to the gene size or complexity or for other reasons The retinoblastoma gene is one of those tumor suppressor genes that is readily accessible to study, thus it provides a model for understanding some of the other disadvantages to cancer gene replacement therapy as heretofore understood.

It is known that reintroduction of the retinoblastoma tumor suppressor gene into RB-defective tumor cells inhibits the tumor cell growth and suppresses the neoplastic phenotype of the target cells (WO 90/05180, cited supra; Huang et al, 1988, *Science,* 242:1563–1566; Bookstein et al, 1990, *Science,* 247:712–715; Xu et al, 1991, *Cancer Res.,* 51:4481–4485; Takahashi et al., 1991, *Proc. Natl. Acad. Sci., USA,* 88:5257–5261; Goodrich et al., 1992, *Cancer Res.,* 52:1968–1973; Banerjee et al., 1992, *Cancer Res.,* 52:6297–6304).

However, the suppression of tumorigenicity is often incomplete. A significant percentage of the RB-reconstituted tumor cells still form small tumors after a longer latency period in nude mouse tumorigenicity assays. Such tumors, although retaining normal RB expression, are histologically malignant and invasive (Xu et al., 1991, *Cancer Res.,* 51:4481–4485; Takahashi et al., 1991, *Proc. Natl. Acad. Sci., USA,* 88:5257–5261; Banerjee et al., 1992, *Cancer Res.,* 52:6297–6304).

Furthermore, it has been observed that several cell lines derived from such RB-positive tumors have become very tumorigenic and have formed large, progressively growing tumors when subsequently injected into nude mice (Zhou, Y.; Li, J.; Xu, K.; Hu, S-X.; Benedict, W. F., and Xu, H-J., *Proc. Am. Assoc. Cancer Res.,* 34:3214, 1993). This phenomenon, which is referred to herein as tumor suppressor gene resistance (TSGR) is a serious obstacle to the successful implementation of any scheme of tumor suppressor gene therapy for human cancers.

Without wishing to be bound by any particular hypothesis or explanation of the TSGR phenomenon, it is believed that the RB gene product exemplifies a possible explanation for TSGR. RB proteins have an active form (under phosphorylated protein) and an inactive form (phosphorylated protein). Therefore, RB-positive tumor cells may have inherited or acquired the ability to phosphorylate RB proteins to the inactive state and allow tumor cell proliferation to continues Thus, conversion of RB-minus cells with plasmid or virus vectors coding for the $p110^{RB}$ protein provides only incomplete suppression, or even exacerbation of a percentage of the malignant cell population because the $p110^{RB}$ protein remains phosphorylated and inactive in some of the target cells.

Alternatively, the tumor cells expressing the $RB^{110}$ gene may simply have again inactivated the $RB^{110}$ gene by mutation in subsequent cell divisions (Lee et al., 1990,, Immunol. Ser. 51.169–200, at page 188). Thus, there remains a need for a method of treating tumor cells by gene therapy so that the possibility of further mutation and resurgence of malignancy is avoided.

1.7 Summary of Obstacles to Cancer Gene Therapy

In brief, there are at least three major obstacles to be overcome to achieve a practical tumor suppressor gene therapy for tumor cells:

1) The necessity to determine the identity and sequence of each defective tumor suppressor gene or oncogene before attempting genetic therapy of that tumor. This is particularly a problem considering the multiple genetic defects found in many tumor cells studied;

2) The size and complexity of certain tumor suppressor genes or oncogenes renders manipulation of certain of these genes difficult; and 3) The possibility that TSGR as described above for the $RB^{110}$ model system will generate tumor cells that have equal or greater dysfunction than did the original abnormal cells.

Accordingly, there is a need in the art for a genetic therapy for tumor or cancer cells which can safely overcome these problems and provide an effective treatment for all types of tumor cells without the need to determine the exact genetic deficiency of each treated tumor cell and without the risk of TSGR resurgence and exacerbation of the malignancy.

SUMMARY OF THE INVENTION

Obstacles to the successful practice of tumor suppressor gene therapy of cancers are avoided by the present invention. In a totally unexpected and surprising discovery, it has been determined that the second in-frame AUG codon-initiated retinoblastoma suppressor protein of about 94 kD ($p94^{RB}$) is a broad-spectrum tumor suppressor, and that insertion of a gene capable of expressing this protein, or the protein itself, into an abnormally proliferating cell, such as a cancer or tumor cell, causes that cell to enter a senescent-like state, terminating the proliferation. The cell so-treated simply stops replicating and dies. The cell may possess any type of genetic defect, known or unknown, so that there is no need to determine the exact nature of the genetic defect associated with the abnormal proliferation. Further, the population of treated cells exhibits an unexpectedly much lower incidence of TSGR resurgence and exacerbation of malignancy than do cells treated with any other tumor suppressor gene. The method is repeated as needed.

Therefore, the invention provides $p94^{RB}$ encoding vectors and $p94^{RB}$ proteins for use in treatment of tumors or cancers, and methods of preparing $p94^{RB}$ proteins suitable for use in methods of treatment. The invention also provides methods of treatment for mammals such as humans, as well as methods of treating abnormally proliferating cells, such as cancer or tumor cells. Broadly, the invention contemplates treating abnormally proliferating cells, or mammals having a disease characterized by abnormally proliferating cells by any suitable method known to permit a host cell compatible $p94^{RB}$ encoding vector or a $p94^{RB}$ protein to enter the calls to be treated so that suppression of proliferation is achieved.

In one embodiment, the invention comprises a method of treating a disease characterized by abnormally proliferating cells, in a mammal, by administering an expression vector coding for $p94^{RB}$ to the mammal having a disease characterized by abnormally proliferating cells, inserting the expression vector into the abnormally proliferating cells, and expressing $p94^{RB}$ in the abnormally proliferating cells in an amount effective to suppress proliferation of those cells. The expression vector is inserted into the abnormally proliferating cells by viral infection or transduction, liposome-mediated transfection, polybrene-mediated transfection, CaPO4 mediated transfection and electroporation. The treatment is repeated as needed.

In another embodiment, the invention comprises a method of treating abnormally proliferating cells of a mammal by inserting a $p94^{RB}$ encoding expression vector into the abnormally proliferating cells and expressing $p94^{RB}$ therein in amounts effective to suppress proliferation of those cells. The treatment is repeated as needed.

In another alternative embodiment, the invention provides a DNA molecule able to suppress growth of an abnormally proliferating cell. The DNA molecule encodes a $p94^{RB}$ protein having an amino acid sequence substantially according to SEQ ID NO:3, provided that the DNA molecule does not also code for a $p110^{RB}$ proteins In a more preferred embodiment, the DNA molecule has the DNA sequence of SEQ ID NO:1, and is expressed by an expression vector. The expression vector may be any host cell-compatible vector. The vector is preferably selected from the group consisting of a retroviral vector, an adenoviral vector and a herpesviral vector.

In another alternative embodiment, the invention provides a $p94^{RB}$ protein having an amino acid sequence substantially according to SEQ ID NO:3.

In another alternative embodiment, the invention provides a method of producing a $p94^{RB}$ protein by the steps of: inserting a compatible expression vector comprising a $p94^{RB}$ encoding gene into a host cell and causing the host cell to express $p94^{RB}$ protein.

In another alternative embodiment, the invention comprises a method of treating abnormally proliferating cells of a mammal ex vivo by the steps of: removing a tissue sample in need of treatment from a mammal, the tissue sample comprising abnormally proliferating cells; contacting the tissue sample in need of treatment with an effective dose of an $p94^{RB}$ encoding expression vector; expressing the $p94^{RB}$ in the abnormally proliferating cells in amounts effective to suppress proliferation of the abnormally proliferating cells. The treatment is repeated as necessary; and the treated tissue sample is returned to the original or another mammal. Preferably, the tissue treated ex vivo is blood or bone marrow tissue.

In another alternative embodiment, the invention comprises a method of treating a disease characterized by abnormal cellular proliferation in a mammal by a process comprising the steps of administering p94$^{RB}$ protein to a mammal having a disease characterized by abnormally proliferating cells, such that the p94$^{RB}$ protein is inserted into the abnormally proliferating cells in amounts effective to suppress abnormal proliferation of the cells. In a preferred embodiments the p94$^{RB}$ protein is liposome encapsulated for insertion into cells to be treated. The treatment is repeated as necessary.

In another alternative embodiment the invention comprises a method of treating abnormally proliferating cells of a mammal ex vivo by a process comprising the steps of removing a tissue sample in need of treatment from a mammal, the tissue sample comprising abnormally proliferating cells contacting the tissue sample in need of treatment with an effective dose of a p94$^{RB}$ protein. The treatment is repeated as necessary, and then the treated tissue is returned to the mammal or placed into another mammal.

In a more preferred embodiment the tumor or cancer cells to be treated are cells having one or more genetically defective tumor suppressor genes and oncogenes selected from the group consisting of an RB, a p53, a c-myc, an N-ras and a c-yes-1 gene.

In a more preferred embodiment the tumor or cancer cells are cells having no detectable genetic defect of a tumor suppressor gene selected from the group consisting of an RB gene and a p53 gene.

In a still more preferred embodiment the tumor or cancer cells are lung carcinoma cells.

In a still more preferred embodiment the p94$^{RB}$ encoding expression vector or the p94$^{RB}$ protein are administered by means of aerosol delivery of liposome-encapsulated p94$^{RB}$ encoding expression vector or p94$^{RB}$ protein into a lung in need of such treatment.

3. DETAILED DESCRIPTION OF THE INVENTION

3.1 Definitions

The terms "cancer" or "tumor" are clinically descriptive terms which encompass a myriad of diseases characterized by cells that exhibit unchecked and abnormal cellular proliferation. The term "tumor", when applied to tissue, generally refers to any abnormal tissue growth, i.e., excessive and abnormal cellular proliferation. A tumor may be "benign" and unable to spread from its original focus, or "malignant" and capable of spreading beyond its anatomical site to other areas throughout the hostbody. The term "cancer" is an older term which is generally used to describe a malignant tumor or the disease state arising therefrom. Alternatively, the art refers to an abnormal growth as a neoplasm, and to a malignant abnormal growth as a malignant neoplasm Irrespective of whether the growth is classified as malignant or benign, the causes of excessive or abnormal cellular proliferation of tumor or cancer cells are not completely clear. Nevertheless, there is persuasive evidence that abnormal cellular proliferation is the result of a failure of one or more of the mechanisms controlling cell growth and division. It is also now believed that the mechanisms controlling cell growth and division include the genetic and tissue-mediated regulation of cell growth, mitosis and differentiation These mechanisms are thought to act at the cell nucleus, the cell cytoplasm, the cell membrane and the tissue-specific environment of each cell. The process of transformation of a cell from a normal state to a condition of excessive or abnormal cellular proliferation is called tumorigenesis.

It has been observed that tumorigenesis is usually a multistep progression from a normal cellular state to, in some instances, a full malignancy. It is therefore believed that multiple "hits" upon the cell regulatory mechanisms are required for full malignancy to develop. Thus, in most instances, it is believed that there is no single cause of excessive proliferation, but that these disorders are the end result of a series of cumulative events.

While a malignant tumor or cancer capable of unchecked and rapid spread throughout the body is the most feared and usually the deadliest type of tumor, even so-called benign tumors or growths can cause significant morbidity and mortality by their inappropriate growth. A benign tumor can cause significant damage and disfigurement by inappropriate growth in cosmetically sensitive areas, or by exerting pressure on central or peripheral nervous tissue, blood vessels and other critical anatomical structures.

A broad-spectrum tumor suppressor gene is a genetic sequence coding for a protein that, when inserted into and expressed in an abnormally proliferating host cell, e.g., a tumor cell, suppresses abnormal proliferation of that cell irrespective of the cause of the abnormal proliferation. The second in-frame AUG (ATG in DNA) codon-initiated retinoblastoma gene disclosed herein exemplifies such a broad-spectrum tumor suppressor gene and is referred to herein as the p94$^{RB}$ coding gene, as the RB$^{94}$ gene or as a DNA molecule coding for pRB$^{94}$. According to the nucleotide sequence of the retinoblastoma susceptibility gene (McGee, T. L., et al., 1989, Gene, 80:119–128), the p94$^{RB}$ coding gene comprises the nucleotide sequence from exon 3, nucleotide 355 to exon 27, nucleotide 264. Thus, the p94$^{RB}$ encoding gene by definition excludes that portion of the RB$^{110}$ gene upstream from the second in-frame AUG start codon. FIG. 1 shows the DNA sequence of the RB$^{94}$ gene wherein the ATG codon begins at nucleotide 19 of that figure (SEQ ID NO:1; SEQ ID NO:2).

A broad-spectrum tumor suppressor protein (including phosphoproteinse lipoproteins, glycoproteins and other protein-based derivatives) is a substance that when injected into, absorbed by or caused to be expressed in any abnormally proliferating cell, reduces or completely suppresses abnormal cellular proliferation. The protein expressed by the second in-frame AUG codon-initiated retinoblastoma gene disclosed herein exemplifies such a broad-spectrum tumor suppressor protein. It is a phosphoprotein of about 94 kD relative molecular mass, and is also referred to herein as p94$^{RB}$ (SEQ ID NO:3).

One of ordinary skill in the art will be able to determine if any other fragment of a tumor suppressor protein, erg., the third or fourth AUG codon-initiated retinoblastoma protein of about 90 kD and 83 kD, respectively, also has the property of suppressing abnormal cellular proliferation.

3.2 Brief Description of the Figures

FIGS. 1A–1F: Nucleotide sequence of the cDNA fragment encoding the 94 kD therapeutic RB protein (plus strand is SEQ ID NO:1, minus strand is SEQ ID NO:2).

FIGS. 2A–2F: Amino acid sequence of the 94 kDa therapeutic RB protein (SEQ ID NO:3).

FIG. 3: Construction of baculovirus expression vector for the 94 kDa therapeutic RB protein synthesis; *R.S. is recombination sequence FIGS. 4A–4C: Intracellular localization of recombinant baculovirus-produced p110$^{RB}$ and p94$^{RB}$ in insect cells: panel A shows mock-infected Sf9 cells; panel B shows cells producing p110$^{RB}$; and panel C shows cells producing p94$^{RB}$; note that protein is localized to the nucleus in panels B and C. Protein localization is by anti-RB immunochemical staining.

Figure 5:
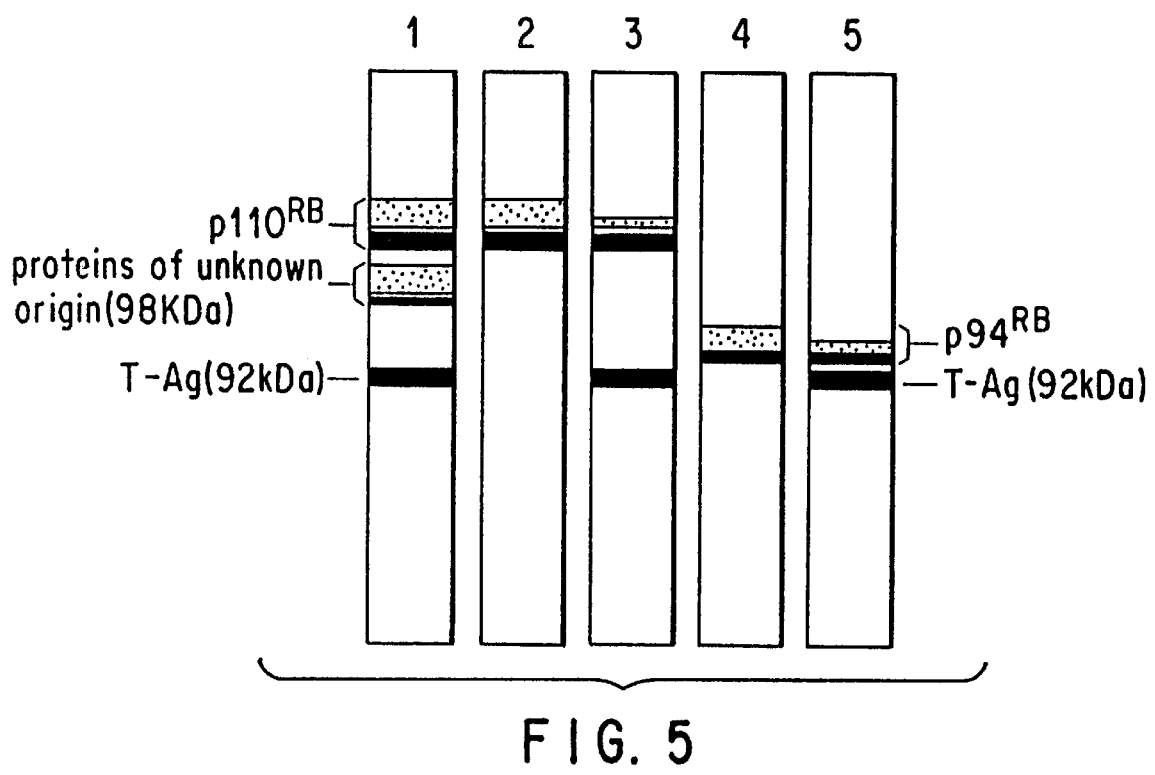

FIG. 5: A diagram of complex formation of baculovirus-expressed and subsequently purified p110$^{RB}$ and p94$^{RB}$ proteins with SV40 T antigen. The immunoaffinity chromatography purified proteins were mixed with an equal amount of T antigen, and aliquots of the mixture were immunoprecipitated with PAB419 anti-T antibody, followed by Western blotting. The blot was sequentially incubated with HAb-1 anti-RB antibody and PAB419 antibody Lane 1, lysate of T antigen immortalized W138 VA13 fibrobrasts was used as a control; lane 2, purified p110$^{RB}$; lane 3, co-precipitation of T-Ag with p110$^{RB}$; lane 4, purified p94$^{RB}$; lane 5, co-precipitation of T-Ag with p94$^{RB}$.

Figure 6A:
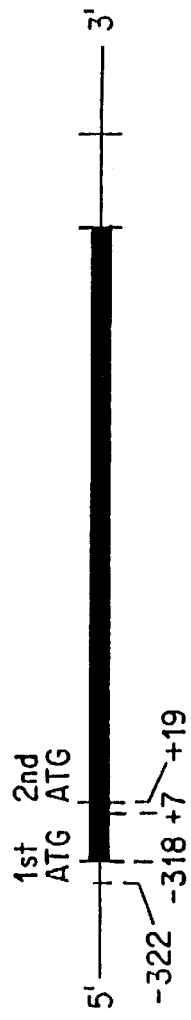
Figure 6B:
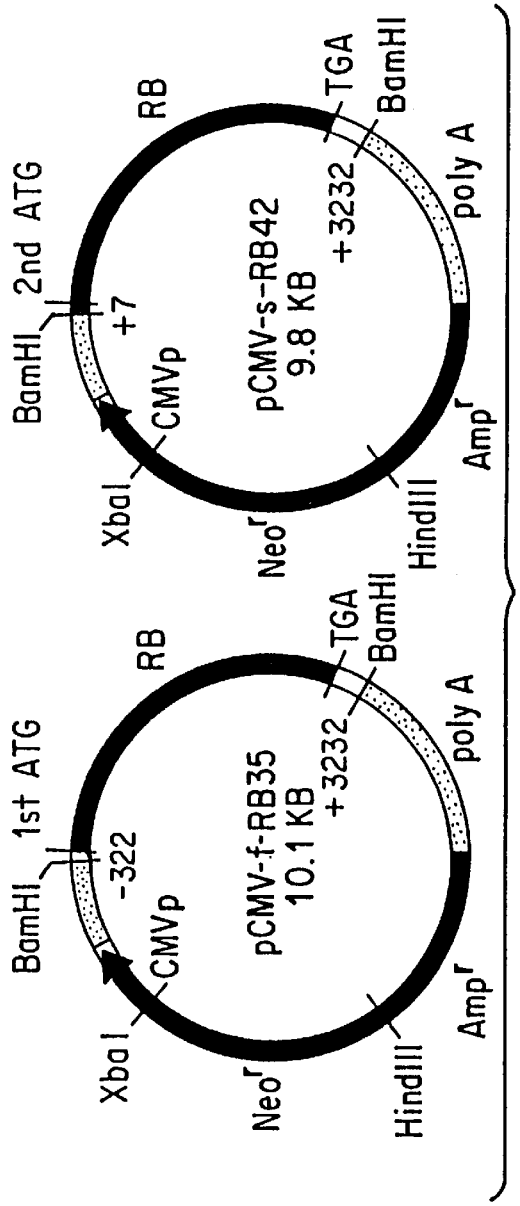

FIGS. 6A and 6B: Construction of recombinant plasmids for high-level expression of p110$^{RB}$ (pCHV-f-RB35) and p94$^{RB}$ (pCHV-s-RB42) proteins in human cells using cytolomegalovirus promoter/enhancer: panel A is an explanatory drawing of the p110$^{RB}$ coding cDNA; panel B provides maps of the p110$^{RB}$ and p94$^{RB}$ expression plasmids where pCHV-f-RB35 codes for p110$^{RB}$ and pCHV-s-RB42 codes for p94$^{RB}$. Note that pCNV-s-RB42 has most of p110$^{RB}$ coding region deleted upstream of the second ATG.

Figure 7B:
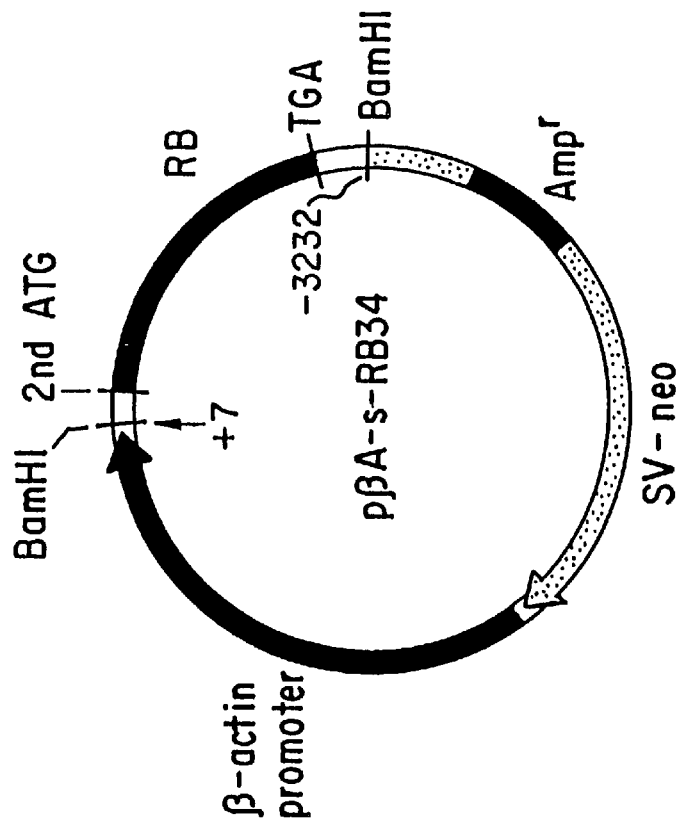
Figure 7A:
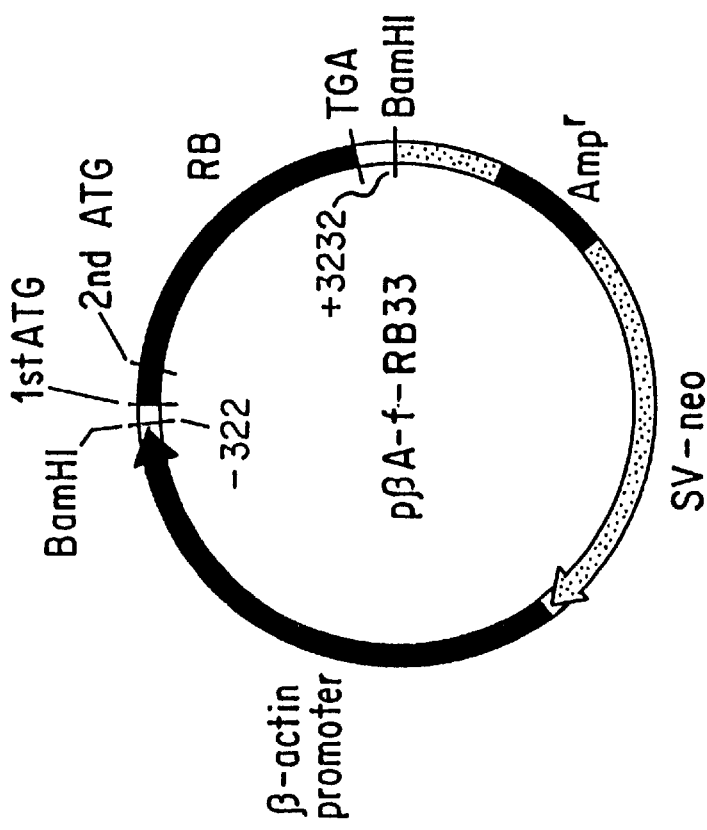

FIGS. 7A and 7B: Construction of recombinant plasmids for expression of p110$^{RB}$ (pβA-f-RB33) and p94$^{RB}$ (pβA-s-RB34) proteins in human cells using β-actin promoter: panel A is a map of the p110$^{RB}$ coding plasmid, pβA-f-RB33; panel B is a map of the p94$^{RB}$ coding plasmid, pβA-s-RB34. Note that pβA-s-RB34 has most of the p110$^{RB}$ coding region deleted upstream of the second ATG.

Figure 8A:
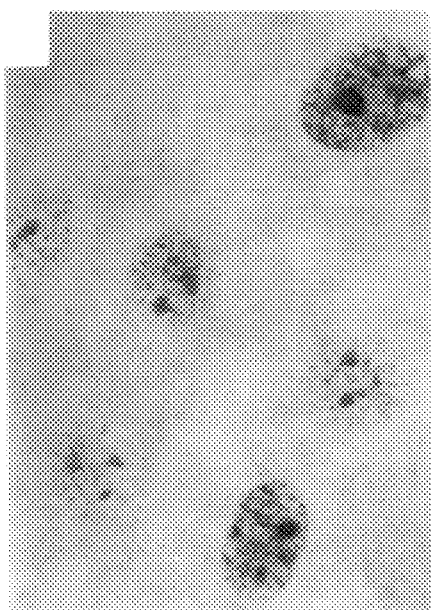
Figure 8B:
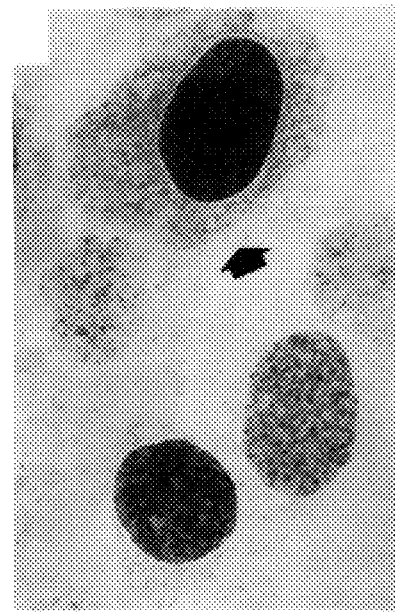
Figure 8C:
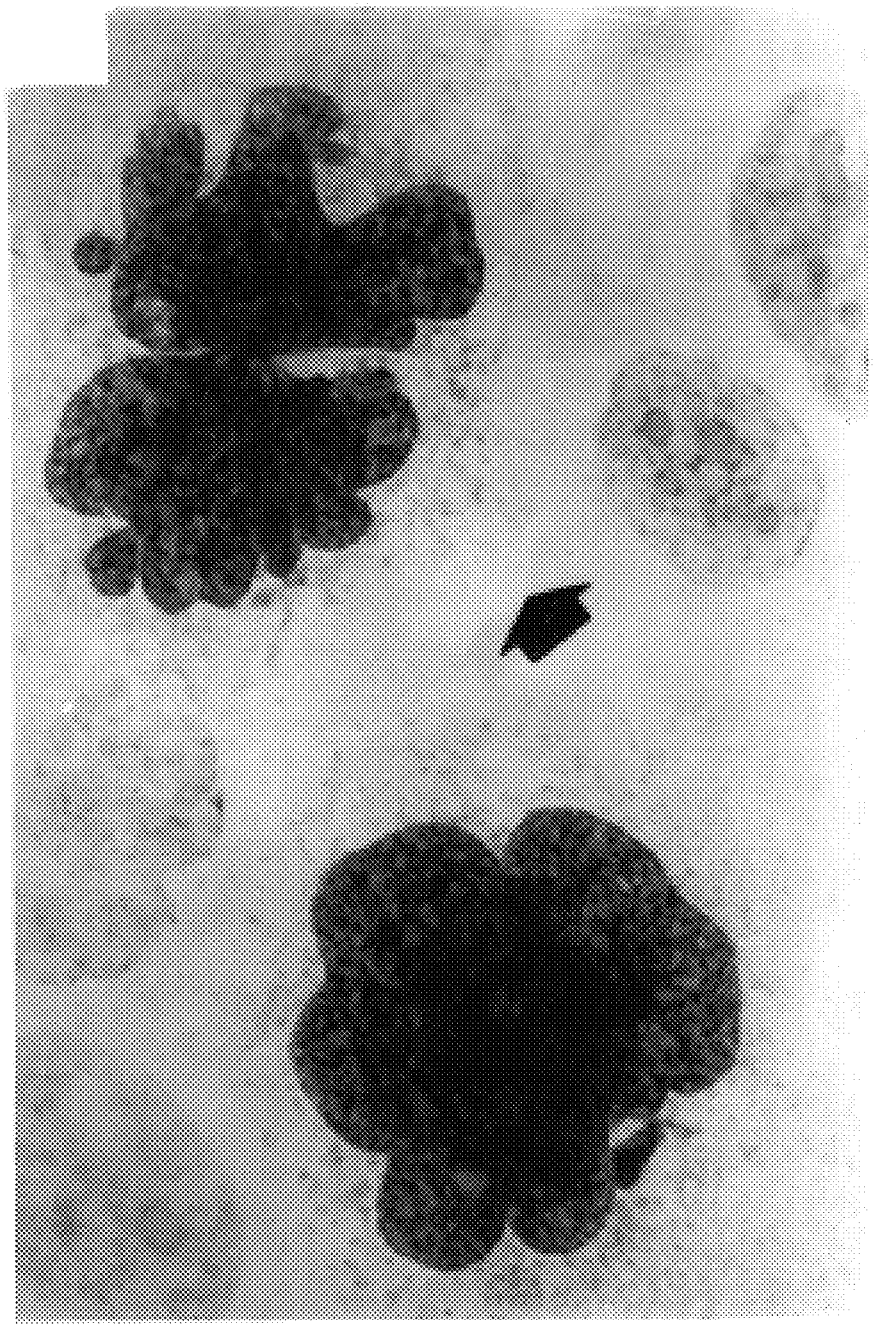

FIGS. 8A–8C: Horphological effects of p110$^{RB}$ and p94$^{RB}$ expression on RB-defective bladder carcinoma cell line 5637 (ATCC HTB9): panel A is mock-transfected HTB9 cells; panel B is p110$^{RB}$ expressing HTB9 transfectants; panel C is p94$^{RB}$-expressing HTB9 transfectants. Arrows indicate examples for RB-positive immunostained cells. Note that the p110$^{RB}$ expressing cells of panel B appear normal, but that the p94$^{RB}$ expressing cells of panel C are senescent.

Figure 9:
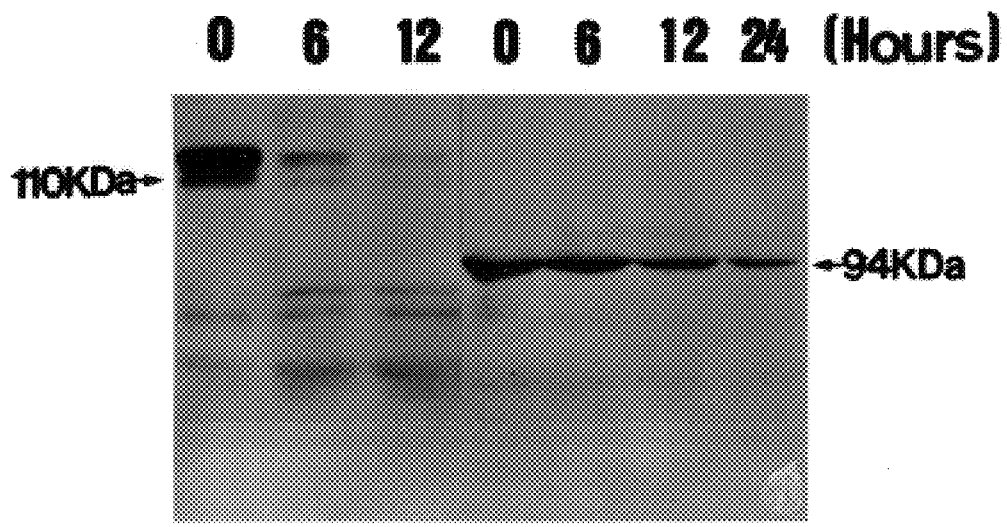

FIG. 9. Half-life analysis of p110$^{RB}$ and p94$^{RB}$ proteins in RB-reconstituted bladder carcinoma cell line, 5637. The bladder tumor cells were transfected in multiple dishes with either p110$^{RB}$ (pβA-f-RB33) or p94$^{RB}$ (pβA-s-RB34) expression plasmids. Twenty-four hours after transfection the cells were labeled with [$^{35}$S]-methionine and chased with excess unlabeled methionine for 0, 6, 12 and 24 hours, respectively The p110$^{RB}$ and p94$^{RB}$ proteins were determined by immunoprecipitation: the left side of the FIGS. 6A and 6B (0–12 hours) shows the half-life of p110$^{RB}$ is less than 6 hours; the right side of the figure (0–24 hours) shows the half-life of p94$^{RB}$ is about 12 hours.

Figure 10:
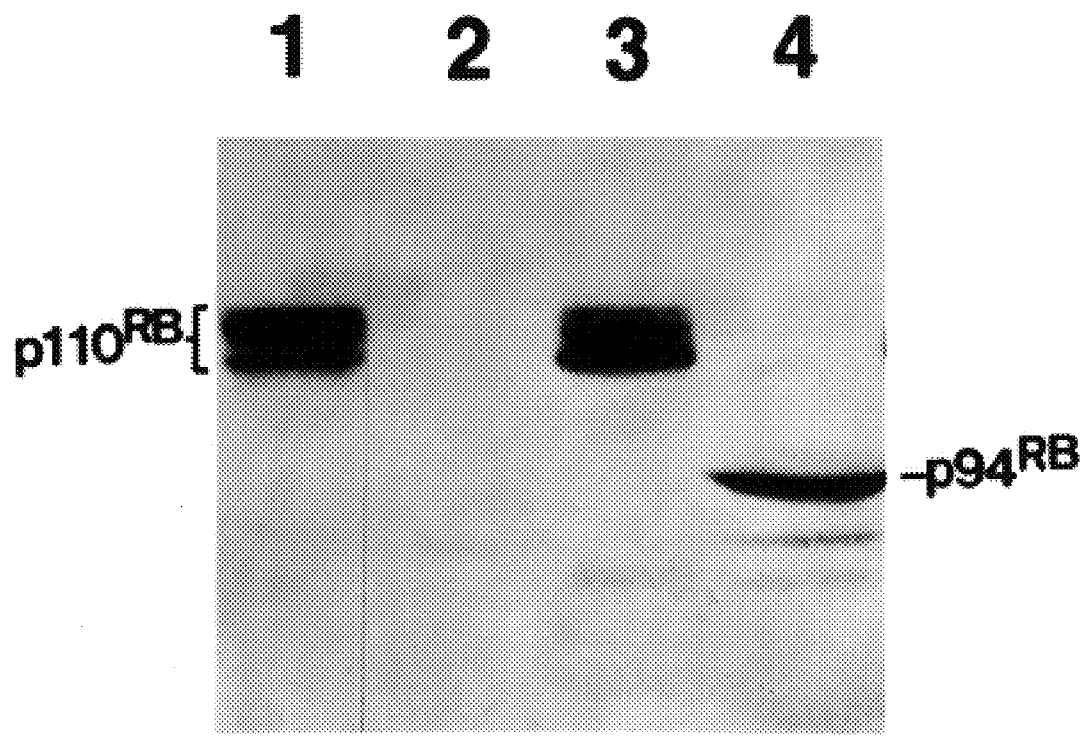

FIG. 10. Western blot analysis of exogenous p110$^{RB}$ and p94$^{RB}$ proteins in transiently transfected 5637 cells showing the distinct underphosphorylation state of the p94$^{RB}$ protein: lane 1 shows normal human fibroblast cell line, WI-38; lane 2 shows parental RB-minus bladder carcinoma cell line, 5637; lane 3 shows 5637 cells transfected with p110$^{RB}$-expressing plasmid; lane 4 shows 5637 cells transfected with p94$^{RB}$-expressing plasmid.

3.3 The Invention

The present invention is based upon the unexpected discovery that p94$^{RB}$ expressed by an expression vector in any abnormally proliferating target cell, e.g., a cancer or tumor cell, causes that suppressing the abnormal proliferation. Surprisingly, the treatment has been effective with all tested tumor cell lines and is not limited to treatment of RB-minus tumor cells.

Without wishing to be bound by a particular hypothesis or proposed mechanism of action, it is believed that the p94$^{RB}$ protein remains in the active, under phosphorylated form, and has a half-life in the target cell which is two to three times longer than that of p110$^{RB}$. Thus, it is possible that a synergistic combination of accumulation of p94$^{RB}$ together with its tendency to remain in an underphosphorylatede, active form serves to terminate the cell replication cycle in target tumor cells. However, whatever the mechanism of action, the property of suppressing cell growth and inducing senescence or killing any abnormally proliferating cell, irrespective of its genetic defect, is nevertheless completely unanticipated and unexpected.

In order to obtain the broad-spectrum tumor suppressor protein, a gene coding for the second inframe AUG codon-initiated RB protein, i.e., p94$^{RB}$, was expressed by a baculovirus vector in insect host cells as a stable nuclear phosphoprotein. The resulting unphosphorylated forms of p94$^{RB}$ were able to form a specific complex with SV40 T antigen, providing an important verification that the p94$^{RB}$ protein shares many functional properties of the naturally occurred p110$^{RB}$ protein, i.e., phosphorylation, viral oncoprotein association and nuclear tethering (Templeton et al., 1991, Proc. Natl. Acad. Sci., USA, 88:3033–3037).

The effects of transfection by either first or second in-frame AUG codon-initiated RB protein expression plasmid were compared on a number of well known human tumor cell lines. The tested cell lines included: an RB-defective human bladder carcinoma cell line, 5637 (ATCC HTB9); RB-defective human breast carcinoma cell line, MDA-MB-468 (ATCC HTB132); RB-defective human non-small cell lung carcinoma cell line, H2009 (Kratzke, R. A. et al., 1992, The Journal of Biological Chemistry, 267:25998–26003); RB-defective human prostate carcinoma cell line, DU145 (ATCC HTB81); RB-defective human osteosarcoma cell line, Saos-2 (ATCC HTB85); RB-defective human fibrosarcoma metastatic to lung cell line, Hs913T (ATCC HTB152); human cervix adenocarcinoma cell line, HeLa (ATCC CCL2) and human fibrosarcoma cell line, HT1080 (ATCC CCL121). Both the HeLa and HT1080 cell lines have normal p110$^{RB}$ expression. Each of these cell lines were separately transfected with the p110$^{RB}$ coding and the p94$^{RB}$ coding expression plasmids. The results demonstrated that the second in-frame AUG codon-initiated RB protein, p94$^{RB}$, was a more effective cell growth inhibitor, causing those dividing tumor cells to senesce and die. On the other hand, most normal human cells in vivo are either non-dividing or have the potential to progress into the cell cycle after a long latency period. Therefore, p94$^{RB}$, as an active cell cycle regulatory factor and a therapeutic reagent is expected to show little or no toxicity when transiently expressed in normal cells in vivo.

The study also demonstrated that the RB-minus tumor cells expressing-the second in-frame AUG codon-initiated RB protein, p94$^{RB}$, did not progress through the cell cycle, as evidenced by their failure to incorporate [$^3$H]-thymidine into DNA. However, the percentage of cells undergoing DNA replication was only slightly lower in cells producing the intact RB protein (p110$^{RB}$) than in cells that were RB-negative.

Of particular interest was the fact that the RB-defective bladder carcinoma cell line, 5637, failed to phosphorylate the second in-frame AUG codon-initiated RB protein as shown by Western blot analysis. In contrast, the intact RB protein (p110$^{RB}$) expressed in transfected 5637 cells were fully phosphorylated. Moreover, the half-life of the second in-frame AUG codon-initiated RB protein, p94$^{RB}$, was shown to be two-to three-fold greater than the intact RB protein (p110$^{RB}$). Therefore, the accumulation of only unphosphorylated (active) p94$^{RB}$ proteins may account for the failure of transiently transfected 5637 tumor cells to enter S phase, and this in turn may cause these tumor cells to senesce and die.

Both the fibrosarcoma cell line, HT1080 and cervix carcinoma cell line, HeLa, which have normal RB gene expression, were also successfully treated with the second in-frame AUG codon-initiated RB protein (p94$^{RB}$) expression plasmid, demonstrating that expression of the p94$^{RB}$ protein in RB+ cancer or tumor cells significantly suppressed the tumor cell growth. Therefore, an advantage of the present invention is that the methods and products herein disclosed can be used for therapeutic treating tumors having no specific tumor suppressor gene defects, which provides a significant advantage over previous techniques for human tumor suppressor gene therapy.

Table 1, on the following page, provides a summary of the identification of the tested tumor cell lines, their tumor origin and genetic defects.

TABLE 1

The Status of Antioncogenes (Tumor Suppressor Genes) and Oncogenes in p94$^{RB}$-Treated Human Tumor Cells

| RECIPIENT CELLS | TUMOR ORIGIN | ANTIONCOGENES | | ONCOGENES |
|---|---|---|---|---|
| | | RB | p53 | |
| 5637 | Bladder carcinoma, primary tumor | Negative | Mutation | |
| DU145 | Prostate carcinoma, metastasis to brain | Point mutation | Mutation | |
| MDA-MB-468 | Breast Carcinoma | Large deletion | Mutation | |
| H2009 | Lung carcinoma | Mutation | Mutation | |
| Hs913T | Fibrosarcoma, metastasis to lung | Large deletion | Negative | |
| Saos2 | Osteosarcoma, primary tumor | Large deletion | Negative | |
| HeLa | Cervix carcinoma, primary tumor | Normal | Negative | c-myc activation[1] |
| HT1080 | Fibrosarcoma, primary tumor | Normal | Normal | N-ras and c-yes-1 activation[2,3] |

[1]Durst, M., et al, Papillomavirus sequences integrate near cellular oncogenes in some cervical carcinomas. Proc. Natl. Acad. Sci., USA, 84(4):1070–1074, 1987.
[2]Brown, R., et al. A mechanism of activation of an N-ras gene in the human fibrosarcoma cell line HT1080. EMBO J., 3:1321–1326, 1984.
[3]Sugawara, K., et al. Distribution of c-yes-1 gene product in various cells and tissues. Br. J. Cancer, 63(4):508–513, 1991.

3.3.1. Preparation of RB$^{94}$ Vectors
3.3.1.1. Therapeutic Vectors

Any of the methods known to the art for the insertion of DNA fragments into a vector, as described, for example, in Maniatis, T, Fritsch, E. F., and Sambrook, J. (1989): *Molecular Cloning (A Laboratory manual)*, Cold Spring Harbor Laboratory, Cold Spring Harbor, New York; and Ausubel, F. M., Brent, R., Kingston, R. E., Moore, D. D., Seidman, J. G., Smith, J. A., and Struhl, K. (1992): *Current Protocols in Molecular Biology*, John Wiley & Sons, New York, may be used to construct p94$^{RB}$ encoding gene expression vectors consisting of appropriate transcriptional/translational control signals and the desired RB cDNA sequence downstream from the first in-frame AUG codon, that is unable to code for p110$^{RB}$. These methods may include in vitro DNA recombinant and synthetic techniques and in vivo genetic recombination. Expression of a nucleic acid sequence encoding a p94$^{RB}$ may be regulated by a second nucleic acid sequence so that the p94$^{RB}$ is expressed in a host infected or transfected with the recombinant DNA molecule. For example, expression of p94$^{RB}$ may be controlled by any promoter/enhancer element known in the art. The promoter activation may be tissue specific or inducible by a metabolic product or administered substance.

Promoters/enhancers which may be used to control p94$^{RB}$ gene expression include, but are not limited to, the native RB promoter, the cytomegalovirus (CMV) promoter/enhancer (Karasuyama, H., et al., 1989, *J. Exp. Med.*, 169:13), the human β-actin promoter (Gunning, P., et al., 1987, *Proc. Natl. Acad. Sci. USA*, 84:4831–4835), the glucocorticoid-inducible promoter present in the mouse mammary tumor virus long terminal repeat (HHTV LTR) (Klessig, D. F., et al., 1984, *Mol. Cell Biol.*, 4:1354–1362), the long terminal repeat sequences of Holoney murine leukemia virus (MULV LTR) (Weiss, R., et al., 1985, *RNA Tumor Viruses*, Cold Spring Harbor Laboratory, Cold Spring Harbor, New York), the SV40 early region promoter (Bernoist and Chambon, 1981, *Nature* 290:304–310), the promoter contained in the 3' long terminal repeat of Rous sarcoma virus (RSV) (Yamamoto et al., 1980, *Cell* 22:787–797), the herpes simplex virus (HSV) thymidine kinase promoter/enhancer (Wagner et al., 1981, *Proc. Natl. Acad. Sci. U.S.A.* 78:1441–1445), the regulatory sequences of the metallothionein gene (Brinster et al., 1982, *Nature* 296:39–42), the adenovirus promoter (Yamada et al., 1985, *Proc. Natl. Acad. Sci. U.S.A.* 82(11):3567–71), and the herpes simplex virus LAT promoter (Wolfe, J. H., et al., 1992, *Nature Genetics*, 1:379–384).

Expression vectors compatible with mammalian host cells for use in genetic therapy of tumor or cancer cells, include, but are not limited to: plasmids, retroviral vectors, adenovirus vectors, herpes viral vectors, and non-replicative avipox viruses, as disclosed, for example, by U.S. Pat. No. 5,174,993.

In a specific embodiment, a plasmid vector derived from pHβAPr-1-neo, was constructed for expression of p94$^{RB}$ in mammalian cells by placing the coding sequence for p94$^{RB}$ under control of the human β-actin gene promoter (Gunning, P. et al., *Proc. Natl. Acad. Sci., USA*, 1987, 84:4831–4835).

In another specific embodiment, a plasmid vector derived from pCHV-Neo-Bam (Baker, S. J., et al., *Science*, 1990, 249:912–915), was constructed for expression of p94$^{RB}$ in mammalian cells by placing the coding sequence for p94$^{RB}$ under control of the cytomegalovirus (CMV) promoter/enhancer sequences.

In another specific embodiment, a retroviral vector, pLL-RNL (Miller, A. D., et al., 1985, *Proc. Natl. Acad. Sci., USA*, 5:431) is used to construct a vector able to transduce mammalian cells and express p94$^{RB}$ protein under the control of the MULV LTR promoter, the CKV promoter, the β-actin promoter or any other effective promoter.

In yet another specific embodiment, an adenovirus type 5 (Ad5) deletion mutant, Ad-d1324, and a plasmid, pTG5955 (Rosenfeld, M. A., et al., *Cell*, 1992, 68:143–155) are used to construct an adenovirus vector able to infect mammalian cells and express p94$^{RB}$ protein under the control of the adenovirus type 2 (Ad2) major late promoter, the CHV promoter, the β-actin promoter or any other effective promoter.

3.3.1.2. Vectors for Production and Purification of p94$^{RB}$ Protein

Alternatively, expression vectors compatible with host cells suitable for production of p94$^{RB}$ may be constructed to express p94$^{RB}$ protein in those compatible host cells. These include but are not limited to mammalian cells infected with a virus (e.g., adenovirus, retrovirus, herpes simplex virus, avipox virus); insect cells infected with a virus (e.g., baculovirus); microorganisms such as yeasts containing yeast vectors, or bacteria transformed with bacteriophage DNA, plasmid DNA, or cosmid DNA. The expression controlling elements of vectors vary in their strengths and specifications Depending on the host-vector system utilized, any one of a number of suitable transcription and translation elements may be used. The produced $p94^{RB}$ may be purified from host cells by affinity chromatography, electrophoresis, high-performance liquid chromatography (HPLC) or any other methods known to the art.

In a specific embodiment an engineered derivative of *Autographa California* Multiple Nuclear Polyhedrosis Virus ("AcMNPV") was used to produce $p94^{RB}$ protein in cultured Fall Army worm *Spondoptera frugiperda* cells (Sf9 cells) with a strong temporally regulated promoter of the polyhedron gene whose product represents 50% or more of total cellular proteins during a lytic infections. The baculovirus-expressed $p94^{RB}$ protein was subsequently purified by immunoaffinity chromatography.

3.3.1.3. Detection of $p94^{RB}$ Coding Expression Vectors

Expression vectors containing $p94^{RB}$ coding inserts can be identified by three general approaches: (a) nucleic acid hybridization, (b) presence or absence of "marker" gene functions, and (c) expression of inserted sequences. In the first approach, the presence of a $p94^{RB}$ coding gene inserted in an expression vector can be detected by nucleic acid hybridization using probes comprising sequences that are homologous/complementary to the inserted $p94^{RB}$ coding gene. Such hybridization can be carried out under stringent or nonstringent conditions, depending upon the size and sequence of the probe selected. In the second approach, the expression vector/host system can be identified and selected based upon the presence or absence of certain "marker" gene functions (e.g., thymidine kinase activity, resistance to antibiotics, viral occlusion formation in a baculovirus vector infected insect cell, etc.) caused by introduction of the expression vector into the host cell. For example, if the $p94^{RB}$ coding gene is inserted within a vector having a dominant selectable marker gene, such as a neomycin phosphotransferase gene under separate control of an appropriate promoter, such as an SV40 early promoter, the expression vector containing the $p94^{RB}$ coding gene can be identified by the presence of the marker gene function (geneticin resistance). In the third approach, expression vectors containing a $p94^{RB}$ coding gene can be identified by assaying the $p94^{RB}$ coding gene products expressed by the vectors. Such assays can be based, for example, on the physical or functional properties of the $p94^{RB}$ gene products in in vitro or in vivo assay systems including metabolic radiolabelling by [$^{35}$S] methionine, SDS-polyacrylamide gel electrophoresis, binding with a specific antibody, and phosphorylation by a protein kinase.

3.3.2. Expression of $p94^{RB}$

An appropriate $p94^{RB}$ coding expression vector, i.e., a vector which contains the necessary elements for the transcription and translation of the $p94^{RB}$ protein-coding sequence may be introduced into a host cell. A host cell may be any cell type compatible with the vector for expressing and producing $p94^{RB}$. In a preferred embodiment, the host cell is a mammalian tumor cell to be treated. In a more preferred embodiment, the host cell is a human tumor cell to be treated. Expression of the $p94^{RB}$ in a host cell may be transient, permanent, or inducible.

The necessary transcriptional and translational signals, including promoter/enhancer sequences can also be supplied by the native RB gene and/or its flanking regions. A variety of vector/host systems may be utilized to express the $p94^{RB}$ protein-coding sequence in a tumor cell to be treated. These include but are not limited to mammalian cell systems transfected, infected or transduced with a plasmid, or a virus (e.g., adenovirus, retrovirus, herpes simplex virus, avipox virus). The expression elements of vectors vary in their strengths and specificities. Depending on the host cell to be treated, any one or more of a number of suitable transcription and translation elements may be used.

3.3.3. Methods of Treatment

The $p94^{RB}$ encoding gene construct of the present invention may be placed by methods well known to the art into an expression vector such as a plasmid or viral expression vector. A plasmid expression vector may be introduced into a tumor cell by calcium phosphate transfection, liposome (for example, LIPOFECTIN)-mediated transfection, DEAE Dextran-mediated transfection, polybrene-mediated transfection, electroporation, and any other method of introducing DNA into a cell.

A viral expression vector may be introduced into a target cell in an expressible form by infection or transduction. Such a viral vector includes, but is not limited to: a retrovirus, an adenovirus, a herpes virus and an avipox virus. When $p94^{RB}$ is expressed in any abnormally proliferating cell, the cell replication cycle is arrested, thereby resulting in senescence and cell death and ultimately, reduction in the mass of the abnormal tissue, i.e., the tumor or cancer. A vector able to introduce the gene construct into a target cell and able to express $p94^{RB}$ therein in cell proliferation-suppressing amounts can be administered by any effective method.

For example, a physiologically appropriate solution containing an effective concentration of active vectors can be administered topically, intraocularly, parenterally, orally, intranasally, intravenously, intramuscularly, subcutaneously or by any other effective means. In particular, the vector may be directly injected into a target cancer or tumor tissue by a needle in amounts effective to treat the tumor cells of the target tissue.

Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the cancer or tumor afflicted hollow organ. Any effective imaging device such as X-ray, sonogram, or fiberoptic visualization system may be used to locate the target tissue and guide the needle or catheter tube.

In another alternative, a physiologically appropriate solution containing an effective concentration of active vectors can be administered systemically into the blood circulation to treat a cancer or tumor which cannot be directly reached or anatomically isolated.

In yet another alternative, target tumor or cancer cells can be treated by introducing $p94^{RB}$ protein into the cells by any known method. For example, liposomes are artificial membrane vesicles that are available to deliver drugs, proteins and plasmid vectors both in vitro or in vivo (Mannino, R. J. et al., 1988, *Biotechniques*, 6:682–690) into target cells (Newton, A. C. and Huestis, W. H., *Biochemistry*, 1988, 27:4655–4659; Tanswell, A. K. et al., 1990, *Biochmica et Biophysica Acta*, 1044:269–274; and Ceccoll, J. et al. *Journal of Investigative Dermatology*, 1989, 93:190–194). Thus, $p94^{RB}$ protein can be encapsulated at high efficiency with liposome vesicles and delivered into mammalian cells in vitro or in vivo.

Liposome-encapsulated $p94^{RB}$ protein may be administered topically, intraocularly, parenterally, intranasally, intratracheally, intrabronchially, intramuscularly, subcutaneously or by any other effective means at a dose efficacious to treat the abnormally proliferating cells of the target tissue. The liposomes may be administered in any physiologically appropriate composition containing an effective concentration of encapsulated $p94^{RB}$ protein.

3.3.4. Tumors Susceptible To Treatment

The gene construct and vectors of the present invention are effective in inhibiting the growth or mitosis or both of any type of tumor cell. The gene construct of the invention has demonstrated effectiveness in treating tumor cells of carcinomas and sarcomas. In particular, the gene construct of the invention has demonstrated effectiveness in suppressing replication and inducing cell senescence followed by cell death in the following tumor cell types: bladder carcinoma, lung carcinoma, breast carcinoma, prostate carcinoma, fibrosarcoma, osteosarcoma and cervix carcinoma.

Further, the gene construct of the invention has demonstrated effectiveness in suppressing replication and inducing cell senescence followed by cell death in the tumor cells having the following identified genetic defects: tumor suppressor gene RB and p53 mutation, oncogene myc activation, and oncogene N-ras and c-yes-1 activation.

Furthermore, the gene construct of the invention has demonstrated effectiveness in suppressing replication and inducing cell senescence followed by cell death in the tumor cells having normal endogenous tumor suppressor $RB^{110}$ and/or p53 gene expression.

In addition, the gene construct of the invention is able to suppress replication in lymphomas, leukemia and in tumor cells having tumor suppressor gene DCC and NF1 genetic defects, as well as in other tumor cell types in which the genetic defects are unknown or have yet to be identified.

3.3.5. Ex Vivo Treatment of Tumor or Cancer Tissues

In a preferred embodiment a tumor cell is transduced with a retrovirus vector, an adenovirus vector, a plasmid vector or any other appropriate vector capable of expressing the $p94^{RB}$ protein in that tumor cell. The cancer cell may be present in a blood or bone marrow sample collected from a leukemia patient. A dose of $p94^{RB}$ protein expressing retrovirus vector or adenovirus vector or plasmid vector or any other appropriate vector is administered to the sample of blood or bone marrow at a dose sufficient to transduce enough cells in the sample to produce a reduction in tumor cell numbers. The cell proliferation of the treated cancer cells will be slowed or terminated followed by a process similar to normal cellular differentiation or cell senescence. Analo-gously, blood or bone marrow or other tissue is treated ex vivo using an effective dose of a lipsome-encapsulated $p94^{RB}$ protein. Thereafter the sample may be returned to the donor or infused into another recipient.

3.3.6. In Vivo Treatment of Tumor or Cancer Tissues

Methods of administering viral vectors are well known. In general, the skilled artisan will appreciate that a retroviral vector, an adenovirus vector, a plasmid vector, or any other appropriate vector capable of expressing the $p94^{RB}$ protein can be administered in vivo to a cancer by a wide variety of manipulations. All such manipulations have in common the goal of placing the vector in sufficient contact with the target tumor to permit the vector to transduce or transfect the tumor cells. In a preferred embodiment, cancers present in the epithelial linings of hollow organs may be treated by infusing the vector suspension into a hollow fluid filled organ, or by spraying or misting into a hollow air filled organ. Thus, the tumor cell may be present in or among the epithelial tissue in the lining of pulmonary bronchial tree, the lining of the gastrointestinal tract, the lining of the female reproductive tract, genitourinary tract, bladder, the gall bladder and any other organ tissue accessible to contact with the vector.

In another preferred embodiment, the cancer may be located in or on the lining of the central nervous system, such as, for example, the spinal cord, spinal roots or brain, so that vectors infused in the cerebrospinal fluid will contact and transduce the cells of the tumor in that space.

In another preferred embodiment, the cancer is a solid tumor. The skilled artisan will appreciate that the vector can be administered to the tumor by direct injection of the vector suspension into the tumor so that vectors will contact and transduce or transfect the tumor cells inside the tumor.

In yet another preferred embodiment, the cancer may be a cancer of the blood, blood forming organs or any organ directly perfused by the blood, so that vectors injected into the blood stream will contact and treat the cells of the cancer. Thus, the cancer may be a leukemia, a lymphoma or other tumor type and the tumor cell may be present in the blood, the bone marrow, the spleen, the thymus, the liver and any other blood perfused organ.

The skilled artisan will understand that the vector is administered in a composition comprising the vector together with a carrier or vehicle suitable for maintaining the transduction or transfection efficiency of the chosen vector and promoting a safe infusion. Such a carrier may be a pH balanced physiological buffer, such as a phosphate, citrate or bicarbonate buffers a saline solution, a slow release composition and any other substance useful for safely and effectively placing the vector in contact with abnormally proliferating cells to be treated.

The invention is further described in the following examples which are in no way intended to limit the scope of the invention.

4. EXAMPLES 4.1 Preparation of Vectors for Expression of the Second In-Frame AUG Codon-Initiated RB Protein in Insect Cells The engineered derivatives of *Autographa california* Multiple Nuclear Polyhedrosis Virus ("AcMNPV") have been widely employed to produce high levels of accurately processed and biologically active proteins. This baculovirus propagates in cultured Fall Army worm *Spondoptera frugiperda* cells (Sf9 cells) and has a strong temporarily regulated promoter of the polyhedron gene whose product represents 50% or more of total cellular proteins during a lytic infection.

By in vivo recombination the coding sequence of a foreign gene can easily be placed under the transcriptional control of the polyhedron promoter, resulting in a high level of expression. In addition, such proteins may be correctly folded and contain appropriate post-translational modifications like those proteins in the native higher eukaryotes.

By site-specific mutagenesis, two BamH1 sites were introduced into the RB cDNA at nucleotides +7 and +3230 (the A of the second in-frame AUG codon is designated +19). The resulted DNA molecule has the nucleotide sequence of FIG. 1A–1F (SEQ ID NO:1; SEQ ID NO:2), which is also referred to herein as the second in-frame AUG codon-initiated RB protein gene, or the $p94^{RB}$ encoding gene. The coded-for protein has the sequence of FIG. 2A–2F (SEQ ID NO:3) and is referred to herein as the second in-frame AUG codon-initiated RB protein, or the $p94^{RB}$ protein.

In an attempt to achieve maximal production of the second in-frame AUG codon-initiated RB protein in the baculovirus expression system, the recombinant transfer vector was constructed with insertion of the p94$^{RB}$ gene into the pVL1393 plasmid so that the p94$^{RB}$ gene was placed under the control of the polyhedron gene promoter.

As shown in FIG. 3, the resulting pVL-s-RB plasmid contains no additional AUG start codon upstream from the p94$^{RB}$ translation initiation site at nucleotide +19, and thus encodes a nonfusion p94$^{RB}$ protein. In a parallel study, the same strategy was employed to construct a p110$^{RB}$ expression vector which was designated pVL/1st AUG-RB.

Transfer of RB cDNAs from the recombinant vectors to the viral genome was accomplished by co-transfecting wild-type AcMNPV virus DNA with pVL-s-RB plasmid DNA or pVL/1st AUG-RB plasmid DNA. The recombinant viruses were subjected to three rounds of plaque purification to obtain a pure stock of RB-containing baculovirus, designated AcMNPV-RB94 and ACMNPV-RB100, respectively.

4.2 Purification of p110$^{RB}$ and p94$^{RB}$ Proteins

The p110$^{RB}$ and p94$^{RB}$ proteins were purified from baculovirus-infected insect cells by immunoaffinity chromatography. Briefly, insect cells were harvested 24 hours after the virus infection and lysed at 4° C. with EBC buffer (50 mN Tris-HCl, pH8.0, 120 mH NaCl, 0.5% NP-40, 50 µg/ml aprotinin). The lysate was clarified by centrifugation and the p110$^{RB}$- or p94$^{RB}$-containing supernatant was incubated with biotinylated WL-1 polyclonal anti-RB antibodies (Xu, H-J., et al., 1989, *Oncogene*, 4.807–812) at 4° C. overnight. The procedures for biotinylation of rabbit IgGs using succinimide ester followed the methods described by Bayer and Wilchek (Baylor, E. A. and Wilchek, M., 1980, *Methods Biochem. Anal.*, 26:1–45). The RB protein-IgG-biotin complex was collected on a streptavidin agarose gel column. Purified p110$^{RB}$ or p94$^{RB}$ were eluted from separate columns using 100 mM glycine (pH 2.2) and neutralized with 1M of phosphate (pH 8.0).

4.2.1. p94$^{RB}$ Shares Major Biochemical and Biological Properties With p110$^{RB}$ Since non-functional mutations of the retinoblastoma protein are characterized by defects in phosphorylation, viral oncoprotein association and nuclear localization (Templeton et al., 1991, *Proc. Natl. Acad. Sci., USA*, 88:3033–3037), the functional aspects of the artificial p94$^{RB}$ protein were studied for these characteristics.

Figure 4A:
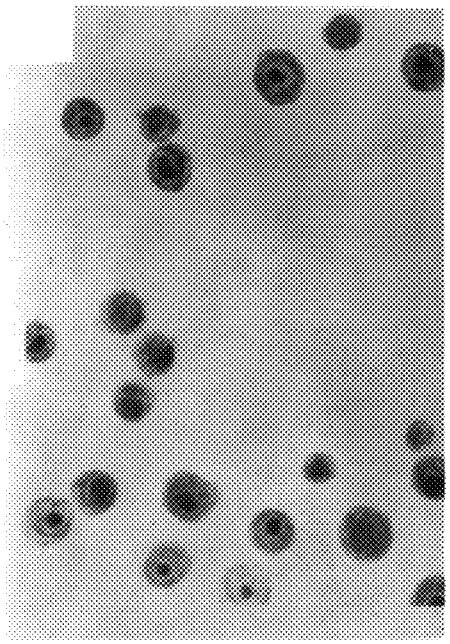
Figure 4B:
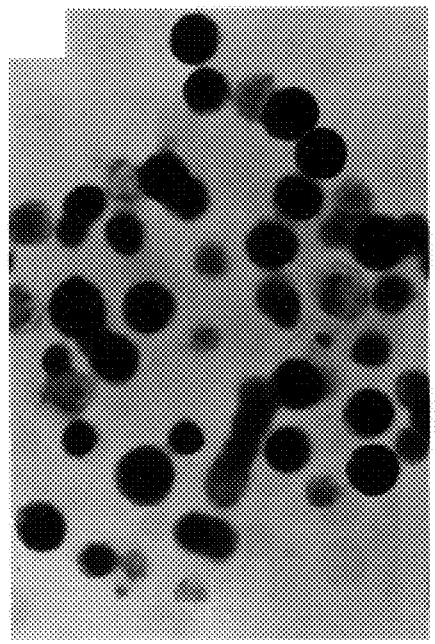
Figure 4C:
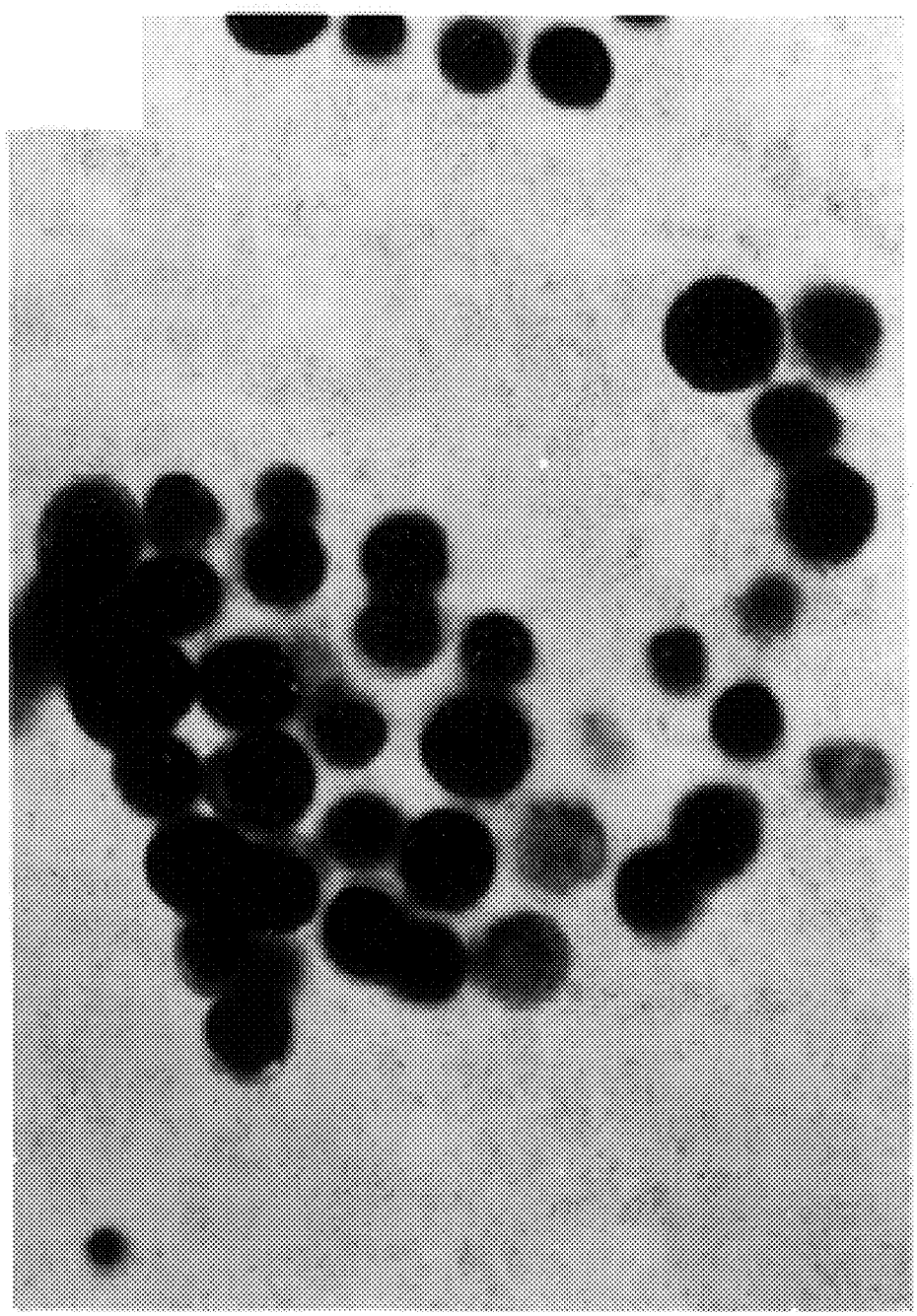

First, to determine whether the RB proteins produced in the insect cells with the baculoviruses were associated with the nucleus, the AcMNPV-RB110 and AcMNPV-RB94 infected Sf9 cells were immunostained with MAb-1 anti-RB monoclonal antibody 24 h after infection. As shown in FIG. 4A–4C, intense staining was found exclusively in the nuclei of cells infected with either AcHNPVRBI10 (panel B) or AcMNPV-RB94 (panel C).

The p110$^{RB}$ and p94$^{RB}$ proteins purified from baculovirus-infected insect cells by immunoaffinity chromatography were tested for their ability to form a specific complex with SV40 T antigen. Briefly, equal amounts of p94$^{RB}$ or p110$^{RB}$ and T antigen were mixed and aliquots of the mixture were immunoprecipitated with PAB419 anti-T antibody. As shown in FIG. 5, mixing of p94$^{RB}$ (or p110$^{RB}$) with T antigen in vitro resulted in the co-immunoprecipitation of both under- and hypo-phosphorylated p94$^{RB}$ (lane 5), or p110$^{RB}$ (lane 3) with PAB419. The data demonstrated that either p110$^{RB}$ or p94$^{RB}$ protein can form a specific complex with SV40 T antigen. The AcMNPV-RB94 virus-infected insect cells appear to make hyperphosphorylated p94$^{RB}$ (lane 4), which was unable to form complexes with SV40 T antigen (compare lane 4 with lane 5).

The Western blot shown in FIG. 5 revealed an apparent relative molecular mass (Mr) of 94 kD for the second in-frame AUG codon-initiated RB protein. On SDS-PAGE, the p94$^{RB}$ protein (FIG. 5, lanes 4 and 5) was smaller than the naturally occurring 98 kDa proteins of unknown origin (Xu et al., 1989, *Oncogene*, 4:807–812) (FIG. 5, lane 1). Therefore, the second in-frame AUG codon-initiated RB protein of this invention (p94$^{RB}$) has not been found to occur naturally in human cells.

It is concluded that the second in-frame AUG codon-initiated p94$^{RB}$ protein produced in recombinant virus-infected insect cells is a artificial but stable nuclear phosphoprotein with its under- and hypo-phosphorylated forms being able to assemble specific complex with SV40 T antigen, as does the naturally occurring RB protein species, p110$^{RB}$.

4.3 Construction of Expression Vectors for Mammalian Cells 4.3.1. Subcloning of RB cDNA Fragments Encoding for the First and Second In-Frame AUG Codon-Initiated RB Proteins Subcloning of RB cDNA fragments encoding for the first and second in-frame AUG codon-Initiated RB proteins was accomplished by standard methods in the art. The methods for DNA manipulation were modified from Maniatis, T, Fritsch, E. F., and Sambrook, J. (1989): *Molecular Cloning (A Laboratory Manual)*, Cold Spring Harbor Laboratory, Cold Spring Harbor, N.Y.; and Ausubel, F. H., Brent, R., Kingston, R. E., Moore, D. D., Seidman, J. G., Smith, J. A., and Struhl, K. (1992). *Current Protocols in Molecular Biology*, John Wiley & Sons, New York.

4.3.2. Preparation of a DNA Molecule Encoding the Second In-Frame AUG Codon-Initiated RB Protein.

A plasmid, p4.95BT (Friend et al., 1987, *Proc. Natl. Acad. Sci. USA*, 84:9059–9063) or F7 (Takahashi, R., Hashimoto, T., Xu, H-J., et al., 1991; *Proc. Natl. Acad. Sci. USA*, 88:5257–5261) containing the full length retinoblastoma (RB) gene cDNA was digested with the restriction enzyme, Hind II, at nucleotide +7 and the restriction enzyme, ScaI, at nucleotide 3,230 (The A of the second in-frame AUG codon of the full length RB cDNA open reading frame was designated nucleotide +19). The resulted 3,230 bp RB cDNA fragment had two blunt ends. Conversion of the blunt ends to restriction enzyme BamHI sites was done by ligation of a synthetic BamHI oligonucleotide linker (GGGATCCC) to each blunt end of the fragment followed by digestion with the BamHI enzyme.

The desired RB cDNA fragment was inserted into the BamHI cloning site of a plasmid vector, pUC19, and propagated in the *Escherichia coli* strain, DH5 alpha bacterial cells. The recombinant plasmid was purified from a single DH5 alpha transformant and designated plasmid pUC-s-RB. This plasmid contains the desired RB cDNA fragment of 3,230 bp coding for the second in-frame AUG codon-initiated RB protein of 816 amino acids.

4.3.3. Preparation of A DNA Molecule Encoding the First In-Frame AUG Codon-Initiated RB Protein.

The full length RB cDNA plasmid was digested with the restriction enzyme, AcyI at nucleotide −322 and ScaI at nucleotide 3,230. The AcyI ends (overhang 5'-CG) were repaired by "filling in" the ends with the Klenow fragment of *E. coli* DNA polymerase I in the presence of all 4 dNTPs to generate blunt ends. Conversion of the blunt ends to restriction enzyme BamHI sites was done as described above. The resulted RB cDNA fragment of 3,552 bp was inserted into the plasmid pUC19 and propagated in the *Escherichia coli* strain DH5 alpha, which was subsequently purified from a single DH5 alpha transformant and designated plasmid pUC-f-RB. This plasmid contains the RB cDNA fragment of 3,552 bp coding for the first in-frame AUG codon-initiated RB protein of 928 amino acids.

4.3.4. Construction of p94$^{RB}$ Expression Plasmid Using A Human β-Actin Gene Promoter The RB cDNA fragment of 3,230 bp coding for the second in-frame AUG codon-initiated RB protein of 816 amino acids (p94$^{RB}$) was recovered from plasmid pUC-s-RB following the restriction enzyme, BamHI digestion, and re-inserted into the unique BamHI site of an expression plasmid, pHβAPr-1-neo (Gunning, P., et al., *Proc. Natl. Acad. Sci., USA,* 1987, 84:4831–4835) in a orientation that the p94$^{RB}$ coding sequence was under the direct control of the β-actin gene promoter. A plasmid vector with the correct insert orientation was selected by restriction endonuclease mapping after propagation in DH5 alpha *Escherichia coli* host cells, and was designated pβA-s-RB34 (FIG. 7B). The corresponding DH5 alpha strain that contains plasmids pβA-s-RB34 was thereafter designated DHB-s-RB34 (ATCC 69241, patent depository, American Type culture Collection).

The plasmid vector pβA-s-RB34 contains no additional AUG codon between the β-actin gene promoter and the second in-frame AUG codon of the RB coding sequence, and thus encodes a non-fusion p94$^{RB}$ protein. The plasmid vector pβA-s-RB34 also confers a dominant selectable marker (geneticin resistance) in eukaryotic cells through expression of the neomycin phosphotransferase (neo) under separate control of an SV40 early promoter (FIG. 7A and 7B, sv-neo).

4.3.5. Construction of p110$^{RB}$ Expression Plasmid Using A Human β-Actin Gene Promoter The RB cDNA fragment of 3,552 bp coding for the first in-frame AUG codon-initiated RB protein of 928 amino acids (p110$^{RB}$) was recovered from plasmid pUC-f-RB and re-inserted into the expression plasmid pHβAPr-1-neo downstream from the β-actin gene promoter. The resulting plasmid vector was designated pβA-f-RB33 (FIG. 7A). The plasmid vector pβA-f-RB33 contains no additional AUG codon between the β-actin gene promoter and the first in-frame AUG codon of the RB coding sequence, and thus encodes a non-fusion p110$^{RB}$ protein.

4.3.6. Construction of p94$^{RB}$ and p110$^{RB}$ Expression Plasmids Using A Cytomegalovirus Promoter (CMVp)

Alternatively, an expression plasmid, pCMV-Neo-Bam (Baker, S.J., et al., *Science,* 1990, 249,912–915) was used in place of plasmid pHβAPr-1-neo. The vector included cytomegalovirus (CMV) promoter/enhancer sequences, which could drive expression of the insert at the BamHI site, and splicing and polyadenylation sites derived from the rabbit β-globin gene, which ensured proper processing of the transcribed insert in the cells. A pBR322 origin of replication and β-lactamase gene facilitated propagation of the plasmid in *E. coli.* The plasmid conferred geneticin resistance (a selectable marker in eukaryotic cells) through expression of the neomycin phosphotransferase (neo) under the control of a herpes simplex virus (HSV) thymidine kinase promoter.

The same strategies as described supra in Sections 4.3.4 and 4.3.5 were employed to transfer the RB cDNA fragments of 3,230 bp and 3,552 bp from plasmids pUC-s-RB and pUC-f-RB, respectively, to the unique BamHI site in the expression vector, pCMV-Neo-Bam. The resulting plasmid vectors were designated by the names of pCMV-s-RB42, expressing the p94$^{RB}$ and pCMV-f-RB35, expressing the p110$^{RB}$ (FIGS. 6A and 6B). The corresponding *Escherichia coli* DH5 alpha strain which contains plasmids pCMV-s-RB42 was thereafter designated DHC-s-RB42 (ATCC 69240, patent depository, American Type Culture Collection).

4.3.7. Construction of p94$^{RB}$ Protein Expression Retrovirus Vectors

For this protocol, retroviral vector, PLLRNL (Miller, A. D., Law, M. F., Verma, I. M. *Molec. Cell Biol.,* 1985, 5:431) and amphotropic retrovirus packaging cell line, PA317 (ATCC CRL9078) (Miller, A. D., and Buttimore, C., *Molec. Cell Biol.,* 1986, 6:2895–2902) are used.

A plasmid p4.95BT or F7 containing the full-length RB gene cDNA is digested with the restriction enzyme Hind II at nucleotide +7 (the A of the second in-frame AUG codon of the full-length RB cDNA open reading frame was designated nucleotide +19). Conversion of the Hind II site to restriction enzyme Hind III site is done by ligation of a synthetic Hind III oligonucleotide linker (CCAAGCTTGG) to the blunt ends of the linear plasmid DNA, followed by digestion with the Hind III enzyme. The linear plasmid DNA is further digested with restriction enzyme, ScaI, at nucleotide 3,230. The resulted RB cDNA fragment of 3,230 bp codes for the second in-frame AUG codon-initiated RB protein of 816 amino acids (p94$^{RB}$). This fragment has a 5'-Hind III site (cohesive end) and a 3'-ScaI site (blunt end), which facilitates its insertion into the retroviral vector, pLLRNL.

The vector pLLRNL is digested with two sets of restriction enzymes: Hind III/ClaI and SmaI/ClaI to delete the luciferase gene Appropriate fragments are recovered from the agarose gel following electrophoresis, and ligated with the RB cDNA fragment of 3,230 bp to form a new vector, pLRB94RNL, in which the p94$^{RB}$ expression is under the control of the long terminal repeat sequences of Moloney murine leukemia virus (MuLV LTRs).

The basic protocol for construction of the retroviral vector, pLRB94RNL, is modified from Huang, H.-J.S. et al., 1988, *Science,* 242:1563–1566.

Alternatively, the vector pLLRNL is digested with a single restriction enzyme, Hind III, to delete the luciferase gene, as well as the Rous sarcoma virus promoter (RSV). An appropriate DNA fragment is recovered from the p94$^{RB}$ expression plasmid, pCHV-s-RB42 (or pβA-s-RB34). The recovered DNA fragment, which contains the 3,230 bp RB cDNA fragment and 5'-flanking CMV promoter (or β-actin promoter), is inserted into the ClaI restriction site of the retroviral vector. Conversion between the restriction enzyme sites is done by the methods as described supra in Section 4.3.7.

In the resulting p94$^{RB}$ expression retrovirus vector, the p94$^{RB}$ gene is under the control of an internal promoter (the CMV promoter or β-actin promoter), while the Tn5 neomycin-resistance gene (Neo) is under the control of the MuLV LTRs.

A safe and efficient amphotropic packaging cell line is necessary for transfer of retroviral vector genes into human cancer cells. The virus packaging methods are modified from the method of Miyanohara et al., *Proc. Natl. Acad. Sci., USA,* 1988, 85:6538–6542. For this protocol, the PA317 packaging cell line is used. This packaging cell line has received prior approval for use in human gene therapy clinical trials.

The retroviral vector (pLRB94RKL) DNA is transfected into PA317 packaging cells by LIPOFECTIN reagent (GIBCO BRL Life Technologies, Inc., Gaithersburg, Md.) or electroporation methods as described in Sections 4.4.1.

infra. Single colonies are isolated by selection in G418-containing medium (400 μg/ml) and expanded into mass cultures. To titer the virus produced by selected PA317 clones, dilutions of cell-free culture medium from each PA317 clone are applied to 208F rat fibroblasts (indicator cells) in the presence of POLYBRENE (Sigma, 4 μg/ml) and G418 selection (400 μg/ml) is started 24 hours after infection.

After two weeks, G418-resistant colonies are visualized by Giemdetermined (col viral titers are determined (colony-forming units per milliliter, cfu/ml). PA317 clones producing high virus titers are then assayed for human p94$^{RB}$ protein expression by Western immunoblotting as described previously (Xu, H.-J., et al., *Oncogene*, 1991, 6:1139–1146). Cell-free culture media from selected PA317 clones expressing high level of human p94$^{RB}$ protein are then applied to human cancer cells ex vivo or in vivo.

4.3.8. Construction of p94$^{RB}$ Protein Expression Adenovirus Vectors

The recombinant adenovirus Ad-RB94 is constructed from the adenovirus type 5 (Ad5) deletion mutant, Ad-d1324, and a plasmid, pTG5955, in which the human CFTR cDNA has been replaced by the human RB cDNA fragment of 3,230 bp coding for the p94$^{RB}$ protein. The plasmid pTG5955 containing the RB cDNA insert is linearized by restriction enzyme ClaI cleavage and co-transfected with the large fragment of ClaI-cut Ad-d1324 DNA into 293 (ATCC CRL1573) cells to allow homologous recombination to occur, followed by replication and encapsidation of recombinant adenoviral DNA into infectious virions and the formation of plaques. Individual plaques are isolated and amplified in 293 cells, viral DNA is isolated and recombinant adenovirus plaques containing the human RB cDNA (Ad-RB94) are identified by restriction cleavage and Southern analysis. Ad-RB94 viruses are propagated in 293 cells and recovered 36 hours after infection. The viral preparation is purified by CsCl density centrifugation, and stored in virus dialysis buffer (10 mH Tris-Hcl, pH7.4; 1 mH MgCl$_2$) at 4° C. for immediate use; or stored at −70° C. prior to use (with the addition of 10% glycerol). The basic protocol for construction of the recombinant adenovirus Ad-RB94 is modified from Rosenfeld, M. A., et al., *Cell*, 1992, 68:143–155.

4.3.9. Physical DNA Transfer Method

An alternative gene transfer method that has been approved for use in humans by the Food and Drug Administration is the transfer of plasmid DNA in liposomes directly to tumor cells in situ (Nabel, E. G., et al., 1990, *Science*, 249:1285–1288). Plasmid DNA is easy to certify for use in humans because, unlike retroviral vector, it can be purified to homogeneity.

The p94$^{RB}$ expressing plasmid vectors pCMV-s-RB42 or pβA-s-RB34 are used to form complexes with liposomes, and directly treat tumor cells in vivo (or ex vivo). In this procedure, as described in Section 4.4.1 infra, stable integration of the DNA into transfected tumor cells is not required for gene therapy as transient expression may suffice.

4.4. Treatment of Human Tumor Cells In Vitro With p94$^{RB}$ Plasmid Vectors pβA-s-RB34 or pCMV-s-RB42.

4.4.1. Treatment of RB-Defective Human Tumor Cells In Vitro

Human tumor cells having known RB gene deficiencies were treated with the p94$^{RB}$ plasmid vector pβA-s-RB34 (or pCMV-s-RB42). These include: 1) human bladder carcinoma cell line, 5637, (ATCC HTB9); 2) human breast carcinoma cell line, MDA-MB-468 (ATCC HTB132); 3) human non-small cell lung carcinoma cell line, H2009 (Kratzke, R. A., et al., 1992, *The Journal of Biological Chemistry*, 267:25998–26003); 4) human prostate carcinoma cell line, DU145 (ATCC HTB81); 5) human osteosarcoma cell line, Saos2 (ATCC HTB85); and 6) human fibrosarcoma metastatic to lung cell line, Hs913T (ATCC HTB152).

For treatment, tumor cells were transiently transfected with the plasmid DNA pβA-s-RB34 (or pCHVs-RB42) via LIPOFECTIN reagent (GIBCO BRL Life Technologies, Inc. Gaithersberg, Md.). Similar results have been obtained from transfection using calcium phosphate or electroporation methods.

The following procedures for transfection using LIPOFECTIN were modified from the manufacturer's specifications. Tumor cells were seeded in 100-mm dishes in appropriate growth medium supplemented with serum. The cells were incubated at 37° C. in a 5% CO$_2$ environment until the cells were 40–60% confluent. This usually took 18–24 hours, but the time varied among cell types. The following solution was prepared in 17×75 mm polystyrene tubes: Solution A - for each dish of cells to be transfected, 5–10 μg of plasmid DNA were diluted into a final volume of 100 μl with serum-free medium; Solution B - for each dish of cells to be transfected, 30–50 μl of LIPOFECTIN reagent was diluted into a final volume of 100 μl with serum-free medium. The two solutions were combined, mixed gently, and incubated at room temperature for 10–15 min. The LIPOFECTIN reagent interacted spontaneously with plasmid DNA to form a lipid-DNA complex. While the lipid-DNA complex was forming, the cells were washed twice with 6 ml of serum-free medium. For each transfection, 6 ml of serum-free medium were added to each polystyrene tube containing the lipid-DNA complex. The solution was mixed gently, and the medium-complex was overlayed onto the cells. The dishes were then swirled gently to ensure uniform distribution. The dishes were then incubated at 37° C. in a 5% CO$_2$ incubator. After 12 to 24 hours the medium-complex was replaced with appropriate growth medium containing 10% fetal calf serum.

In parallel studies, tumor cells were transfected with the plasmid DNA pβA-f-RB33 or pCMV-f-RB35 which expresses the p110$^{RB}$. The following assays were used to evaluate the growth inhibitory effects of introducing p94$^{RB}$ versus p110$^{RB}$ expression in RB defective tumor cells:

1) DNA synthesis in tumor cells treated with plasmid vectors.

After plasmid DNA treatment the tumor cells were labeled with [$^3$H]-thymidine for 2 hours, then transferred to polylysine-coated slides, fixed and immunocytochemically stained with a monoclonal anti-RB antibody, MAb-1 (Triton Biosciences, Inc. Alameda, Calif.). The RB-positive transfected cells were counted under the microscope. The slides were then coated with Kodak NTB2 autoradiographic emulsion and exposed for 7–10 days. The [$^3$H]-thymidine labeling and RB protein immunocytochemical staining were done according to the methods previously described (Xu et al., *Oncogene*, 1991, 6:1139–1146). About 400 to 1600 RB-positive and 600 RB-negative tumor cells were assessed for each determination of [$^3$H]-thymidine uptake. The study demonstrated that the RB-defective tumor cells expressing p94$^{RB}$ did not progress through the cell cycle, as evidenced by their failure to incorporate [$^3$H]-thymidine into DNA (Table 2). However, the percentage of cells undergoing DNA replication was only slightly lower in cells producing p110$^{RB}$ than in cells that were RB-negative (Table 2).

TABLE 2

Immunocytochemical Staining and [³H] Thymidine Incorporation of RB-Defective Tumor Cells Following Transfection With p94$^{RB}$ or p110$^{RB}$ Expression Plasmids

| Recipient Cells | Promoter | Protein Expressed | Cells Incorporating [3H] Thymidine | |
|---|---|---|---|---|
| | | | RB+ | RB− |
| 5637 | β-actin gene promoter | p110$^{RB}$ | 34% | 45% |
| | | p94$^{RB}$ | 2.3% | 43% |
| | Cytomegalovirus promoter/enhancer | p110$^{RB}$ | 21% | — |
| | | p94$^{RB}$ | 1.8% | — |
| MDA-MB-468 | Cytomegalovirus promoter/enhancer | p110$^{RB}$ | 14% | 40% |
| | | p94$^{RB}$ | 0.5% | 39% |
| H2009 | β-actin gene promoter | p110$^{RB}$ | 19% | 26% |
| | | p94$^{RB}$ | 0.1% | 27% |
| DU145 | Cytomegalovirus promoter/enhancer | p110$^{RB}$ | 23% | 33% |
| | | p94$^{RB}$ | 1.0% | 33% |
| Hs913T | Cytomegalovirus promoter/enhancer | p110$^{RB}$ | 18% | 34% |
| | | p94$^{RB}$ | 0.9% | 36% |
| Saos2 | Cytomegalovirus promoter/enhancer | p110$^{RB}$ | 19% | 32% |
| | | p94$^{RB}$ | 0.9% | 35% |

2) Colony formation assay.

Approximately 48 hours after transfection the tumor cells were replated at a density of 10⁵ cells per 100 mm dish with selected medium containing G418 of 400–600 μg/ml. Cells were cultured for 2 to 3 weeks and colonies of >100 cells were scored. The data are illustrated in Table 3. Cells treated with plasmid vectors expressing p94$^{RB}$ formed approximately four-fold fewer colonies than those transfected with p110$^{RB}$ plasmid vectors. The difference was statistically significant (p <0.05 by t-test).

Furthermore in those colonies that did form after p94$^{RB}$ plasmid DNA treatment, p94$^{RB}$ protein expression was no longer observed. Failure to isolate long-term cultures expressing the p94$^{RB}$ protein in treated tumor cells shows that p94$^{RB}$ did suppress tumor cell growth. In contrast, 7 of 48 cell lines (approximately 15%) derived from tumor cells after transfection with the p110$^{RB}$ plasmid DNA were found to express the p110$^{RB}$ protein. This percentage was consistent with results expected in human cells transfected with a vector containing two independent transcription units and therefore introduction of p110$^{RB}$ expression does not exert growth inhibitory effects on RB-defective tumor cells.

TABLE 3

Growth inhibitory effects of introducing p110$^{RB}$ and p94$^{RB}$ expression into RB-defective bladder carcinoma cell line, 5637 (HTB9). Each number represents 6 to 11 dishes.

| | Number of G418-Resistant Colonies Formed | | |
|---|---|---|---|
| Vector Type | Vector | p110$^{RB}$ | p94$^{RB}$ |
| pCMV-Neo-Bam | 280 | 24 | 6 |
| pHβAPr-1-neo | — | 33 | 8 |

3) The Effect of p94$^{RB}$ Expression on Cellular Morphology

The HTB9 transfectants were also immunostained with MAb-1 anti-RB monoclonal antibody about 24 hours after transfection. The staining results are illustrated in FIG. 8A–8C.

As demonstrated in FIG. 8, the majority of RB-positive, p94$^{RB}$-expressing HTB9 cells become very large in size, with lower nucleocytoplasmic ratio, or higher incidence of being multinucleated cells (panel C), a morphological change frequently associated with cellular senescence. However, such a morphological change has not been seen in group A, mock-transfected HTB9 cells and group B, p110$^{RB}$ expressing RB-positive HTB9 cells (FIG. 8, panels A and B).

4.4.2. Treatment of Human Tumor Cells Having Normal (p110$^{RB}$) RB Expression (RB+)

Two RB+ human cell lines (i.e., having no RB gene defect), including a human fibrosarcoma cell line, HT1080 (ATCC CCL121), and human cervix carcinoma cell line, HeLa (ATCC CCL2) were treated with the p94$^{RB}$ protein expression plasmid, pCMV-s-RB42, using the LIPOFECTIN reagent as described supra. In parallel studies, these cell lines were also transfected with the p110$^{RB}$ protein expression plasmid, pCMV-f-RB35. The colony formation assay as described supra was used to evaluate the growth inhibitory effects of introducing exogenous p94$^{RB}$ versus p110$^{RB}$ expression in RB+ tumor cells. As shown in Table 4, expression of the p94$^{RB}$ protein dramatically inhibited the cell growth of HT1080 and HeLa cells. There was a two- to nine-fold reduction in the number of G418-resistant colonies formed after treated with the plasmid victor pCMV-s-RB42 expressing p94$^{RB}$, while no such effect was observed by transfection with the pCMV-f-RB35 plasmid (expressing p110$^{RB}$ protein). The difference was statistically significant (the two-tailed P values were less than 0.03 as calculated by the paired t-test).

TABLE 4

Growth inhibitory effects of introducing p110$^{RB}$ and p94$^{RB}$ expression into RB-positive human fibrosarcoma cell line, HT1080 and the RB positive human cervix carcinoma cell line, HeLa. The RB expression was under the control of cytomegalovirus (CMV) promoter. For each experiment, three 5-cm² dishes were transfected and the total colonies counted after ten days of selection in G418 (1 mg/ml).

| | No. or G418-Resistant Colonies Formed | | | |
|---|---|---|---|---|
| Recipient Cells | Experiment | Vector | p110$^{RB}$ | p94$^{RB}$ |
| HT1080 | 1 | 94 | 129 | 14 |
| | 2 | 88 | 122 | 16 |
| | 3 | 100 | 120 | 17 |
| | 4 | 99 | 110 | 15 |
| HeLa | 1 | 24 | 20 | 10 |
| | 2 | 25 | 24 | 9 |

4.5 Half-Life and Phosphorylation state of the p94$^{RB}$ Protein In Host Cells: The Distinct Properties of p94$^{RB}$ The half-life of transiently expressed p94$^{RB}$ and p110$^{RB}$ proteins in transfected bladder carcinoma cell line, 5637 (ATCC HTB9) was measured by pulse-labeling of transfected 5637 cells with [³⁵S]-methionine followed by a chase with excess unlabeled methionine (FIG. 9).

The bladder tumor cells were transfected in multiple dishes with either p110$^{RB}$ (FIG. 9, left) or p94$^{RB}$ (FIG. 9, right) expression plasmids. Twenty-four hours after transfection the cells were labeled with [³⁵S]-methionine and chased with excess unlabeled methionine for 0, 6, 12 and 24 hours, respectively. RB proteins were determined by immunoprecipitation.

The half-life of p94$^{RB}$ protein in the transfected 5637 cells was determined to be 12 hours. In contrast, the half-life of p110$^{RB}$ protein was 4–6 hours. Therefore, p94$^{RB}$ protein expressed in host tumor cells has a slower turnover, which is believed to contribute to its efficacy as a suppressor of both RB+ and RB− tumor cell replication.

The comparative phosphorylation states of p110$^{RB}$ and p94$^{RB}$ in transiently transfected 5637 cells were determined by Western blot analysis: cell-lysates were made from WI-38, parental 5637 and pβA-f-RB33 (expressing p110$^{RB}$, Section 4.3.5) or pβA-s-RB34 (expressing p94$^{RB}$, Section 4.3.4) plasmid transfected 5637 cells approximately 24 hours after transfection. The basic protocol for Western blot analysis was described in Xu, H-J., et al., 1989, *Oncogene*, 4:807–812. Each lane was loaded with 40 μl of the lysate corresponding to 4×10$^5$ cultured cells. Proteins were separated by 8% SDS-PAGE and electroblotted to a PVDF membrane. After blocking with 3% non-fat milk in TBST (10 mM Tris-HCl, pH8.0, 150 mM NaCl, 0.05% Tween 20), the membrane was incubated with MAb-1 monoclonal anti-RB antibody at 0.1 μg/cm$^2$ overnight. The blot was then probed by the Enhanced Chemiluminescence (ECL) (Amersham Corporation, Arlington Heights, Ill.) immunodetection method. X-ray films were exposed for 2 seconds (FIG. 10, lane 1) or 30 seconds (FIG. 10, lanes 2–4).

Of particular interest was the fact that the RB-defective bladder carcinoma cell line, 5637, failed to phosphorylate the p94$^{RB}$ protein as shown by Western blot analysis (FIG. 10, lane 4), although the p110$^{RB}$ proteins expressed in transfected 5637 cells were fully phosphorylated (FIG. 10, lane 3). Therefore, the presence of only unphosphorylated p94$^{RB}$ proteins may also account for the failure of transfected 5637 tumor cells to enter S phase, and this in turn may cause cellular senescence and cell death.

4.6. Treatment of Human Bladder Cancers In Vivo.

The human bladder cancer represents an ideal model for practicing tumor suppressor gene therapy of solid tumors by infusing the p94$^{RB}$ protein expression retroviral vectors into the bladder. The original experimental model of human bladder cancer was established by Dr. Peter A. Jones and his colleagues (Ahlering, T. E., et al., *Cancer Res.*, 1987, 47.,6660–6665). It has been shown that human bladder tumor cells of RT4 cell line established from a superficial papillary tumor (which usually does not metastasize) produced tumors only locally when injected by a 22-gauge catheter into the bladder of female nude mice. In contrast, the EJ bladder carcinoma cells which were originally isolated from a more aggressive human bladder cancer produced invasive tumors in the nude mouse bladders which metastasized to the lung spontaneously (Ahlering, T. E., et al., *Cancer Res.*, 1987, 47:6660–6665). Therefore, this model can be used for treatment of experimental bladder cancer by in vivo gene transfer with retroviral vectors.

Tumor cells from RB minus human bladder carcinoma cell line, 5637 (ATCC HTB9) and RB+ human bladder carcinoma cell line, SCaBER (ATCC HTB3) are injected directly into the bladders of female athymic (nu/nu) nude mice (6 to 8 weeks of age) by a catheter as initially reported by Jones and his colleagues (Ahlering, T. E., et al., *Cancer Res.*, 1987, 47:6660–6665).

Development and progression of the nude mouse bladder tumors are monitored using a fiber-optical system to which a TV monitor is attached. The experimental tumors are subsequently treated with retrovirus vectors expressing the p94$^{RB}$.

Supernatants with high virus titers are obtained from tissue culture media of selected PA317 clones expressing high level of human p94$^{RB}$ protein (Section 4.3.7) and confirmed as free of replication-competent virus prior to use. The retroviral vector suspension at high titers ranging from 4×10$^4$ to greater than 1×10$^7$ colony-forming unit (cfu)/ml, and more preferably at a titer greater than 1×10$^6$ cfu/ml is then infused directly into the mouse bladders via a catheter to treat the tumors. The skilled artisan will understand that such treatments can be repeated as many times as necessary via a catheter inserted into the bladder. The tumor regression following transferring the p94$^{RB}$ gene is monitored frequently via the fiber-optic system mentioned above.

The same procedure as described above is used for treating the human bladder cancer except that the retroviral vector suspension is infused into a human bladder bearing cancer.

4.7. In Vivo Studies Using an Orthotopic Lung Cancer Model

Human large cell lung carcinoma, NCI-H460 (ATCC HTB177) cells which have normal p110$^{RB}$ expression are injected into the right mainstream bronchus of athymic (nu/nu) nude mice (10$^5$ cells per mouse). Three days later the mice are inoculated endobronchically with supernatant from the p94$^{RB}$, or p110$^{RB}$ retrovirus producer cells daily for three consecutive days. Tumor formation is suppressed in the group of mice treated with the p94$^{RB}$ retrovirus supernatant. In contrast, in the other group, which is treated with p110$^{RB}$ retrovirus supernatant, the majority of mice develop endobronchial tumors. This indicates that the p94$^{RB}$-expressing retrovirus inhibits growth of RB+ non-small cell lung carcinoma (NSCLC) cells, whereas the p110$^{RB}$-expressing retrovirus does not.

4.8. Treatment of Human Non-Small Cell Lung Cancers In Vivo.

Non-small cell lung cancer patients having an endobronchial tumor accessible to a bronchoscope, and also having a bronchial obstruction, are initially selected for p94$^{RB}$ gene therapy. Treatment is administered by bronchoscopy under topical or general anesthesia. To begin the procedure, as much gross tumor as possible is resected endoscopically. A transbronchial aspiration needle (21G) is passed through the biopsy channel of the bronchoscope.

The residual tumor site is injected with the appropriate retroviral vector supernatant (Section 4.3.7), adenovirus Ad-RB94 suspension (Section 4.3.8) or p94$^{RB}$-expressing plasmid vector-liposome complexes (Section 4.3.4 and 4.3.6) at a volume of 5 ml to 10 ml. Protamine is added at a concentration of 5 μg/ml. The injections of therapeutic viral or plasmid supernatant comprising one or more of the vectors are administered around and within the tumor or tumors and into the submucosa adjacent to the tumor. The injections are repeated daily for five consecutive days and monthly thereafter. The treatment may be continued as long as there is no tumor progression. After one year the patients are evaluated to determine whether it is appropriate to continue therapy.

In addition, as a precaution the patients wear a surgical mask for 24 hours following injection of the viral supernatant. All medical personnel wear masks routinely during bronchoscopy and injection of the viral supernatant. Antitussive is prescribed as necessary.

4.9 Treatment or Prevention of Human Lung Carcinomas With Liposome-Encapsulated Purified p94$^{RB}$ Protein In yet another alternative, target tumor or cancer cells are treated by introducing p94$^{RB}$ protein into cells in need of such treatment by any known method. For example, liposomes are artificial membrane vesicles that have been extensively studied for their usefulness as delivery vehicles of drugs, proteins and plasmid vectors both in vitro or in vivo (Mannino, R. J. et al., 1988, *Biotechniques*, 6:682–690). Proteins such as erythrocyte anion transporter (Newton, A. C. and Huestis, W. H., *Biochemistry*, 1988, 27:4655–4659), superoxide dismutase and catalase (Tanswell, A. K. et al., 1990, *Biochmica et Biophysica Acta*, 1044:269–274), and UV-DNA repair enzyme (Ceccoll, J. et al. *Journal of Investigative Dermatology*, 1989, 93:190–194) have been encapsulated at high efficiency with liposome vesicles and delivered into mammalian cells in vitro or in vivo.

Further, small-particle aerosols provide a method for the delivery of drugs for treatment of respiratory diseases. For example, it has been reported that drugs can be administered in small-particle aerosols by using liposomes as a vehicle. Administered via aerosols, the drugs are deposited rather uniformly on the surface of the nasopharynx, the tracheo-bronchial tree and in the pulmonary area (Knight, V. and Gilbert, B., 1988, *European Journal of Clinical Microbiology and Infectious Diseases*, 7:721–731).

To treat or prevent lung cancers, the therapeutic $p94^{RB}$ protein is purified, for example, from recombinant baculovirus AcHNPV-RB94 infected insect cells by immunoaffinity chromatography (Sections 4.1 and 4.2) or any other convenient source. The $p94^{RB}$ protein is mixed with liposomes and incorporated into the liposome vesicles at high efficiency. The encapsulated $p94^{RB}$ is active. Since the aerosol delivery method is mild and well-tolerated by normal volunteers and patients, the $p94^{RB}$-containing liposomes can be administered to treat patients suffering from lung cancers of any stage and/or to prevent lung cancers in high-risk population. The $p94^{RB}$ protein-containing liposomes are administered by nasal inhalation or by a endotracheal tube via small-particle aerosols at a dose sufficient to suppress abnormal cell proliferation. Aerosolization treatments are administered to a patient for 30 minutes, three times daily for two weeks, with repetition as needed. The $p94^{RB}$ protein is thereby delivered throughout the respiratory tract and the pulmonary area. The treatment may be continued as long as necessary. After one year the patent's overall condition will be evaluated to determine if continued therapy is appropriate.

5. Deposit of Microorganisms

The following were deposited on Feb. 10, 1993 with the American Type Culture Collection, 12301 Parklawn Drive, Rockville, Md. 20852:

| *Escherichia coli* DH5α | ATCC Designation |
|---|---|
| DHC-S-RB42 | 69240 |
| DHB-S-RB34 | 69241 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

We claim:

1. A method of suppressing proliferation of a tumor cell, comprising introducing into the tumor cell an expression vector which comprises a polynucleotide that encodes a polypeptide having the amino acid sequence as shown in SEQ ID NO:3, provided that said polynucleotide does not also encode $p110^{RB}$; wherein following said introduction, said polypeptide is expressed in said tumor cell, thereby suppressing proliferation of said tumor cell.

2. The method of claim 1 in which the polynucleotide comprises the nucleotide sequence as shown in SEQ ID NO:1 from nucleotide #19 to and including #2466.

3. The method of claim 1 in which the cell is a human tumor cell.

4. The method of claim 3 in which the tumor cell expresses a wild type retinoblastoma $p110^{RB}$ protein.

5. The method of claim 3 in which the tumor cell does not express a wild type retinoblastoma $p110^{RB}$ protein.

6. The method of claim 3 in which the tumor cell is a retinoblastoma cell, a breast carcinoma cell, a lung carcinoma cell, a prostate carcinoma cell, a bladder carcinoma cell, a cervical carcinoma cell, a fibrosarcoma cell, or an osteosarcoma cell.

7. The method of claim 1 in which the expression vector is a viral vector.

8. The method of claim 7 in which the viral vector is a retroviral vector, an adenoviral vector or a herpes viral vector.

9. The method of claim 8 in which the adenoviral vector is prepared from an adenovirus type 5 deletion mutant.

10. The method of claim 1 in which the expression vector is a plasmid.

11. The method of claim 1 in which the polynucleotide is operably linked to a retinoblastoma gene promoter, a retroviral long-terminal repeat, a cytomegalovirus promoter, a β-actin promoter, a glucocorticoid-inducible promoter, a SV40 early region promoter or a herpes simplex virus thymidine kinase promoter.

12. The method of claim 1 in which the expression vector is introduced into the cell by viral infection, liposome-mediated transfection, polybrene-mediated transfection or $CaPO_4$-mediated transfection.

13. The method of claim 1 in which the expression vector is introduced into the cell in vitro.

14. The method of claim 1 in which the expression vector is introduced into the cell in vivo.

15. A method of suppressing tumor cell proliferation in a human subject, comprising introducing into said tumor cell in said subject an expression vector which comprises a polynucleotide that encodes a polypeptide having the amino acid sequence as shown in SEQ ID NO:3, provided that said polynucleotide does not also encode $p110^{RB}$; wherein following said introduction, said polypeptide is expressed in said tumor cell in said subject, thereby suppressing proliferation of said tumor cell in said subject.

16. The method of claim 15 in which the polynucleotide comprises the nucleotide sequence as shown in SEQ ID NO:1 from nucleotide #19 to and including #2466.

17. The method of claim 15 in which the tumor cell expresses a wild type retinoblastoma $p110^{RB}$ protein.

18. The method of claim 15 in which the tumor cell does not express a wild type retinoblastoma $p110^{RB}$ protein.

19. The method of claim 15 in which the tumor cell is a retinoblastoma cell, a breast carcinoma cell, a lung carcinoma cell, a prostate carcinoma cell, a bladder carcinoma cell, a cervical carcinoma cell, a fibrosarcoma cell, or an osteosarcoma cell.

20. The method of claim 15 in which the expression vector is a viral vector.

21. The method of claim 20 in which the viral vector is a retroviral vector, an adenoviral vector or a herpes viral vector.

22. The method of claim 21 in which the adenoviral vector is prepared from an adenovirus type 5 deletion mutant.

23. The method of claim 15 in which the expression vector is a plasmid.

24. The method of claim 15 in which the polynucleotide is operably lined to a retinoblastoma gene promoter, a retroviral long-terminal repeat, a cytomegalovirus promoter, a β-actin promoter, a glucocorticoid-inducible promoter, a SV40 early region promoter or a herpes simplex virus thymidine kinase promoter.

25. The method of claim 15 in which the expression vector in introduced into said tumor cell by viral infection or by liposome-mediated transfection.

26. The method of claim 15 in which the expression vector is introduced into said tumor cell following delivery of said vector to the site where said tumor cell is present in said subject.

27. The method of claim 26 in which the expression vector is delivered by direct injection.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 3232 base pairs
      (B) TYPE: nucleic acid
      (C) STRANDEDNESS: double
      (D) TOPOLOGY: Not Relevant (ii) MOLECULE TYPE: DNA (ix) FEATURE:
      (A) NAME/KEY: CDS
      (B) LOCATION: 19..2469

(xi) SEQUENCE DESCRIPTION: SEQ ID NO:1:

```
GATCCCGACC TAGATGAG ATG TCG TTC ACT TTT ACT GAG CTA CAG AAA AAC         51
                    Met Ser Phe Thr Phe Thr Glu Leu Gln Lys Asn
                     1               5                      10

ATA GAA ATC AGT GTC CAT AAA TTC TTT AAC TTA CTA AAA GAA ATT GAT         99
Ile Glu Ile Ser Val His Lys Phe Phe Asn Leu Leu Lys Glu Ile Asp
            15                  20                  25

ACC AGT ACC AAA GTT GAT AAT GCT ATG TCA AGA CTG TTG AAG AAG TAT        147
Thr Ser Thr Lys Val Asp Asn Ala Met Ser Arg Leu Leu Lys Lys Tyr
        30                  35                  40

GAT GTA TTG TTT GCA CTC TTC AGC AAA TTG GAA AGG ACA TGT GAA CTT        195
Asp Val Leu Phe Ala Leu Phe Ser Lys Leu Glu Arg Thr Cys Glu Leu
    45                  50                  55

ATA TAT TTG ACA CAA CCC AGC AGT TCG ATA TCT ACT GAA ATA AAT TCT        243
Ile Tyr Leu Thr Gln Pro Ser Ser Ser Ile Ser Thr Glu Ile Asn Ser
60                  65                  70                  75

GCA TTG GTG CTA AAA GTT TCT TGG ATC ACA TTT TTA TTA GCT AAA GGG        291
Ala Leu Val Leu Lys Val Ser Trp Ile Thr Phe Leu Leu Ala Lys Gly
                80                  85                  90
```

| | | |
|---|---|---|
| GAA GTA TTA CAA ATG GAA GAT GAT CTG GTG ATT TCA TTT CAG TTA ATG | 339 | |
| Glu Val Leu Gln Met Glu Asp Asp Leu Val Ile Ser Phe Gln Leu Met | | |
| 95 100 105 | | |
| CTA TGT GTC CTT GAC TAT TTT ATT AAA CTC TCA CCT CCC ATG TTG CTC | 387 | |
| Leu Cys Val Leu Asp Tyr Phe Ile Lys Leu Ser Pro Pro Met Leu Leu | | |
| 110 115 120 | | |
| AAA GAA CCA TAT AAA ACA GCT GTT ATA CCC ATT AAT GGT TCA CCT CGA | 435 | |
| Lys Glu Pro Tyr Lys Thr Ala Val Ile Pro Ile Asn Gly Ser Pro Arg | | |
| 125 130 135 | | |
| ACA CCC AGG CGA GGT CAG AAC AGG AGT GCA CGG ATA GCA AAA CAA CTA | 483 | |
| Thr Pro Arg Arg Gly Gln Asn Arg Ser Ala Arg Ile Ala Lys Gln Leu | | |
| 140 145 150 155 | | |
| GAA AAT GAT ACA AGA ATT ATT GAA GTT CTC TGT AAA GAA CAT GAA TGT | 531 | |
| Glu Asn Asp Thr Arg Ile Ile Glu Val Leu Cys Lys Glu His Glu Cys | | |
| 160 165 170 | | |
| AAT ATA GAT GAG GTG AAA AAT GTT TAT TTC AAA AAT TTT ATA CCT TTT | 579 | |
| Asn Ile Asp Glu Val Lys Asn Val Tyr Phe Lys Asn Phe Ile Pro Phe | | |
| 175 180 185 | | |
| ATG AAT TCT CTT GGA CTT GTA ACA TCT AAT GGA CTT CCA GAG GTT GAA | 627 | |
| Met Asn Ser Leu Gly Leu Val Thr Ser Asn Gly Leu Pro Glu Val Glu | | |
| 190 195 200 | | |
| AAT CTT TCT AAA CGA TAC GAA GAA ATT TAT CTT AAA AAT AAA GAT CTA | 675 | |
| Asn Leu Ser Lys Arg Tyr Glu Glu Ile Tyr Leu Lys Asn Lys Asp Leu | | |
| 205 210 215 | | |
| GAT GCA AGA TTA TTT TTG GAT CAT GAT AAA ACT CTT CAG ACT GAT TCT | 723 | |
| Asp Ala Arg Leu Phe Leu Asp His Asp Lys Thr Leu Gln Thr Asp Ser | | |
| 220 225 230 235 | | |
| ATA GAC AGT TTT GAA ACA CAG AGA ACA CCA CGA AAA AGT AAC CTT GAT | 771 | |
| Ile Asp Ser Phe Glu Thr Gln Arg Thr Pro Arg Lys Ser Asn Leu Asp | | |
| 240 245 250 | | |
| GAA GAG GTG AAT GTA ATT CCT CCA CAC ACT CCA GTT AGG ACT GTT ATG | 819 | |
| Glu Glu Val Asn Val Ile Pro Pro His Thr Pro Val Arg Thr Val Met | | |
| 255 260 265 | | |
| AAC ACT ATC CAA CAA TTA ATG ATG ATT TTA AAT TCA GCA AGT GAT CAA | 867 | |
| Asn Thr Ile Gln Gln Leu Met Met Ile Leu Asn Ser Ala Ser Asp Gln | | |
| 270 275 280 | | |
| CCT TCA GAA AAT CTG ATT TCC TAT TTT AAC AAC TGC ACA GTG AAT CCA | 915 | |
| Pro Ser Glu Asn Leu Ile Ser Tyr Phe Asn Asn Cys Thr Val Asn Pro | | |
| 285 290 295 | | |
| AAA GAA AGT ATA CTG AAA AGA GTG AAG GAT ATA GGA TAC ATC TTT AAA | 963 | |
| Lys Glu Ser Ile Leu Lys Arg Val Lys Asp Ile Gly Tyr Ile Phe Lys | | |
| 300 305 310 315 | | |
| GAG AAA TTT GCT AAA GCT GTG GGA CAG GGT TGT GTC GAA ATT GGA TCA | 1011 | |
| Glu Lys Phe Ala Lys Ala Val Gly Gln Gly Cys Val Glu Ile Gly Ser | | |
| 320 325 330 | | |
| CAG CGA TAC AAA CTT GGA GTT CGC TTG TAT TAC CGA GTA ATG GAA TCC | 1059 | |
| Gln Arg Tyr Lys Leu Gly Val Arg Leu Tyr Tyr Arg Val Met Glu Ser | | |
| 335 340 345 | | |
| ATG CTT AAA TCA GAA GAA GAA CGA TTA TCC ATT CAA AAT TTT AGC AAA | 1107 | |
| Met Leu Lys Ser Glu Glu Glu Arg Leu Ser Ile Gln Asn Phe Ser Lys | | |
| 350 355 360 | | |
| CTT CTG AAT GAC AAC ATT TTT CAT ATG TCT TTA TTG GCG TGC GCT CTT | 1155 | |
| Leu Leu Asn Asp Asn Ile Phe His Met Ser Leu Leu Ala Cys Ala Leu | | |
| 365 370 375 | | |
| GAG GTT GTA ATG GCC ACA TAT AGC AGA AGT ACA TCT CAG AAT CTT GAT | 1203 | |
| Glu Val Val Met Ala Thr Tyr Ser Arg Ser Thr Ser Gln Asn Leu Asp | | |
| 380 385 390 395 | | |
| TCT GGA ACA GAT TTG TCT TTC CCA TGG ATT CTG AAT GTG CTT AAT TTA | 1251 | |
| Ser Gly Thr Asp Leu Ser Phe Pro Trp Ile Leu Asn Val Leu Asn Leu | | |
| 400 405 410 | | |

```
AAA GCC TTT GAT TTT TAC AAA GTG ATC GAA AGT TTT ATC AAA GCA GAA    1299
Lys Ala Phe Asp Phe Tyr Lys Val Ile Glu Ser Phe Ile Lys Ala Glu
            415                 420                 425

GGC AAC TTG ACA AGA GAA ATG ATA AAA CAT TTA GAA CGA TGT GAA CAT    1347
Gly Asn Leu Thr Arg Glu Met Ile Lys His Leu Glu Arg Cys Glu His
        430                 435                 440

CGA ATC ATG GAA TCC CTT GCA TGG CTC TCA GAT TCA CCT TTA TTT GAT    1395
Arg Ile Met Glu Ser Leu Ala Trp Leu Ser Asp Ser Pro Leu Phe Asp
    445                 450                 455

CTT ATT AAA CAA TCA AAG GAC CGA GAA GGA CCA ACT GAT CAC CTT GAA    1443
Leu Ile Lys Gln Ser Lys Asp Arg Glu Gly Pro Thr Asp His Leu Glu
460                 465                 470                 475

TCT GCT TGT CCT CTT AAT CTT CCT CTC CAG AAT AAT CAC ACT GCA GCA    1491
Ser Ala Cys Pro Leu Asn Leu Pro Leu Gln Asn Asn His Thr Ala Ala
                480                 485                 490

GAT ATG TAT CTT TCT CCT GTA AGA TCT CCA AAG AAA AAA GGT TCA ACT    1539
Asp Met Tyr Leu Ser Pro Val Arg Ser Pro Lys Lys Lys Gly Ser Thr
            495                 500                 505

ACG CGT GTA AAT TCT ACT GCA AAT GCA GAG ACA CAA GCA ACC TCA GCC    1587
Thr Arg Val Asn Ser Thr Ala Asn Ala Glu Thr Gln Ala Thr Ser Ala
        510                 515                 520

TTC CAG ACC CAG AAG CCA TTG AAA TCT ACC TCT CTT TCA CTG TTT TAT    1635
Phe Gln Thr Gln Lys Pro Leu Lys Ser Thr Ser Leu Ser Leu Phe Tyr
    525                 530                 535

AAA AAA GTG TAT CGG CTA GCC TAT CTC CGG CTA AAT ACA TTT TGT GAA    1683
Lys Lys Val Tyr Arg Leu Ala Tyr Leu Arg Leu Asn Thr Leu Cys Glu
540                 545                 550                 555

CGC CTT CTG TCT GAG CAC CCA GAA TTA GAA CAT ATC ATC TGG ACC CTT    1731
Arg Leu Leu Ser Glu His Pro Glu Leu Glu His Ile Ile Trp Thr Leu
                560                 565                 570

TTC CAG CAC ACC CTG CAG AAT GAG TAT GAA CTC ATG AGA GAC AGG CAT    1779
Phe Gln His Thr Leu Gln Asn Glu Tyr Glu Leu Met Arg Asp Arg His
            575                 580                 585

TTG GAC CAA ATT ATG ATG TGT TCC ATG TAT GGC ATA TGC AAA GTG AAG    1827
Leu Asp Gln Ile Met Met Cys Ser Met Tyr Gly Ile Cys Lys Val Lys
        590                 595                 600

AAT ATA GAC CTT AAA TTC AAA ATC ATT GTA ACA GCA TAC AAG GAT CTT    1875
Asn Ile Asp Leu Lys Phe Lys Ile Ile Val Thr Ala Tyr Lys Asp Leu
    605                 610                 615

CCT CAT GCT GTT CAG GAG ACA TTC AAA CGT GTT TTG ATC AAA GAA GAG    1923
Pro His Ala Val Gln Glu Thr Phe Lys Arg Val Leu Ile Lys Glu Glu
620                 625                 630                 635

GAG TAT GAT TCT ATT ATA GTA TTC TAT AAC TCG GTC TTC ATG CAG AGA    1971
Glu Tyr Asp Ser Ile Ile Val Phe Tyr Asn Ser Val Phe Met Gln Arg
                640                 645                 650

CTG AAA ACA AAT ATT TTG CAG TAT GCT TCC ACC AGG CCC CCT ACC TTG    2019
Leu Lys Thr Asn Ile Leu Gln Tyr Ala Ser Thr Arg Pro Pro Thr Leu
            655                 660                 665

TCA CCA ATA CCT CAC ATT CCT CGA AGC CCT TAC AAG TTT CCT AGT TCA    2067
Ser Pro Ile Pro His Ile Pro Arg Ser Pro Tyr Lys Phe Pro Ser Ser
        670                 675                 680

CCC TTA CGG ATT CCT GGA GGG AAC ATC TAT ATT TCA CCC CTG AAG AGT    2115
Pro Leu Arg Ile Pro Gly Gly Asn Ile Tyr Ile Ser Pro Leu Lys Ser
    685                 690                 695

CCA TAT AAA ATT TCA GAA GGT CTG CCA ACA CCA ACA AAA ATG ACT CCA    2163
Pro Tyr Lys Ile Ser Glu Gly Leu Pro Thr Pro Thr Lys Met Thr Pro
700                 705                 710                 715

AGA TCA AGA ATC TTA GTA TCA ATT GGT GAA TCA TTC GGG ACT TCT GAG    2211
Arg Ser Arg Ile Leu Val Ser Ile Gly Glu Ser Phe Gly Thr Ser Glu
                720                 725                 730
```

```
AAG TTC CAG AAA ATA AAT CAG ATG GTA TGT AAC AGC GAC CGT GTG CTC      2259
Lys Phe Gln Lys Ile Asn Gln Met Val Cys Asn Ser Asp Arg Val Leu
            735                 740                 745

AAA AGA AGT GCT GAA GGA AGC AAC CCT CCT AAA CCA CTG AAA AAA CTA      2307
Lys Arg Ser Ala Glu Gly Ser Asn Pro Pro Lys Pro Leu Lys Lys Leu
                750                 755                 760

CGC TTT GAT ATT GAA GGA TCA GAT GAA GCA GAT GGA AGT AAA CAT CTC      2355
Arg Phe Asp Ile Glu Gly Ser Asp Glu Ala Asp Gly Ser Lys His Leu
            765                 770                 775

CCA GGA GAG TCC AAA TTT CAG CAG AAA CTG GCA GAA ATG ACT TCT ACT      2403
Pro Gly Glu Ser Lys Phe Gln Gln Lys Leu Ala Glu Met Thr Ser Thr
780                 785                 790                 795

CGA ACA CGA ATG CAA AAG CAG AAA ATG AAT GAT AGC ATG GAT ACC TCA      2451
Arg Thr Arg Met Gln Lys Gln Lys Met Asn Asp Ser Met Asp Thr Ser
                800                 805                 810

AAC AAG GAA GAG AAA TGAGGATCTC AGGACCTTGG TGGACACTGT GTACACCTCT      2506
Asn Lys Glu Glu Lys
                815

GGATTCATTG TCTCTCACAG ATGTGACTGT ATAACTTTCC CAGGTTCTGT TTATGGCCAC    2566

ATTTAATATC TTCAGCTCTT TTTGTGGATA TAAAATGTGC AGATGCAATT GTTTGGGTGA    2626

TTCCTAAGCC ACTTGAAATG TTAGTCATTG TTATTTATAC AAGATTGAAA ATCTTGTGTA    2686

AATCCTGCCA TTTAAAAAGT TGTAGCAGAT TGTTTCCTCT TCCAAAGTAA AATTGCTGTG    2746

CTTTATGGAT AGTAAGAATG GCCCTAGAGT GGGAGTCCTG ATAACCCAGG CCTGTCTGAC    2806

TACTTTGCCT TCTTTTGTAG CATATAGGTG ATGTTTGCTC TTGTTTTTAT TAATTTATAT    2866

GTATATTTTT TTAATTTAAC ATGAACACCC TTAGAAAATG TGTCCTATCT ATCATCCAAA    2926

TGCAATTTGA TTGACTGCCC ATTCACCAAA ATTATCCTGA ACTCTTCTGC AAAAATGGAT    2986

ATTATTAGAA ATTAGAAAAA AATTACTAAT TTTACACATT AGATTTTATT TTACTATTGG    3046

AATCTGTATAT ACTGTGTGCT TGTTTTATAA AATTTTGCTT TTAATTAAAT AAAAGCTGGA   3106

AGCAAAGTAT AACCATATGA TACTATCATA CTACTGAAAC AGATTTCATA CCTCAGAATG    3166

TAAAAGAACT TACTGATTAT TTTCTTCATC CAACTTATGT TTTTAAATGA GGATTATTGA    3226

TAGTGG                                                               3232

(2) INFORMATION FOR SEQ ID NO:2:

(i) SEQUENCE CHARACTERISTICS:
        (A) LENGTH: 3232 base pairs
        (B) TYPE: nucleic acid
        (C) STRANDEDNESS: double
        (D) TOPOLOGY: Not Relevant (ii) MOLECULE TYPE: DNA (xi) SEQUENCE DESCRIPTION: SEQ ID NO:2:

GATCCCACTA TCAATAATCC TCATTTAAAA ACATAAGTTG GATGAAGAAA ATAATCAGTA      60

AGTTCTTTTA CATTCTGAGG TATGAAATCT GTTTCAGTAG TATGATAGTA TCATATGGTT     120

ATACTTTGCT TCCAGCTTTT ATTTAATTAA AAGCAAAATT TTATAAAACA AGCACACAGT     180

ATATCAGATT CCAATAGTAA AATAAAATCT AATGTGTAAA ATTAGTAATT TTTTTCTAAT     240

TTCTAATAAT ATCCATTTTT GCAGAAGAGT TCAGGATAAT TTTGGTGAAT GGGCAGTCAA     300

TCAAATTGCA TTTGGATGAT AGATAGGACA CATTTTCTAA GGGTGTTCAT GTTAAATTAA     360

AAAAATATAC ATATAAATTA ATAAAAACAA GAGCAAACAT CACCTATATG CTACAAAAGA     420

AGGCAAAGTA GTCAGACAGG CCTGGGTTAT CAGGACTCCC ACTCTAGGGC CATTCTTACT     480

ATCCATAAAG CACAGCAATT TTACTTTGGA AGAGGAAACA ATCTGCTACA ACTTTTTAAA     540
```

```
TGGCAGGATT TACACAAGAT TTTCAATCTT GTATAAATAA CAATGACTAA CATTTCAAGT      600

GGCTTAGGAA TCACCCAAAC AATTGCATCT GCACATTTTA TATCCACAAA AAGAGCTGAA      660

GATATTAAAT GTGGCCATAA ACAGAACCTG GGAAAGTTAT ACAGTCACAT CTGTGAGAGA      720

CAATGAATCC AGAGGTGTAC ACAGTGTCCA CCAAGGTCCT GAGATCCTCA TTTCTCTTCC      780

TTGTTTGAGG TATCCATGCT ATCATTCATT TTCTGCTTTT GCATTCGTGT TCGAGTAGAA      840

GTCATTTCTG CCAGTTTCTG CTGAAATTTG GACTCTCCTG GGAGATGTTT ACTTCCATCT      900

GCTTCATCTG ATCCTTCAAT ATCAAAGCGT AGTTTTTTCA GTGGTTTAGG AGGGTTGCTT      960

CCTTCAGCAC TTCTTTTGAG CACACGGTCG CTGTTACATA CCATCTGATT TATTTTCTGG     1020

AACTTCTCAG AAGTCCCGAA TGATTCACCA ATTGATACTA AGATTCTTGA TCTTGGAGTC     1080

ATTTTTGTTG GTGTTGGCAG ACCTTCTGAA ATTTTATATG GACTCTTCAG GGGTGAAATA     1140

TAGATGTTCC CTCCAGGAAT CCGTAAGGGT GAACTAGGAA ACTTGTAAGG GCTTCGAGGA     1200

ATGTGAGGTA TTGGTGACAA GGTAGGGGGC CTGGTGGAAG CATACTGCAA AATATTTGTT     1260

TTCAGTCTCT GCATGAAGAC CGAGTTATAG AATACTATAA TAGAATCATA CTCCTCTTCT     1320

TTGATCAAAA CACGTTTGAA TGTCTCCTGA ACAGCATGAG GAAGATCCTT GTATGCTGTT     1380

ACAATGATTT TGAATTTAAG GTCTATATTC TTCACTTTGC ATATGCCATA CATGGAACAC     1440

ATCATAATTT GGTCCAAATG CCTGTCTCTC ATGAGTTCAT ACTCATTCTG CAGGGTGTGC     1500

TGGAAAAGGG TCCAGATGAT ATGTTCTAAT TCTGGGTGCT CAGACAGAAG GCGTTCACAA     1560

AGTGTATTTA GCCGGAGATA GGCTAGCCGA TACACTTTTT TATAAAACAG TGAAAGAGAG     1620

GTAGATTTCA ATGGCTTCTG GGTCTGGAAG GCTGAGGTTG CTTGTGTCTC TGCATTTGCA     1680

GTAGAATTTA CACGCGTAGT TGAACCTTTT TTCTTTGGAG ATCTTACAGG AGAAAGATAC     1740

ATATCTGCTG CAGTGTGATT ATTCTGGAGA GGAAGATTAA GAGGACAAGC AGATTCAAGG     1800

TGATCAGTTG GTCCTTCTCG GTCCTTTGAT TGTTTAATAA GATCAAATAA AGGTGAATCT     1860

GAGAGCCATG CAAGGGATTC CATGATTCGA TGTTCACATC GTTCTAAATG TTTTATCATT     1920

TCTCTTGTCA AGTTGCCTTC TGCTTTGATA AAACTTTCGA TCACTTTGTA AAAATCAAAG     1980

GCTTTTAAAT TAAGCACATT CAGAATCCAT GGGAAAGACA AATCTGTTCC AGAATCAAGA     2040

TTCTGAGATG TACTTCTGCT ATATGTGGCC ATTACAACCT CAAGAGCGCA CGCCAATAAA     2100

GACATATGAA AAATGTTGTC ATTCAGAAGT TTGCTAAAAT TTTGAATGGA TAATCGTTCT     2160

TCTTCTGATT TAAGCATGGA TTCCATTACT CGGTAATACA AGCGAACTCC AAGTTTGTAT     2220

CGCTGTGATC CAATTTCGAC ACAACCCTGT CCCACAGCTT TAGCAAATTT CTCTTTAAAG     2280

ATGTATCCTA TATCCTTCAC TCTTTTCAGT ATACTTTCTT TTGGATTCAC TGTGCAGTTG     2340

TTAAAATAGG AAATCAGATT TTCTGAAGGT TGATCACTTG CTGAATTTAA AATCATCATT     2400

AATTGTTGGA TAGTGTTCAT AACAGTCCTA ACTGGAGTGT GTGGAGGAAT TACATTCACC     2460

TCTTCATCAA GGTTACTTTT TCGTGGTGTT CTCTGTGTTT CAAAACTGTC TATAGAATCA     2520

GTCTGAAGAG TTTTATCATG ATCCAAAAAT AATCTTGCAT CTAGATCTTT ATTTTTAAGA     2580

TAAATTTCTT CGTATCGTTT AGAAAGATTT TCAACCTCTG GAAGTCCATT AGATGTTACA     2640

AGTCCAAGAG AATTCATAAA AGGTATAAAA TTTTTGAAAT AAACATTTTT CACCTCATCT     2700

ATATTACATT CATGTTCTTT ACAGAGAACT TCAATAATTC TTGTATCATT TTCTAGTTGT     2760

TTTGCTATCC GTGCACTCCT GTTCTGACCT CGCCTGGGTG TTCGAGGTGA ACCATTAATG     2820

GGTATAACAG CTGTTTTATA TGGTTCTTTG AGCAACATGG GAGGTGAGAG TTTAATAAAA     2880

TAGTCAAGGA CACATAGCAT TAACTGAAAT GAAATCACCA GATCATCTTC CATTTGTAAT     2940
```

```
ACTTCCCCTT TAGCTAATAA AAATGTGATC CAAGAAACTT TTAGCACCAA TGCAGAATTT    3000

ATTTCAGTAG ATATCGAACT GCTGGGTTGT GTCAAATATA TAAGTTCACA TGTCCTTTCC    3060

AATTTGCTGA AGAGTGCAAA CAATACATCA TACTTCTTCA ACAGTCTTGA CATAGCATTA    3120

TCAACTTTGG TACTGGTATC AATTTCTTTT AGTAAGTTAA AGAATTTATG GACACTGATT    3180

TCTATGTTTT TCTGTAGCTC AGTAAAAGTG AACGACATCT CATCTAGGTC GG           3232
```

(2) INFORMATION FOR SEQ ID NO:3:

(i) SEQUENCE CHARACTERISTICS:
        (A) LENGTH: 816 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ser Phe Thr Phe Thr Glu Leu Gln Lys Asn Ile Glu Ile Ser Val
 1               5                  10                  15

His Lys Phe Phe Asn Leu Leu Lys Glu Ile Asp Thr Ser Thr Lys Val
             20                  25                  30

Asp Asn Ala Met Ser Arg Leu Leu Lys Lys Tyr Asp Val Leu Phe Ala
         35                  40                  45

Leu Phe Ser Lys Leu Glu Arg Thr Cys Glu Leu Ile Tyr Leu Thr Gln
 50                  55                  60

Pro Ser Ser Ser Ile Ser Thr Glu Ile Asn Ser Ala Leu Val Leu Lys
 65                  70                  75                  80

Val Ser Trp Ile Thr Phe Leu Leu Ala Lys Gly Glu Val Leu Gln Met
             85                  90                  95

Glu Asp Asp Leu Val Ile Ser Phe Gln Leu Met Leu Cys Val Leu Asp
            100                 105                 110

Tyr Phe Ile Lys Leu Ser Pro Pro Met Leu Leu Lys Glu Pro Tyr Lys
        115                 120                 125

Thr Ala Val Ile Pro Ile Asn Gly Ser Pro Arg Thr Pro Arg Arg Gly
    130                 135                 140

Gln Asn Arg Ser Ala Arg Ile Ala Lys Gln Leu Glu Asn Asp Thr Arg
145                 150                 155                 160

Ile Ile Glu Val Leu Cys Lys Glu His Glu Cys Asn Ile Asp Glu Val
                165                 170                 175

Lys Asn Val Tyr Phe Lys Asn Phe Ile Pro Phe Met Asn Ser Leu Gly
            180                 185                 190

Leu Val Thr Ser Asn Gly Leu Pro Glu Val Glu Asn Leu Ser Lys Arg
        195                 200                 205

Tyr Glu Glu Ile Tyr Leu Lys Asn Lys Asp Leu Asp Ala Arg Leu Phe
    210                 215                 220

Leu Asp His Asp Lys Thr Leu Gln Thr Asp Ser Ile Asp Ser Phe Glu
225                 230                 235                 240

Thr Gln Arg Thr Pro Arg Lys Ser Asn Leu Asp Glu Glu Val Asn Val
                245                 250                 255

Ile Pro Pro His Thr Pro Val Arg Thr Val Met Asn Thr Ile Gln Gln
            260                 265                 270

Leu Met Met Ile Leu Asn Ser Ala Ser Asp Gln Pro Ser Glu Asn Leu
        275                 280                 285

Ile Ser Tyr Phe Asn Asn Cys Thr Val Asn Pro Lys Glu Ser Ile Leu
    290                 295                 300
```

-continued

```
Lys Arg Val Lys Asp Ile Gly Tyr Ile Phe Lys Glu Lys Phe Ala Lys
305                 310                 315                 320

Ala Val Gly Gln Gly Cys Val Glu Ile Gly Ser Gln Arg Tyr Lys Leu
                325                 330                 335

Gly Val Arg Leu Tyr Tyr Arg Val Met Glu Ser Met Leu Lys Ser Glu
            340                 345                 350

Glu Glu Arg Leu Ser Ile Gln Asn Phe Ser Lys Leu Leu Asn Asp Asn
        355                 360                 365

Ile Phe His Met Ser Leu Leu Ala Cys Ala Leu Glu Val Val Met Ala
    370                 375                 380

Thr Tyr Ser Arg Ser Thr Ser Gln Asn Leu Asp Ser Gly Thr Asp Leu
385                 390                 395                 400

Ser Phe Pro Trp Ile Leu Asn Val Leu Asn Leu Lys Ala Phe Asp Phe
                405                 410                 415

Tyr Lys Val Ile Glu Ser Phe Ile Lys Ala Glu Gly Asn Leu Thr Arg
            420                 425                 430

Glu Met Ile Lys His Leu Glu Arg Cys Glu His Arg Ile Met Glu Ser
        435                 440                 445

Leu Ala Trp Leu Ser Asp Ser Pro Leu Phe Asp Leu Ile Lys Gln Ser
    450                 455                 460

Lys Asp Arg Glu Gly Pro Thr Asp His Leu Glu Ser Ala Cys Pro Leu
465                 470                 475                 480

Asn Leu Pro Leu Gln Asn Asn His Thr Ala Ala Asp Met Tyr Leu Ser
                485                 490                 495

Pro Val Arg Ser Pro Lys Lys Lys Gly Ser Thr Thr Arg Val Asn Ser
            500                 505                 510

Thr Ala Asn Ala Glu Thr Gln Ala Thr Ser Ala Phe Gln Thr Gln Lys
        515                 520                 525

Pro Leu Lys Ser Thr Ser Leu Ser Leu Phe Tyr Lys Lys Val Tyr Arg
    530                 535                 540

Leu Ala Tyr Leu Arg Leu Asn Thr Leu Cys Glu Arg Leu Leu Ser Glu
545                 550                 555                 560

His Pro Glu Leu Glu His Ile Ile Trp Thr Leu Phe Gln His Thr Leu
                565                 570                 575

Gln Asn Glu Tyr Glu Leu Met Arg Asp Arg His Leu Asp Gln Ile Met
            580                 585                 590

Met Cys Ser Met Tyr Gly Ile Cys Lys Val Lys Asn Ile Asp Leu Lys
        595                 600                 605

Phe Lys Ile Ile Val Thr Ala Tyr Lys Asp Leu Pro His Ala Val Gln
    610                 615                 620

Glu Thr Phe Lys Arg Val Leu Ile Lys Glu Glu Tyr Asp Ser Ile
625                 630                 635                 640

Ile Val Phe Tyr Asn Ser Val Phe Met Gln Arg Leu Lys Thr Asn Ile
                645                 650                 655

Leu Gln Tyr Ala Ser Thr Arg Pro Pro Thr Leu Ser Pro Ile Pro His
            660                 665                 670

Ile Pro Arg Ser Pro Tyr Lys Phe Pro Ser Ser Pro Leu Arg Ile Pro
        675                 680                 685

Gly Gly Asn Ile Tyr Ile Ser Pro Leu Lys Ser Pro Tyr Lys Ile Ser
    690                 695                 700

Glu Gly Leu Pro Thr Pro Thr Lys Met Thr Pro Arg Ser Arg Ile Leu
705                 710                 715                 720

Val Ser Ile Gly Glu Ser Phe Gly Thr Ser Glu Lys Phe Gln Lys Ile
                725                 730                 735
```

```
Asn Gln Met Val Cys Asn Ser Asp Arg Val Leu Lys Arg Ser Ala Glu
            740             745             750

Gly Ser Asn Pro Pro Lys Pro Leu Lys Lys Leu Arg Phe Asp Ile Glu
            755             760             765

Gly Ser Asp Glu Ala Asp Gly Ser Lys His Leu Pro Gly Glu Ser Lys
    770             775             780

Phe Gln Gln Lys Leu Ala Glu Met Thr Ser Thr Arg Thr Arg Met Gln
785             790             795             800

Lys Gln Lys Met Asn Asp Ser Met Asp Thr Ser Asn Lys Glu Glu Lys
                805             810             815
```